US009023813B2

(12) United States Patent
Shull et al.

(10) Patent No.: US 9,023,813 B2
(45) Date of Patent: May 5, 2015

(54) SYNTHESIS AND USE OF GLYCOSIDE DERIVATIVES OF PROPOFOL

(75) Inventors: Brian Shull, Durham, NC (US); John Baldwin, Gwynedd Valley, PA (US); Ramesh Gopalaswamy, Morrisville, NC (US); Zishan Haroon, Chapel Hill, NC (US)

(73) Assignee: Nutek Pharma Ltd., Chapel Hill, NC (US)

( * ) Notice: Subject to any disclaimer, the term of this patent is extended or adjusted under 35 U.S.C. 154(b) by 0 days.

(21) Appl. No.: 13/442,485

(22) Filed: Apr. 9, 2012

(65) Prior Publication Data

US 2012/0264702 A1    Oct. 18, 2012

(51) Int. Cl.
*C07H 15/18* (2006.01)
*C07H 5/10* (2006.01)
*A61K 31/7028* (2006.01)
*C07H 15/04* (2006.01)
*C07H 15/203* (2006.01)
*C07H 15/26* (2006.01)

(52) U.S. Cl.
CPC ............... *C07H 15/18* (2013.01); *C07H 5/10* (2013.01); *A61K 31/7028* (2013.01); *C07H 15/04* (2013.01); *C07H 15/203* (2013.01); *C07H 15/26* (2013.01)

(58) Field of Classification Search
None
See application file for complete search history.

(56) References Cited

U.S. PATENT DOCUMENTS 6,093,805 A * 7/2000 Shull et al. .................. 536/4.1
6,254,853 B1 * 7/2001 Hendler et al. ............. 424/45

FOREIGN PATENT DOCUMENTS

CN    101298426 A  * 11/2008  ............ C07C 233/56
WO   WO 2004033424 A1 * 4/2004  ............ C07D 207/16

OTHER PUBLICATIONS

Jin et al., CN 101298426 A, 2008, machine translation, Retreived on Aug. 26, 2013 from http://worldwide.espacenet.com.*
Carson, S. S., Kress, J. P., Rodgers, J. E., Vinayak, A., Campbell-Bright, S., Levitt, J., ... & Hall, J. (2006). A randomized trial of intermittent lorazepam versus propofol with daily interruption in mechanically ventilated patients. Critical care medicine, 34(5), 1326-1332.*
Férriz, J. M., & Vinsova, J. (2010). Prodrug design of phenolic drugs. Current pharmaceutical design, 16(18), 2033-2052.*
Schmidt, F., & Monneret, C. (2003). Prodrug mono therapy: Synthesis and biological evaluation of an etoposide glucuronide-prodrug. Bioorganic & medicinal chemistry, 11(10), 2277-2283.*
Bettschart-Wolfensberger, R. et al. (2000) "Cardiopulmonary side-effects and pharmacokinetics of an emulsion of propofol (Disoprivan) in comparison to propofol solved in polysorbate 80 in goats," *Journal of Veterinary Medicine. A, Physiology, Pathology, Clinical Medicine* 47(6), 341-350.
Egan, T. et al. (2003) "The pharmacokinetics and pharmacodynamics of propofol in a modified cyclodextrin formulation (Captisol) versus propofol in a lipid formulation (Diprivan): an electroencephalographic and hemodynamic study in a porcine model," *Anesthesia and Analgesia* 97(1), 72-79, table of contents.

(Continued)

*Primary Examiner* — Shaojia Anna Jiang
*Assistant Examiner* — Dale R Miller
(74) *Attorney, Agent, or Firm* — Medlen + Carroll, LLP

(57) ABSTRACT

The present invention relates to methods and compositions for the synthesis, production, and use of pro-drug propofol analogs. This invention relates to a method for the production of a broad group of glycosylated propofol carbohydrate derivatives.

34 Claims, 18 Drawing Sheets

(56) References Cited

OTHER PUBLICATIONS

Ellett, M. (2010) "Review of propofol and auxiliary medications used for sedation," *Gastroenterology Nursing* 33(4), 284-295; quiz 296.

Ellett, M. L. C. (2010) "A literature review of the safety and efficacy of using propofol for sedation in endoscopy," *Gastroenterology Nursing* 33(2), 111-117.

Fechner, J. et al. (2003) "Pharmacokinetics and clinical pharmacodynamics of the new propofol prodrug GPI 15715 in volunteers," *Anesthesiology* 99(2), 303-313.

Glen, J. B. et al. (1984) "Pharmacology of an emulsion formulation of ICI 35 868," *British Journal of Anaesthesia* 56(6), 617-626.

Gottlieb, H. E. et al. (1997) "NMR Chemical Shifts of Common Laboratory Solvents as Trace Impurities," *Journal of Organic Chemistry* 62(21), 7512-7515.

Harris, E. A. et al. (2009) "Monitored anesthesia care (MAC) sedation: clinical utility of fospropofol," *Therapeutics and Clinical Risk Management* 5, 949-959.

Hart, B. (2000) "'Diprivan': a change of formulation," *European Journal of Anaesthesiology* 17(1), 71-73.

Knibbe, C. A. J. et al. (2004) "Long-term sedation with propofol 60 mg ml$^{-1}$ vs. propofol 10 mg$^{-1}$ ml in critically ill, mechanically ventilated patients," *Acta Anaesthesiologica Scandinavica* 48(3), 302-307.

Lamond, D. W. (2010) "Review article: Safety profile of propofol for paediatric procedural sedation in the emergency department," *Emergency Medicine Australasia* 22(4), 265-286.

Levitzky, B. et al. (2008) "Fospropofol disodium injection for the sedation of patients undergoing colonoscopy," *Therapeutics and Clinical Risk Management* 4(4), 733-738.

McKeage, K. et al. (2003) "Propofol: A Review of its Use in Intensive Care Sedation of Adults," *CNS Drugs* 17(4), 235-272.

Paul, M. et al. (2003) "Pharmacological characteristics and side effects of a new galenic formulation of propofol without soyabean oil," *Anaesthesia* 58(11), 1056-1062.

Rau, J. et al. (2001) "Propofol in an emulsion of long- and medium-chain triglycerides: the effect on pain," *Anesthesia and Analgesia* 93(2), 382-384 , 383rd contents page.

Ravenelle, F. et al. (2008) "Novel lipid and preservative-free propofol formulation: properties and pharmacodynamics," *Pharmaceutical Research* 25(2), 313-319.

Shao, X. et al. (2000) "Bisulfite-containing propofol: is it a cost-effective alternative to Diprivan for induction of anesthesia?," *Anesthesia and Analgesia* 91(4), 871-875.

Sneyd, J. R. (2004) "Recent advances in intravenous anaesthesia," *British Journal of Anaesthesia* 93(5), 725-736.

Sneyd, J. R. et al. (2010) "New drugs and technologies, intravenous anaesthesia is on the move (again)," *British Journal of Anaesthesia* 105(3), 246-254.

Song, D. et al. (2004) "Comparison of a lower-lipid propofol emulsion with the standard emulsion for sedation during monitored anesthesia care," *Anesthesiology* 100(5), 1072-1075.

Song, D. et al. (2004) "The pharmacodynamic effects of a lower-lipid emulsion of propofol: a comparison with the standard propofol emulsion," *Anesthesia and Analgesia* 98(3), 687-691, table of contents.

Symington, L. et al. (2006) "A review of the use of propofol for procedural sedation in the emergency department," *Emergency Medicine Journal* 23(2), 89-93.

Tronchet, J. M. J. et al. (1995) "Spin-labelled glycolipid analogues:—glucose series," *Carbohydrate Research* 275(2), 245-258.

Ward, D. et al. (2002) "Pharmacodynamics and pharmacokinetics of propofol in a medium-chain triglyceride emulsion," *Anesthesiology* 97(6), 1401-1408.

Yavas, S. et al. (2008) "Interactive web simulation for propofol and fospropofol, a new propofol prodrug," *Anesthesia and Analgesia* 106(3), 880-883, table of contents.

\* cited by examiner

General structure
n = 1-9 with n = 1, X = Y = Z = O,
these are the same structure
as shown above

[CARB-Y-(CH$_2$)$_n$]$_2$CHCH$_2$-X$\overset{Z}{-}$O-（2,6-diisopropylphenyl)

n preferably 1

General structure
n = 1-9 with n = 1, X = Y = Z = O,
these are the same structure
as shown above

[CARB-Y-(CH$_2$)$_n$]$_2$CHCH$_2$-X$\overset{Z}{-}$O-(2,6-diisopropylphenyl)

n preferably 1 or 2

SYNTHESIS AND USE OF GLYCOSIDE DERIVATIVES OF PROPOFOL

FIELD OF THE INVENTION

The present invention relates to methods and compositions for the production and use of pro-drug analogs. This invention relates to a method for the production of a broad group of novel glycoside derivatives of propofol. The invention also importantly relates to the resulting glycosides as novel compounds of diverse application having desired properties including pharmacodynamic properties; and to medicaments containing the pro-drug compounds.

BACKGROUND OF THE INVENTION

There are a number of potentially useful drugs with poor water solubility, among these is propofol. One approach to imparting better water solubility involves formulating the drug with polymers. See U.S. Pat. No. 7,550,155 [1]. However, some of these polymers have been found to incorporate into cell membranes. An approach that would be more compatible with a greater variety of functional groups, allowing easy access to propofol analogs containing a carbohydrate in which the pro-drug efficiently and quickly releases the drug in vivo is highly desirable.

SUMMARY OF THE INVENTION

The present invention relates to methods and compositions for the production and use of propofol pro-drug analogs. This invention relates to a method for the production of a broad group of novel glycoside derivatives of drugs. The invention also importantly relates to the resulting glycosides as novel compounds of diverse application having desired properties including pharmacodynamic properties; and to medicaments containing the pro-drug compound.

In one embodiment, the present invention contemplates a glycosylated propofol compound of the formula: CARB-T-L-Propofol wherein CARB is a carbohydrate connected through a chemical tether T to linking group L which is connected to Propofol, wherein said carbohydrate is selected from the group consisting of a mono-, di- and tri-saccharides, wherein said linker is created by chemical modification of a hydroxyl group on propofol, and wherein said tether comprises —$(CH_2)_m$— wherein m is a whole number between 1 and 10.

In one embodiment, the present invention contemplates a glycosylated propofol compound of the formula: CARB-T-L-Propofol wherein CARB is a carbohydrate connected through a chemical tether T to linking group L which is connected to Propofol, wherein said carbohydrate is selected from the group consisting of a mono-, di- and tri-saccharides, wherein said linker is created by chemical modification of a hydroxyl group on propofol, and wherein said tether comprises —$(CRR')_m$— wherein R and R' are independent and can be hydrogen, alkyl, aryl, substituted alkyl, substituted aryl, arylalkyl, substituted arylalkyl, cycloalkyl, substituted cycloalkyl, heteoalkyl, substituted heteroalkyl, heteroaryl, substituted heteroaryl, heterocyclyl, substituted heterocyclcl, heteroarylalkyl, or substituted heteroarylalky and wherein m is a whole number between 1 and 10.

In one embodiment, the present invention contemplates a glycosylated propofol compound of the formula: CARB-T-L-Propofol, wherein CARB is a carbohydrate connected through the chemical tether T to linking group L which is connected to propofol, wherein said carbohydrate is selected from the group consisting of a mono-, di- and tri-saccharides, wherein said linker is created by chemical modification of a hydroxyl group on propofol, and wherein said tether comprises —$(CR^1R^2)_m(CR^3R^4)_n(CR^5R^6)_p$— branched tether, wherein m, n, and p are independent, and where n and p can be a whole number between 0 and 10 and m can be a whole number between 1 and 10 (and in which the sum of m, n and p are preferably 2 or 3), and where $R^1$, $R^2$, $R^3$, $R^4$, $R^5$ and $R^6$ are each independent can be hydrogen, alkyl, aryl, substituted alkyl, substituted aryl, arylalkyl, substituted arylalkyl, cycloalkyl, substituted cycloalkyl, heteoalkyl, substituted heteroalkyl, heteroaryl, substituted heteroaryl, heterocyclyl, substituted heterocyclycl, heteroarylalkyl, or substituted heteroarylalky. Any of $R^1$, $R^2$, $R^3$, $R^4$, $R^5$ and $R^6$ can be joined to provide a cyclic tether. For simple straight chain tethers, n and p=0, $R^1$ and $R^2$=H, and the tether formula —$(CR^1R^2)_m(CR^3R^4)_n(CR^5R^6)_p$— collapses to —$(CH_2)_m$— where m is a whole number between 1 and 10 (preferably between 1 and 3, and most preferably 2 and 3). In one embodiment, said chemical modification comprises reacting propofol with a reactant selected from the group consisting of phosgene, triphosgene, thiophosgene, and oxalyl chloride so as to create a linker intermediate. In one embodiment, said linker intermediate is a chloroformate. In one embodiment, said linker intermediate is a thionochoroformate. In one embodiment, the linker intermediate is reacted such that said glycosylated propofol comprises a carbonate, a thiocarbonate, or a carbamate group. In one embodiment, said carbohydrate is a cyclic monosaccharide. In one embodiment, said cyclic monosaccharide is a pyranoside (6 member ring). In one embodiment, said cyclic monosaccharide is a furanoside (5 member ring). In one embodiment, said carbohydrate has additional functional groups that are protected with protecting groups (e.g., wherein said protected functional groups are acetylated) (or wherein the said carbohydrate has its functional group protected with protecting groups). In one embodiment, said carbohydrate containing protecting groups is an acetylated pyranoside. In one embodiment, said carbohydrate is a disaccharide selected from the group consisting of a lactose-derived glycal, and a maltose-derived glycal.

In one embodiment, said glycosylated propofol compound, CARB-T-L-Propofol has the structure:

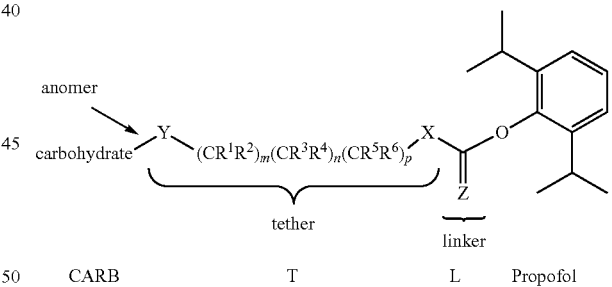

wherein Z is O or S, Y is O or S, and X is $CH_2$, CHR, CRR', OC(O), NHC(O), NRC(O), NH, NR, O, or S, wherein R and R' are independent and can be hydrogen, alkyl, aryl, substituted alkyl, substituted aryl, arylalkyl, substituted arylalkyl, cycloalkyl, substituted cycloalkyl, heteoalkyl, substituted heteroalkyl, heteroaryl, substituted heteroaryl, heterocyclyl, substituted heterocyclycl, heteroarylalkyl, or substituted heteroarylalky, wherein m, n and p are independent and can be whole number between 1 and 10 (the sum n, m, and p are most preferably 2 or 3), where $R^1$, $R^2$, $R^3$, $R^4$, $R^5$ and $R^6$ (and R if X=NR or NRC(O)) are each independent can be hydrogen, alkyl, aryl, substituted alkyl, substituted aryl, arylalkyl, substituted arylalkyl, cycloalkyl, substituted cycloalkyl, heteoalkyl, substituted heteroalkyl, heteroaryl, substituted heteroaryl, heterocyclyl, substituted heterocyclycl, heteroarylalkyl, or substituted heteroarylalky, and wherein the anomer is either α or β.

In one embodiment, CARB-T-L-Propofol has the structure:

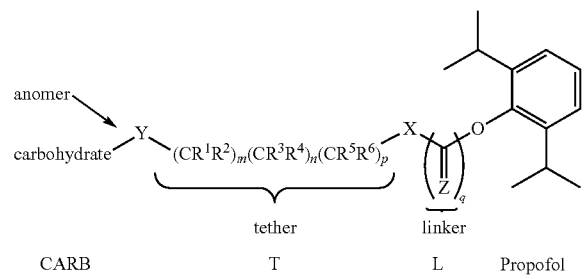

wherein Z is O or S, q is 1 or 2, Y is O or S, and X is $CH_2$, CHR, CRR', OC(O), NHC(O), NRC(O), NH, NR, O, or S, wherein R and R' are independent and can be hydrogen, alkyl, aryl, substituted alkyl, substituted aryl, arylalkyl, substituted arylalkyl, cycloalkyl, substituted cycloalkyl, heteroalkyl, substituted heteroalkyl, heteroaryl, substituted heteroaryl, heterocyclyl, substituted heterocyclycl, heteroarylalkyl, or substituted heteroarylalky wherein m, n and p are independent and can be whole number between 1 and 10 (the sum n, m, and p are most preferably 2 or 3), where $R^1$, $R^2$, $R^3$, $R^4$, $R^5$ and $R^6$ (and R if X=NR or NRC(O)) are each independent can be hydrogen, alkyl, aryl, substituted alkyl, substituted aryl, arylalkyl, substituted arylalkyl, cycloalkyl, substituted cycloalkyl, heteoalkyl, substituted heteroalkyl, heteroaryl, substituted heteroaryl, heterocyclyl, substituted heterocyclycl, heteroarylalkyl, or substituted heteroarylalky, and wherein the anomer is either α or β.

In one embodiment, said glycosylated propofol compound, CARB-T-L-Propofol has the structure:

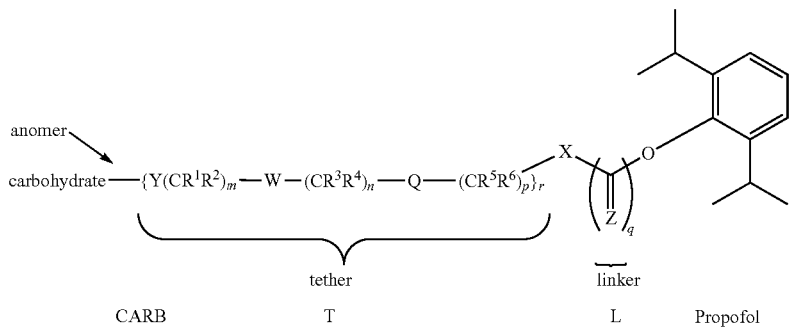

wherein Z is O or S, q is 1 or 2, Y is O or S, and X is $CH_2$, CHR, CRR', OC(O), NHC(O), NRC(O), NH, NR, O, or S, wherein R and R' are independent and can be hydrogen, alkyl, aryl, substituted alkyl, substituted aryl, arylalkyl, substituted arylalkyl, cycloalkyl, substituted cycloalkyl, heteoalkyl, substituted heteroalkyl, heteroaryl, substituted heteroaryl, heterocyclyl, substituted heterocyclycl, heteroarylalkyl, or substituted heteroarylalkyl, wherein W and Q are independently selected from O, N—R, S(O), $S(O)_2$, C(O), or S, wherein m, n and p are independent and can be whole number between 1 and 10 (the sum n, m, and p are most preferably 2 or 3), wherein r is a whole number between 1 and 100, where $R^1$, $R^2$, $R^3$, $R^4$, $R^5$ and $R^6$ (and R if X=NR or NRC(O)) are each independent can be hydrogen, alkyl, aryl, substituted alkyl, substituted aryl, arylalkyl, substituted arylalkyl, cycloalkyl, substituted cycloalkyl, heteoalkyl, substituted heteroalkyl, heteroaryl, substituted heteroaryl, heterocyclyl, substituted heterocyclycl, heteroarylalkyl, or substituted heteroarylalky, and wherein the anomer is either α or β. For In one embodiment, said glycosylated propofol compound, CARB-T-L-Propofol has the structure:

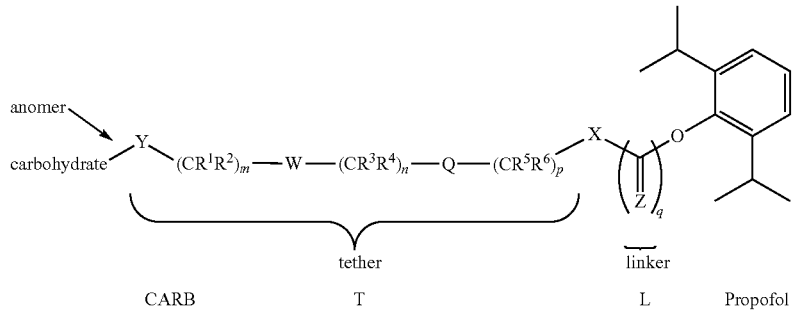

wherein Z is O or S, q is 1 or 2, Y is O or S, and X is $CH_2$, CHR, CRR', OC(O), NHC(O), NRC(O), NH, NR, O, or S, wherein W and Q are independently selected from O, N—R, S(O), $S(O)_2$, C(O), or S, wherein R and R' are independent and can be hydrogen, alkyl, aryl, substituted alkyl, substituted aryl, arylalkyl, substituted arylalkyl, cycloalkyl, substituted cycloalkyl, heteoalkyl, substituted heteroalkyl, heteroaryl, substituted heteroaryl, heterocyclyl, substituted heterocyclycl, heteroarylalkyl, or substituted heteroarylalky, wherein m, n and p are independent and can be whole number between 1 and 10 (the sum n, m, and p are most preferably 2 or 3), where $R^1$, $R^2$, $R^3$, $R^4$, $R^5$ and $R^6$ (and R if X=NR or NRC(O)) are each independent can be hydrogen, alkyl, aryl, substituted alkyl, substituted aryl, arylalkyl, substituted arylalkyl, cycloalkyl, substituted cycloalkyl, heteoalkyl, substituted heteroalkyl, heteroaryl, substituted heteroaryl, heterocyclyl, substituted heterocyclycl, heteroarylalkyl, or substituted heteroarylalky, and wherein the anomer is either α or β.

polyethylene glycol derived tethers, n and m=2, X and Y=O, W=O, Q=O, $R^1$, $R^2$, $R^3$, and $R^4$=H, and p=0, and the tether formula —$\{Y-(CR^1R^2)_m-W-(CR^3R^4)_n-Q-(CR^5R^6)\}_r$— collapses to —$\{Y-(CH_2CH_2-O-CH_2CH_2)\}_r$— where r is a whole number between 1 and 100. In one embodiment, said glycosylated compound, CARB-T-L-Propofol collapses to the structure below wherein Q=direct bond and p=0:

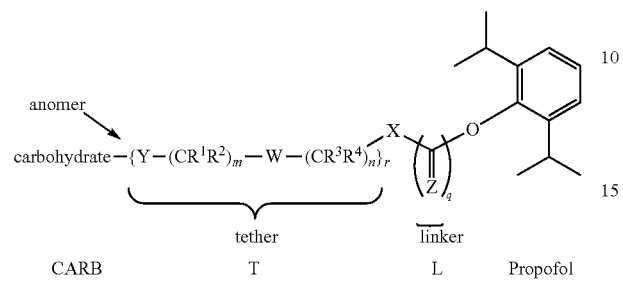

| CARB | T | L | Propofol |
|------|---|---|----------|
|      | tether | linker |     |

In one embodiment, the structure can then further collapse to the structure wherein X=Y=W=O, $R^1$, $R^2$, $R^3$, and $R^4$=H, and p=0:

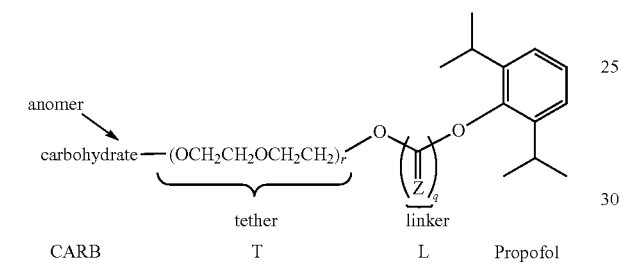

| CARB | T | L | Propofol |
|------|---|---|----------|
|      | tether | linker |     |

In one embodiment, said glycosylated propofol compound, CARB-T-L-Propofol would be one derived from the use of polyethylene glycols (PEG) in place of allyl alcohol described in the procedure (where Z=O and q=1). The use of such a polyethylene glycol tether would aid in compound solubility. The preparation of polyethylene glycol tether derivatives should be relatively easy to prepare.

In one embodiment, said glycosylated compound, CARB-T-L-Propofol has a PEG-related tether and has the structure:

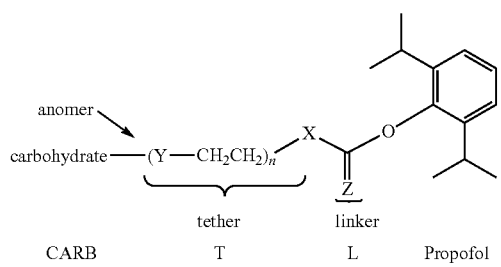

| CARB | T | L | Propofol |
| wherein Z is O or S, q is 1 or 2, Y is O or S, and X is CH₂, CHR, CRR', OC(O), NHC(O), NRC(O), NH, NR, O, or S, wherein W and Q are independently selected from O, N—R, S(O), S(O)₂, C(O), S, or direct bonds (i.e. do not exist or are nothing), wherein R and R' are independent and can be hydrogen, alkyl, aryl, substituted alkyl, substituted aryl, arylalkyl, substituted arylalkyl, cycloalkyl, substituted cycloalkyl, heteoalkyl, substituted heteroalkyl, heteroaryl, substituted heteroaryl, heterocyclyl, substituted heterocyclycl, heteroarylalkyl, or substituted heteroarylalky wherein m, n and p are independent and can be whole number between 0 and 10, where $R^1$, $R^2$, $R^3$, $R^4$, $R^5$ and $R^6$ (and R if X=NR or NRC(O)) are each independent can be hydrogen, alkyl, aryl, substituted alkyl, substituted aryl, arylalkyl, substituted arylalkyl, cycloalkyl, substituted cycloalkyl, heteoalkyl, substituted heteroalkyl, heteroaryl, substituted heteroaryl, heterocyclyl, substituted heterocyclycl, heteroarylalkyl, or substituted heteroarylalky, and wherein the anomer is either α or β.

In one embodiment, said glycosylated propofol compound, CARB-T-L-Propofol has a straight-chain tether and has the structure:

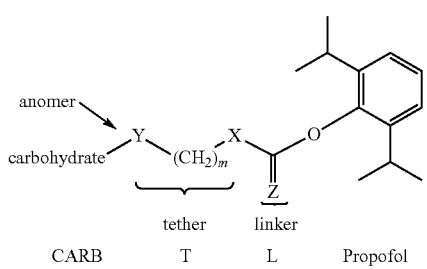

wherein Z is O or S, Y is O or S, X is CH₂, CHR, CRR', OC(O), NHC(O), NRC(O), NH, NR, O, or S, wherein R and R' are independent and can be hydrogen, alkyl, aryl, substituted alkyl, substituted aryl, arylalkyl, substituted arylalkyl, cycloalkyl, substituted cycloalkyl, heteoalkyl, substituted heteroalkyl, heteroaryl, substituted heteroaryl, heterocyclyl, substituted heterocyclycl, heteroarylalkyl, or substituted heteroarylalky, wherein m is a whole number between 1 and 10 (preferably between 2 and 10, and most preferably n is 2 or 3) and wherein the anomer is either α or β.

In one embodiment, CARB-T-L-Propofol has the structure:

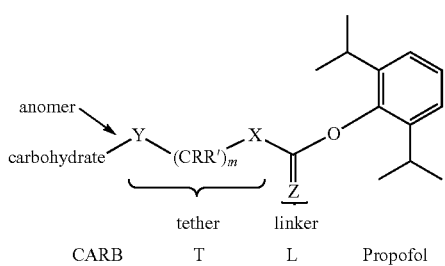

wherein Z is O or S, Y is O or S, X is CH₂, CHR, CRR', OC(O), NHC(O), NRC(O), NH, NR, O, or S, wherein R and R' are independent and can be hydrogen, alkyl, aryl, substituted alkyl, substituted aryl, arylalkyl, substituted arylalkyl, cycloalkyl, substituted cycloalkyl, heteoalkyl, substituted heteroalkyl, heteroaryl, substituted heteroaryl, heterocyclyl, substituted heterocyclycl, heteroarylalkyl, or substituted heteroarylalky, wherein m is a whole number between 1 and 10 (preferably between 2 and 10, and most preferably n is 2 or 3) and wherein the anomer is either α or β. In one embodiment, said glycosylated propofol compound has the structure:

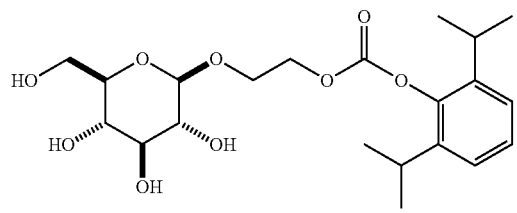 [SMILES: CC(C)c1cccc(C(C)C)c1OC(=O)OCCO[C@@H]1O[C@H](CO)[C@@H](O)[C@H](O)[C@H]1O]

In one embodiment, said glycosylated propofol compound has the structure:

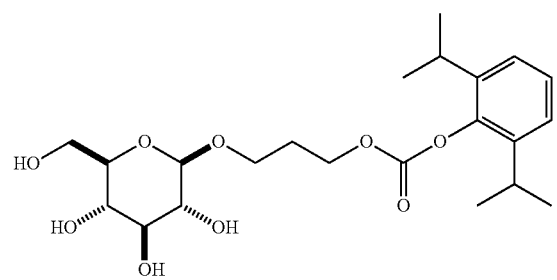 [SMILES: CC(C)c1cccc(C(C)C)c1OC(=O)OCCCO[C@@H]1O[C@H](CO)[C@@H](O)[C@H](O)[C@H]1O]

In one embodiment, said glycosylated propofol compound has the structure:

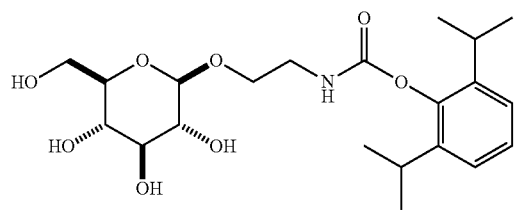 [SMILES: CC(C)c1cccc(C(C)C)c1OC(=O)NCCO[C@@H]1O[C@H](CO)[C@@H](O)[C@H](O)[C@H]1O]

In one embodiment, said glycosylated propofol compound has the structure:

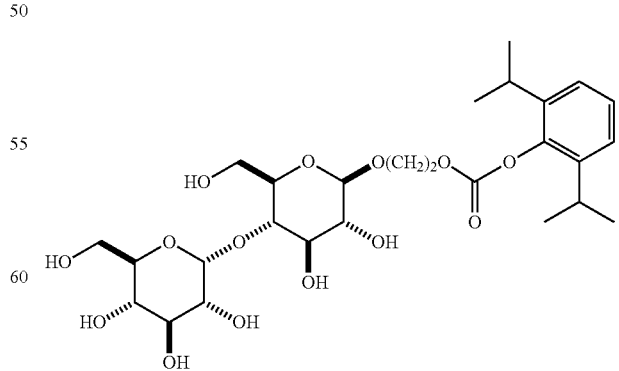

In one embodiment, said glycosylated propofol compound has the structure:

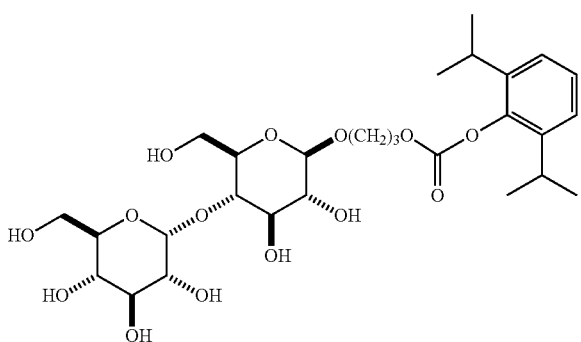

In one embodiment, said glycosylated propofol compound has the structure:

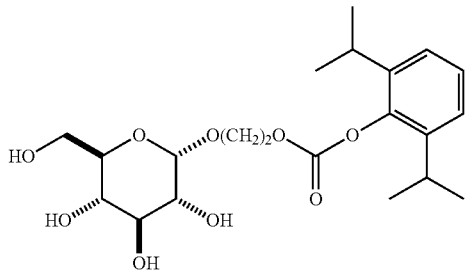

In one embodiment, said glycosylated propofol compound has the structure:

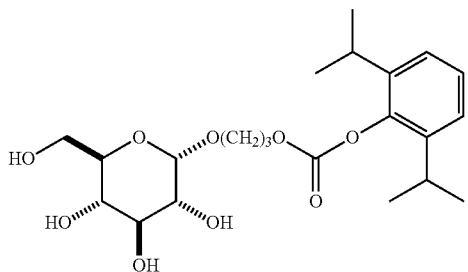

In one embodiment, the glycosylated propofol compound further comprises a diluent selected from the group consisting of water, saline, dextrose, glycerol, polyethylene glycol (PEG) and poly(ethylene glycol methyl ether). In one embodiment, the present invention contemplates a water-based formulation comprising the glycosylated propofol compound, wherein said formulation is suitable for intravenous administration. In one embodiment, the solubility of said glycosylated propofol compound in said formulation is greater than the solubility of an unglycosylated propofol (e.g. unmodified propofol). In one embodiment, the water-based formulation is oil-free.

In one embodiment, the present invention contemplates a method for making a glycosylated propofol compound of the formula: CARB-T-L-Propofol wherein CARB is a carbohydrate connected through a straight chain or branched chemical tether T to linking group L which is connected to propofol, said method comprising: a) providing propofol and a modified carbohydrate, said modified carbohydrate comprising a tethered functional group, said functional group selected from the group consisting of alcohols, amines and thiol groups; b) modifying the hydroxyl group on propofol, so as to create a modified propofol comprising a linker intermediate; and c) reacting said modified propofol with said modified carbohydrate, so as to create a glycosylated compound of the formula CARB-T-L-Propofol, wherein said linker intermediate is converted to a linker L. In one embodiment, said modifying of step b) comprises reacting propofol with a reactant selected from the group consisting of phosgene, triphosgene, thiophosgene, and oxalyl chloride so as to create a linker intermediate. In one embodiment, said reactant is a halo carbonate. In one embodiment, said linker intermediate is a chloroformate. In one embodiment, said linker intermediate is a thionochoroformate. In one embodiment, the linker intermediate is reacted so as to create glycosylated propofol comprising a carbonate, a thiocarbonate, or a carbamate group. In one embodiment, said modified carbohydrate has additional functional groups that are protected with protecting groups (or wherein the said carbohydrate has its functional group protected with protecting groups). In one embodiment, said protected functional groups are acetylated. In one embodiment, said carbohydrate containing protecting groups is an acetylated pyranoside. In one embodiment, after step c) said protecting groups are removed. In one embodiment, the linker intermediate is converted in step c) above to a linker having the formula C(Z) or C double bonded to Z, wherein Z is O or S. In one embodiment, said modified carbohydrate is selected from the group consisting of a mono-, di- and tri-saccharides. In one embodiment, said monosaccharide is a glucose-derived glycal. In one embodiment, said disaccharide is selected from the group consisting of a lactose-derived glycal and a maltose-derived glycal.

In one embodiment, the present invention contemplates a method for making a glycosylated propofol compound of the formula: CARB-T-L-Propofol wherein CARB is a carbohydrate connected through a straight chain or branched chemical tether T to linking group L which is connected to propofol, said method comprising: a) providing propofol and a modified carbohydrate, said modified carbohydrate comprising a tethered functional group, said functional group selected from the group consisting of alcohols, amines and thiol groups; b) modifying the hydroxyl, thiol, or amine group on the tether attached to the carbohydrate, so as to create a modified tether comprising a linker intermediate; and c) reacting said modified tethered carbohydrate with propofol, so as to create a glycosylated compound of the formula CARB-T-L-Propofol, wherein said linker intermediate is converted to linker L. In one embodiment, the linker intermediate is reacted so as to create glycosylated propofol comprising a carbonate, a thiocarbonate, or a carbamate group. In one embodiment, said modified carbohydrate has additional functional groups that are protected with protecting groups (wherein the said carbohydrate has its functional group protected with protecting groups). In one embodiment, said protected functional groups are acetylated. In one embodiment, said carbohydrate containing protecting groups is an acetylated pyranoside. In one embodiment, after step c) said protecting groups are removed. In one embodiment, said modified carbohydrate is selected from the group consisting of a mono-, di- and tri-saccharides. In one embodiment, said monosaccharide is a glucose-derived glycal. In one embodiment, said disaccharide is selected from the group consisting of a lactose-derived glycal and a maltose-derived glycal.

In one embodiment, the carbohydrate unit (CARB) or units attached to the drug are exemplified but not limited to 2,3-desoxy-2,3-dehydroglucose, glucoside, mannoside, galactoside, alloside, guloside, idoside, taloside, rhamnoside, maltoside, 2,3-desoxy-2,3-dehydromaltoside, 2,3- desoxymaltoside, lactoside, 2,3-desoxy-2,3-dehydro-lactoside, 2,3-desoxylactoside, glucouronate, glucosamine, galactosamine, mannosamine, N-acetylglucosamine, N-acetylgalactosamine, and N-acetylmannosamine. In one embodiment, the present invention contemplates the use of carbohydrate unit or units having five-membered rings, known as furanoses. In one embodiment, the present invention contemplates the use of carbohydrate unit or units having six-membered rings, known as pyranoses. Combinations of furanoses and pyranoses are also contemplated.

In one embodiment, the carbohydrate unit (CARB) or units attached to the drug contain acetate protecting group are exemplified but not limited to 2,3-desoxy-2,3-dehydroglucose diacetate, glucoside tetraacetate, mannoside tetraacetate, galactoside tetraacetate, alloside tetraacetate, guloside tetraacetate, idoside tetraacetate, taloside tetraacetate, rhamnoside triacetate, maltoside heptaacetate, 2,3-desoxy-2,3-dehydromaltoside pentaacetate, 2,3-desoxymaltoside pentaacetate, lactoside tetraacetate, 2,3-desoxy-2,3-dehydrolactoside pentaacetate, 2,3-desoxylactoside pentaacetate, glucouronate triacetate, N-acetylglucosamine triacetate N-acetylgalactosamine triacetate, and N-acetylmannosamine triacetate. In one embodiment, the present invention contemplates the use of carbohydrate unit or units having five-membered rings, known as furanoses. In one embodiment, the present invention contemplates the use of carbohydrate unit or units having six-membered rings, known as pyranoses. Combinations of furanoses and pyranoses are also contemplated.

In one embodiment, the carbohydrate unit (CARB) or units attached to the drug contain protecting groups exemplified but not limited to an acetyl group, including acetyl (Ac), chloroacetyl (ClAc), propionyl, benzoyl (Bz), and pivalyl (Piv). Non-acyl protecting groups include but not limited to benzyl (Bn), β-methoxyethoxymethyl ether (MEM), methoxymethyl ether (MOM), p-methoxybenzyl ether (PMB), methylthiomethyl ether, tetrahydropyran (THP), silyl ethers (including but not limited to trimethylsilyl (TMS), tert-butyldimethylsilyl (TBDMS), and triisopropylsilyl (TIPS) ethers), methyl ethers, and ethoxyethyl ethers (EE). In one embodiment, the carbohydrate unit (CARB) or units attached to the drug contain a protecting group exemplified but not limited to amine protecting groups: carbobenzyloxy (Cbz) group, p-methoxybenzyl carbonyl (Moz or MeOZ) group, tert-butyloxycarbonyl (BOC) group, 9-fluorenylmethyloxy-carbonyl (FMOC) group, benzyl (Bn) group, p-methoxybenzyl (PMB), dimethoxybenzyl (DMPM), p-methoxyphenyl (PMP) group, tosyl (Ts) group, and other sulfonamides (Nosyl & Nps) groups. In one embodiment, the carbohydrate unit (CARB) or units attached to the drug contain a protecting group exemplified but not limited to carbonyl protecting groups: acetals, ketals, acylals, and dithianes. Carboxylic acid protecting groups: alkyl esters, aryl esters, silyl esters.

It can also be contemplated that branched tethered analogs be prepared as well. These branched tethers can be prepared in a similar manner as those described above. The branching could be aliphatic, cyclic, contain other functionalities to aid in making the compound more water-soluble, or it could contain another carbohydrate. For example, in one embodiment, the present invention contemplates a non-carbohydrate functionality which increases water solubility. Non-limiting examples of such functionalities include sodium carboxylate and sodium sulfate.

In a preferred embodiment, the present invention contemplates that the tether T is branched and comprises another carbohydrate, wherein said carbohydrate is selected from the group consisting of a mono-, di- and tri-saccharides.

Examples of the latter are shown below. Since the analogs below contain two monosaccharides, it is expected that their water solubility would be more comparable to that of disaccharide analogs 24 and 25 than those containing just one monosaccharide moiety. It is important to note, however, that in vivo enzymatic hydrolysis of either of the monosaccharides of this branched analogs should result in spontaneous release of propofol. Thus, the pharmacokinetics of the branched tethered analogs below should more closely resemble that of the monosaccharide analogs, rather than the less favorable results obtained for disaccharide analogs 24 and 25. Thus it is quite possible that analogs similar to that shown below would have characteristics superior to those that have been prepared and described herein.

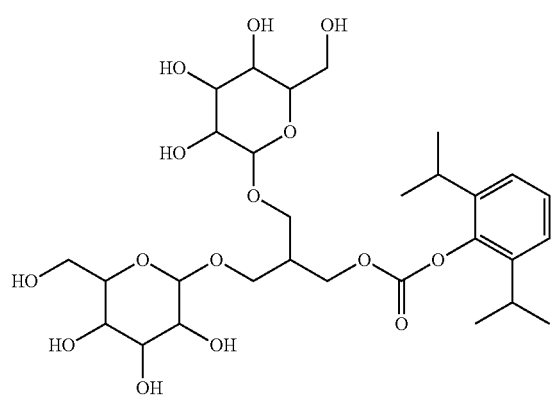

BT1

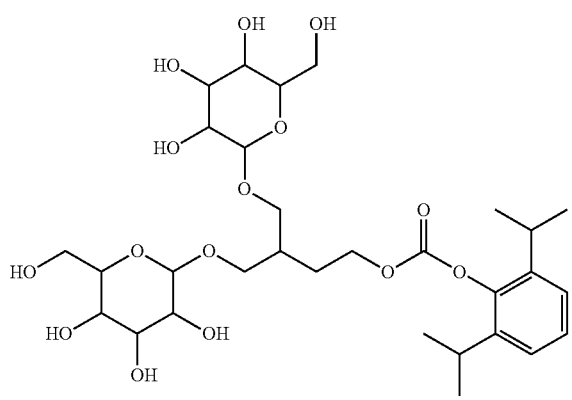

BT2

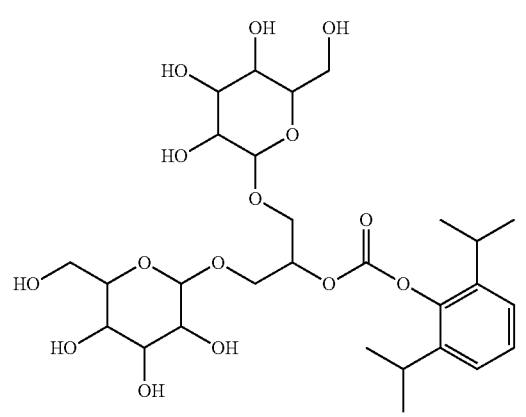

BT3

It is not intended that the present invention be limited by the medical uses for the glycoslated propofol compounds described herein. In one embodiment, the present invention contemplates a method of treating a subject, comprising: a) providing an glycosylated propofol compound of the formula: CARB-T-L-Propofol, wherein CARB is a carbohydrate connected through a chemical tether T to linking group L which is connected to Propofol, wherein said carbohydrate is selected from the group consisting of a mono-, di- and tri-saccharides, wherein said tether comprises —$(CR^1R^2)_m$ $(CR^3R^4)_n(CR^5R^6)_p$—, wherein m, n, and p are independent and can be a whole numbers between 0 and 10 (preferably when the sum of m, n and p are between 0 and 3) and where $R^1, R^2, R^3, R^4, R^5$ and $R^6$ are each independent can be hydrogen, alkyl, aryl, substituted alkyl, substituted aryl, arylalkyl, substituted arylalkyl, cycloalkyl, substituted cycloalkyl, heteoalkyl, substituted heteroalkyl, heteroaryl, substituted heteroaryl, heterocyclyl, substituted heterocyclycl, heteroarylalkyl, or substituted heteroarylalky. Any of $R^1, R^2, R^3, R^4, R^5$ and $R^6$ (including R when X=NR) can be joined to provide a cyclic tether. (it should be noted that for simple straight chain tethers, n and p=0, $R^1$ and $R^2$=H, and the tether formula —$(CR^1R^2)_m(CR^3R^4)_n(CR^5R^6)_p$— collapses to —$(CH_2)_m$—); and b) administering said glycosylated propofol compound to a subject. The subject can be a human or non-human animal. In one embodiment, said linker is created by chemical modification of a hydroxyl group on propofol so as to create a linker intermediate. In one embodiment, said linker intermediate is a chloroformate. In one embodiment, the linker intermediate is converted to a linker upon reaction with a modified carbohydrate so as to generate the glycosylated propofol. In one embodiment, the glycosylated propofol comprises a carbonate, a carbamate, or thiocarbonate group.

It is not intended that the present invention be limited by the timing of administration or the nature of subject's condition. In one embodiment, the compound can be administered before, during or after a medical procedure (e.g. a diagnostic or surgical procedure). In one embodiment, the procedure can involve the insertion of medical devices or tubes into the subject. For example, in one embodiment, the human is mechanically ventilated (e.g. the compound is administered to calm the patient in order to better tolerate mechanical ventilation). The procedure can be for minor surgery (e.g. removing teeth) or more complicated surgery.

It is not intended that the present invention be limited by the route of administration; all routes of administration (e.g. oral, nasal, etc.) can be employed. However, in a preferred embodiment, the administering is by intravenous administration. In a preferred embodiment, the compound is in a water-based, (and preferably oil-free) formulation. In one embodiment, said human after said administering is sedated (typically indicated by a reduction of alertness, sensitivity, irritability or agitation). In one embodiment, the subject is soporous.

DESCRIPTION OF THE INVENTION

The present invention relates to methods and compositions for the production and use of pro-drug propofol analogs. This invention relates to a method for the production of a broad group of novel glycoside derivatives of propofol. The invention also importantly relates to the resulting glycosides as novel compounds of diverse application having desired properties including pharmacodynamic properties; and to medicaments containing the pro-drug compounds.

In one embodiment, the present invention contemplates glycosylated propofol. Propofol is a short-acting, intravenously administered sedative agent and is approved for use in more than 50 countries. Its uses include the induction and maintenance of general anesthesia, sedation for mechanically ventilated adults, and procedural sedation for both adults and children. Propofol is also commonly used in veterinary medicine. McKeage (2003) is an excellent review on use of propofol [2] with discussions on dosage, formulation (issues with), human pharmacokinetics and pharmacodynamics. Ellett (2010) is an excellent review on propofol use [3,4]. Lamond (2010) is a very good review on the increasing use of propofol in pediatric procedural sedation [5]. Symington (2006) details the use of propofol in procedural sedation in the emergency department [6].

Propofol has very little water solubility so its formulation has been problematic. The standard formulation currently used is 1% or 2% propofol in 10% soya bean oil as long chain triglycerides with EDTA. Another major issue is that the administration causes great pain 80% of the time that it is used. The current solution for this is pretreatment with local anesthetics (e.g. lidocaine) (also see Table 2 in Sneyd (2004) [7]. Also, the lipid based formulation of propofol is susceptible to bacterial and fungal infection. Use of EDTA has been somewhat effective in curbing this serious contamination.

Sneyd (2004) is a good review on i.v. anesthetics with major focus on propofol [7]. Table 1 delineates different formulations both on the market as well as those tried in the clinic, including cyclodextrin-based and polysorbate-based ones [7].

Harris (2009) addresses issues with current formulation of propofol [8] and Egan (2003) compares a cyclodextrin-based formulation (Captisol®) versus propofol in the current lipid-based formulation [9]. Ravenelle (2007) describes a novel polymer-based formulation of propofol using amphiphilic block copolymers of poly-(N-vinyl-2-pyrrolidone) and poly-(D,L-lactide), PVP-PLA [10].

Fospropofol disodium (Aquavan®, Lusedra), approved by the FDA in 2008 and does not cause pain upon injection, is a phosphorylated prodrug of propofol, which upon hydrolysis in vivo by alkaline phosphatases releases the active drug propofol, formaldehyde and phosphate. However, there is significant time-lag to reach peak-effect when compared with propofol and patient recovery is correspondingly slower. Thus, fospropofol has a slower pharmacokinetic and pharmacodynamic profile than propofol lipid emulsion. On the other hand the advantage is that its slower profile may allow for an ease of administration that requires less frequent administration of medication for brief procedures. Moreover, fospropofol has side-effects not associated with propofol, which include perineal pain or paraesthesia. It should also be noted that fospropofol is approved for use only by persons trained in the administration of general anaesthesia.

Sneyd (2010) is an updated review and includes a section on fospropofol that outlines its advantages and disadvantages [11]. Levitzky (2008) reviews on the use of fospropofol for the sedation of patients undergoing colonoscopy, highlighting the pharmacokinetics, pharmacodynamics, risks, and common adverse events associated with fospropofol [12]. Harris (2009) gives a good overview of the pharmacokinetics, pharmacodynamics and clinical use of fospropofol [8]. Yavas (2008) describes an interactive web-based simulation for propofol and fospropofol and their pharmacokinetics and pharmacodynamics [13].

The 'ideal' anesthetic should, like propofol, have a rapid onset (<30 sec) and a short duration of action (~5 min), but it should also have a good safety margin. Regarding an 'ideal' prodrug of an anesthetic such as propofol, it is desirable that it has a rapid onset—close to that of propofol. Thus the prodrug should release propofol in vivo in a rapid, facile and near quantitative manner. Also, the prodrug should be devoid of any toxic or undesired side effects and a fast clearance of the prodrug would also be advantageous.

Figure 1:
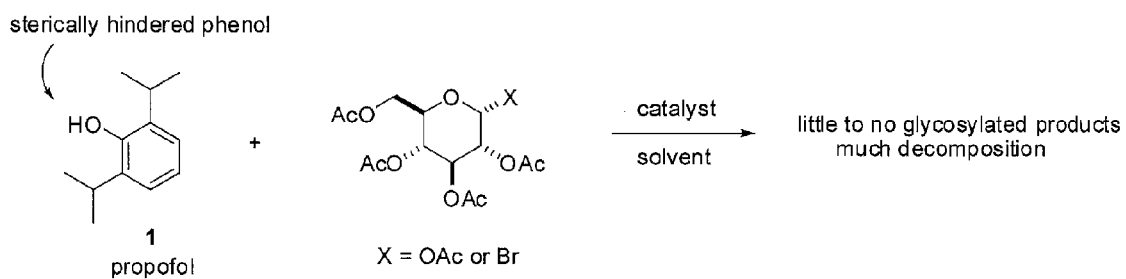
FIG. 1 shows a reaction scheme of initial unsuccessful attempts to directly glycosylate propofol.

Table 1 shows different formulations of propofol.

Table 2 shows methods to alleviate or modify pain on injection with propofol which have been evaluated in randomized controlled trials from Sneyd 2004 [7].

Table 3 shows the structure and solubility determination of propofol analogs.

Table 4 shows clinical observations of rats during Administration of propofol analogs during pharmacokinetics study as described in Example 27.

Table 5A shows pharmacokinetics study details for propofol, and compounds 9, 12, and 17 as described in Example 27.

Table 5B shows pharmacokinetics study details for compounds 24, 25, 32 and 33 as described in Example 27.

Table 6 shows the mean concentration of pro-drug and propofol in rat plasma after intravenous infusion administration as described in Example 27.

Table 7 shows mean concentration of propofol in rat plasma after intravenous infusion of each pro-drug of propofol as described in Example 27.

Table 8 shows how each of the propofol analogs prepared as well as some other examples contemplated correspond to the general formula.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "propofol" refers to a compound represented by the following chemical structure:

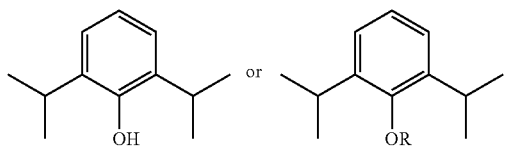

where R is H. Propofol also has the formal name 2,6-diisopropylphenol. It is not intended that the invention be limited to any particular derivative, analog or isomer of propofol or salt thereof. Examples of derivatives of propofol include but are in no way limited to propofol or glycoside derivatives of propofol. It is not intended that the present invention be limited by the type of chemical substituent or substituents that is or are coordinated to propofol. Examples of chemical substituents include but are in no way limited to hydrogen, methyl, ethyl, formyl, acetyl, phenyl, chloride, bromide, hydroxyl, methoxyl, ethoxyl, methylthiol, ethylthiol, propionyl, carboxyl, methoxy carbonyl, ethoxycarbonyl, methylthiocarbonyl, ethylthiocarbonyl, butylthiocarbonyl, dimethylcarbamyl, diethylcarbamyl, N-piperidinylcarbonyl, N-methyl-N'-piperazinylcarbonyl, 2-(dimethylamino)ethylcarboxy, N-morpholinylcarbonyl, 2-(dimethylamino)ethylcarbamyl, 1-piperidinylcarbonyl, methylsulfonyl, ethylsulfonyl, phenylsulfonyl, 2-piperidinylethyl, 2-morpholinylethyl, 2-(dimethylamino)ethyl, 2-(diethylamino)ethyl, butylthiol, dimethylamino, diethylamino, piperidinyl, pyrrolidinyl, imidazolyl, pyrazolyl, N-methylpiperazinyl, and 2-(dimethylamino)ethylamino.

"Epimers" refer to diastereomers that differ in configuration of only one stereogenic center. Diastereomers are a class of stereoisomers that are non-superposable, non-mirror images of one another, unlike enantiomers that are non-superposable mirror images of one another.

"Anomers" refer to a special type of epimer. It is a stereoisomer (diastereomer, more precisely) of a cyclic saccharide that differs only in its configuration at the hemiacetal or hemiketal carbon, also called the anomeric carbon.

Anomers are identified as "α" or "β" based on the relation between the stereochemistry of the exocyclic oxygen atom at the anomeric carbon and the oxygen attached to the configurational atom (defining the sugar as D or L), which is often the furthest chiral centre in the ring. The α anomer is the one in which these two positions have the same configuration; they are opposite in the β anomer.

For example in the case of α-D-glucopyranose vs. β-D-glucopyranose have the structures, respectively:

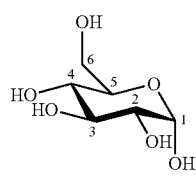

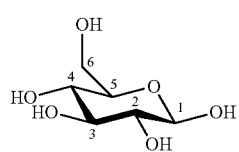

Unless otherwise stated, it can be assumed the current invention contemplates both α and β anomers described.

"Sugar" refers to a monosaccharide, disaccharide, trisaccharides, or polysaccharides. Monosaccharides have the general formula $(CH_2O)_n$, in which n is an integer larger than 2. Disaccharides have the general formula $C_n(H_2O)_{n-1}$, with n larger than 5. Polysaccharides include such substances as cellulose, dextrin, glycogen, and starch.

A "pharmaceutically acceptable monosaccharide" is a pharmaceutically acceptable aldose sugar, a pharmaceutically acceptable ketose sugar, or other specified sugar. Among the pharmaceutically acceptable aldose sugars within the contemplation of the present invention are erythrose, threose, ribose, arabinose, xylose, lyxose, allose, altrose, glucose, mannose, gulose, idose, galactose, and talose. Among the pharmaceutically acceptable ketose sugars preferred for use in the composition of the present invention are erythrulose, ribulose, xylulose, psicose, fructose, sorbose, tagatose, and sedoheptulose. Among the other specified sugars preferred for use in the composition of the present invention are fucose, fuculose, rhamnose, or any other deoxy sugar. Although either (D) or (L) isomers may be employed, the (D) form is generally preferable.

The present disaccharide derivatives are preferably derived from disaccharides of the general formula $C_{12}H_{22}O_{11}$ and may suitably be chosen from the group consisting of cellobiose, gentiobiose, lactose, lactulose, maltose, melibiose, sucrose, trehalose, and turanose. Preferably, the novel disaccharide derivatives are derived from lactose, maltose or sucrose.

The pharmaceutical compositions of the present invention may be prepared by formulating them in dosage forms which are suitable for peroral, rectal or nonparenteral administration, the last-mentioned including intravenous injection and administration into the cerebrospinal fluid. For this purpose, common carriers and routine formulation techniques may be employed.

"API" or "active pharmaceutical ingredient" means the substance in a pharmaceutical drug that is biologically active.

"Common carriers" means those which are employed in standard pharmaceutical preparations and includes excipients, binders and disintegrators the choice of which depends on the specific dosage form used. Typical examples of the excipient are starch, lactose, sucrose, glucose, mannitol and cellulose; illustrative binders are polyvinylpyrrolidone, starch, sucrose, hydroxypropyl cellulose and gum arabic; illustrative disintegrators include starch, agar, gelatin powder, cellulose, and CMC. Any other common excipients, binders and disintegrators may also be employed.

In addition of the carriers described above, the pharmaceutical composition of the present invention preferably contains antioxidants for the purpose of stabilizing the effective ingredient. Appropriate antioxidants may be selected from among those which are commonly incorporated in pharmaceuticals and include ascorbic acid, N-acetylcysteine, L-cysteine, D, L-α-tocopherol, and natural tocopherol.

Formulations of the pharmaceutical composition of the present invention which are suitable for peroral administration may be provided in the form of tablets, capsules, powders, granules, or suspensions in non-aqueous solutions such as syrups, emulsions or drafts, each containing one or more of the active compounds in predetermined amounts.

The granule may be provided by first preparing an intimate mixture of one or more of the active ingredients with one or more of the auxiliary components shown above, then granulating the mixture, and classifying the granules by screening through a sieve.

The tablet may be prepared by compressing or otherwise forming one or more of the active ingredients, optionally with one or more auxiliary components.

The capsule may be prepared by first making a powder or granules as an intimate mixture of one or more of the active ingredients with one or more auxiliary components, then charging the mixture into an appropriate capsule on a packing machine, etc.

The pharmaceutical composition of the present invention may be formulated as a suppository (for rectal administration) with the aid of a common carrier such a cocoa butter. The pharmaceutical composition of the present invention may also be formulated in a dosage form suitable for non-parenteral administration by packaging one or more active ingredients as dry solids in a sterile nitrogen-purged container. The resulting dry formulation may be administered to patients non-parenterally after being dispersed or dissolved in a given amount of aseptic water.

The dosage forms are preferably prepared from a mixture of the active ingredients, routine auxiliary components and one or more of the antioxidants listed above. If desired, the formulations may further contain one or more auxiliary components selected from among excipients, buffers, flavoring agents, binders, surfactants, thickening agents, and lubricants.

The dose of the various pro-drugs will of course vary with the route of administration, the severity of the disease to be treated, and the patient to be treated, but the exact dose ultimately chosen should be left to the good discretion of the doctor responsible for the treatment. If a desired dose is determined, the active ingredient may be administered once a day or, alternatively, it may be administered in up to as many portions as deemed appropriate at suitable intervals. The active ingredient may be straightforwardly administered without being mixed with any other components. However, for several reasons, typically for the purpose of providing ease in controlling the dose level, the active compound is preferably administered in a pharmaceutical dosage form.

The term "salts", as used herein, refers to any salt that complexes with identified compounds contained herein while retaining a desired function, e.g., biological activity. Examples of such salts include, but are not limited to, acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Pharmaceutically acceptable salts also include base addition salts which may be formed when acidic protons present are capable of reacting with inorganic or organic bases. Suitable pharmaceutically-acceptable base addition salts include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of the invention. Unless otherwise specifically stated, the present invention contemplates pharmaceutically acceptable salts of the considered pro-drugs.

As used herein, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; "imino" means =NH (see below for definitions of groups containing the term imino, e.g., alkylamino); "cyano" means —CN; "azido" means —N$_3$; "mercapto" means —SH; "thio" means =S; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); and "silyl" means —SiH$_3$ (see below for definitions of group(s) containing the term silyl, e.g., alkylsilyl).

As used herein, "olefin" means any of a class of unsaturated hydrocarbon containing one or more pairs of carbon atoms linked by a double bond (see covalent bond, saturation). Olefins may be classified by whether the double bond is in a ring (cyclic) or a chain (acyclic, or aliphatic) or by the number of double bonds (monoolefin, diolefin, etc.).

As used herein, "methylene" means a chemical species in which a carbon atom is bonded to two hydrogen atoms. The —CH$_2$— group is considered to be the standard methylene group. Methylene groups in a chain or ring contribute to its size and lipophilicity. In this context dideoxy also refers the methylene groups. In particular a 2,3-dideoxy compound is the same as 2,3-methylene (2,3-methylene-glycoside=2,3-dideoxy-glycoside).

For the groups below, the following parenthetical subscripts further define the groups as follows: "(Cn)" defines the exact number (n) of carbon atoms in the group; "(C≤n)" defines the maximum number (n) of carbon atoms that can be in the group; (Cn-n') defines both the minimum (n) and maximum number (n') of carbon atoms in the group. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3-10 carbon atoms)). Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3-10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr or i-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl or sec-Bu), —CH$_2$CH(CH$_3$)$_2$ (isobutyl or i-Bu), —C(CH$_3$)$_3$ (tert-butyl or t-Bu), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkanediyl" when used without the "substituted" modifier refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

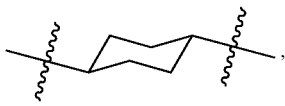 [SMILES: *C1CCC(*)CC1], are non-limiting examples of alkanediyl groups. The term "substituted alkanediyl" refers to a non-aromatic monovalent group, wherein the alkynediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$_2$—, —CH(Cl)—, —CH(OH)—, —CH(OCH$_3$)—, and —CH$_2$CH(Cl)—.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

The term "alkenediyl" when used without the "substituted" modifier refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

, are non-limiting examples of alkenediyl groups. The term "substituted alkenediyl" refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and at least one atom independently selected from the group consisting of N, O, F, Cl, Br, I, Si, P, and S. The following groups are non-limiting examples of substituted alkenediyl groups: —CF=CH—, —C(OH)=CH—, and —CH$_2$CH=C(Cl)—.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH$_3$)$_3$, is a non-limiting example of a substituted alkynyl group.

The term "alkynediyl" when used without the "substituted" modifier refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH$_2$—, and —C≡CCH(CH$_3$)— are non-limiting examples of alkynediyl groups. The term "substituted alkynediyl" refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and at least one atom independently selected from the group consisting of N, O, F, Cl, Br, I, Si, P, and S. The groups —C≡CCFH— and —C≡CCH(Cl)— are non-limiting examples of substituted alkynediyl groups.

The term "aryl" when used without the "substituted" modifier refers to a monovalent group with an aromatic carbon atom as the point of attachment, said carbon atom forming part of a six-membered aromatic ring structure wherein the ring atoms are all carbon, and wherein the monovalent group consists of no atoms other than carbon and hydrogen. Non-limiting examples of aryl groups include phenyl (Ph), methylphenyl, C$_6$H$_3$(CH$_3$)$_2$ (dimethylphenyl), —C$_6$H$_4$CH$_2$CH$_3$ (ethylphenyl), —C$_6$H$_4$CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH=CH$_2$ (vinylphenyl), —C$_6$H$_4$CH=CHCH$_3$, —C$_6$H$_4$C≡CH, —C$_6$H$_4$C≡CCH$_3$, naphthyl, and the monovalent group derived from biphenyl. The term "substituted aryl" refers to a monovalent group with an aromatic carbon atom as the point of attachment, said carbon atom forming part of a six-membered aromatic ring structure wherein the ring atoms are all carbon, and wherein the monovalent group further has at least one atom independently selected from the group consisting of N, O, F, Cl, Br, I, Si, P, and S, Non-limiting examples of substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, and —C$_6$H$_4$CON(CH$_3$)$_2$.

The term "arenediyl" when used without the "substituted" modifier refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of arenediyl groups include:

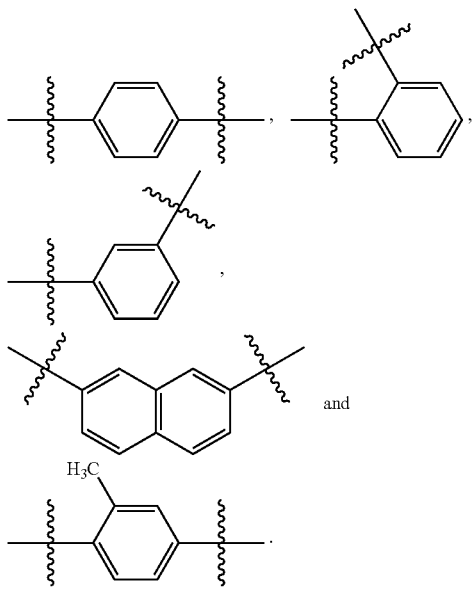

The term "substituted arenediyl" refers to a divalent group, wherein the arenediyl group is attached with two σ-bonds, with two aromatic carbon atoms as points of attachment, said carbon atoms forming part of one or more six-membered aromatic rings structure(s), wherein the ring atoms are all carbon, and wherein the divalent group further has at least one atom independently selected from the group consisting of N, O, F, Cl, Br, I, Si, P, and S.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "heteroarenediyl" when used without the "substituted" modifier refers to a divalent group, wherein the heteroarenediyl group is attached with two σ-bonds, with an aromatic carbon atom or nitrogen atom as the point of attachment, said carbon atom or nitrogen atom two aromatic atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of heteroarenediyl groups include:

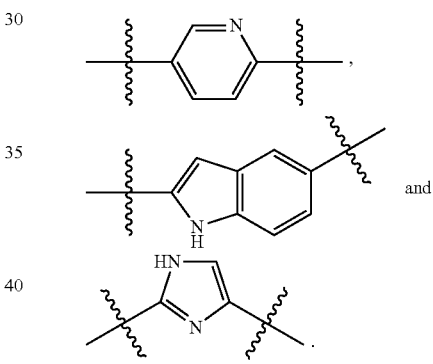

The term "substituted heteroarenediyl" refers to a divalent group, wherein the heteroarenediyl group is attached with two σ-bonds, with two aromatic carbon atoms as points of attachment, said carbon atoms forming part of one or more six-membered aromatic rings structure(s), wherein the ring atoms are all carbon, and wherein the divalent group further has at least one atom independently selected from the group consisting of N, O, F, Cl, Br, I, Si, P, and S.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$, —C(O)CH$_2$CH$_3$, —C(O)

CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —C(O)CH$_2$Cl, —CO$_2$H (carboxyl), —CO$_2$CH$_3$ (methylcarboxyl), —CO$_2$CH$_2$CH$_3$, —CO$_2$CH$_2$CH$_2$CH$_3$, —CO$_2$C$_6$H$_5$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl carbonyl" groups.

The term "alkylidene" when used without the "substituted" modifier refers to the divalent group =CRR', wherein the alkylidene group is attached with one σ-bond and one n-bond, in which R and R' are independently hydrogen, alkyl, or R and R' are taken together to represent alkanediyl. Non-limiting examples of alkylidene groups include: =CH$_2$, =CH(CH$_2$CH$_3$), and =C(CH$_3$)$_2$. The term "substituted alkylidene" refers to the group =CRR', wherein the alkylidene group is attached with one σ-bond and one n-bond, in which R and R' are independently hydrogen, alkyl, substituted alkyl, or R and R' are taken together to represent a substituted alkanediyl, provided that either one of R and R' is a substituted alkyl or R and R' are taken together to represent a substituted alkanediyl.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

In structures wherein stereochemistry is not explicitly indicated, it is assumed that either stereochemistry is considered and both isomers are claimed.

Any undefined valency on an atom of a structure shown in this application implicitly represents a hydrogen atom bonded to the atom.

The term "protecting group," as that term is used in the specification and/or claims, is used in the conventional chemical sense as a group, which reversibly renders unreactive a functional group under certain conditions of a desired reaction and is understood not to be H. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

Protecting groups include but are not limited to: alcohol protecting groups: acetoxy group, acetate (AC), β-methoxyethoxymethyl ether (MEM), methoxymethyl ether (MOM), p-methoxybenzyl ether (PMB), methylthiomethyl ether, pivaloyl (Piv), tetrahydropyran (THP), silyl ethers (including but not limited to trimethylsilyl (TMS), tert-butyldimethylsilyl (TBDMS), and triisopropylsilyl (TIPS) ethers), methyl ethers, and ethoxyethyl ethers (EE). Amine protecting groups: carbobenzyloxy (Cbz) group, p-methoxybenzyl carbonyl (Moz or MeOZ) group, tert-butyloxycarbonyl (BOC) group, 9-fluorenylmethyloxycarbonyl (FMOC) group, benzyl (Bn) group, p-methoxybenzyl (PMB), dimethoxybenzyl (DMPM), p-methoxyphenyl (PMP) group, tosyl (Ts) group, and other sulfonamides (Nosyl & Nps) groups. Carbonyl protecting groups: acetals, ketals, acylals, and dithianes. Carboxylic acid protecting groups: alkyl esters, aryl esters, silyl esters. Protection of terminal alkynes protected as propargyl alcohols in the Favorskii reaction. These and other considered protecting groups are described in the book on protecting groups by Wuts and Greene [14].

The term "leaving group," as that term is used in the specification and/or claims, is an atom or group (charged or uncharged) that becomes detached from an atom in what is considered to be the residual or main part of the substrate in a specified reaction.

Leaving groups include, but are not limited to: NH$_2$$^-$ (amine), CH$_3$O$^-$ (methoxy), HO$^-$ (hydroxyl), CH$_3$COO$^-$ (carboxylate), H$_2$O (water), F$^-$, Cl$^-$, Br$^-$, I$^-$, N$_3$$^-$ (azide), SCN$^-$ (thiocyanate), NO$_2$ (nitro), tosyl (Ts) groups, and protecting groups.

The term "reactant" refers to a reactive compound, including but not limited to a reactive compound which, upon reaction a functional group on a drug (e.g. the hydroxyl on propofol), generates a linker intermediate. A "linker intermediate" is chemically attached to the drug (e.g. propofol) and, upon further reaction(s), generates a linker as a product (which can be done in one or more steps). A "linker" connects components of a conjugate, such as the carbohydrate-drug conjugates described herein.

The term "effective," as that term is used in the specification and/or claims, means adequate to accomplish a desired, or hoped for result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As used herein, the term "pro-drug" refers to a pharmacological substance (drug) that is administered in an inactive (or significantly less active) form. Once administered, the pro-drug is metabolized in vivo into an active metabolite. The rationale behind the use of a pro-drug is generally for absorption, distribution, metabolism, and excretion (ADME) optimization. Pro-drugs are usually designed to improve oral bioavailability, with poor absorption from the gastrointestinal tract usually being the limiting factor. Additionally, the use of a pro-drug strategy increases the selectivity of the drug for its intended target.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002) [15]. Unless otherwise specifically stated, the present invention contemplates pharmaceutically acceptable salts of the considered pro-drugs.

As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

As used herein, "predominantly one anomer" means that a compound contains at least about 85% of one anomer, or more preferably at least about 90% of one anomer, or even more preferably at least about 95% of one anomer, or most preferably at least about 99% of one anomer. Similarly, the phrase "substantially free from other optical isomers" means that the composition contains at most about 15% of another anomer, more preferably at most about 10% of another anomer, even more preferably at most about 5% of another anomer, and most preferably at most about 1% of another anomer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

Enantiomers are compounds that individually have properties said to have "optical activity" and consist of molecules with at least one chiral center, almost always a carbon atom. If a particular compound is dextrorotary, its enantiomer will be levorotary, and vice-versa. In fact, the enantiomers will rotate polarized light the same number of degrees, but in opposite directions. "Dextrorotation" and "levorotation" (also spelled laevorotation) refer, respectively, to the properties of rotating plane polarized light clockwise (for dextrorotation) or counterclockwise (for levorotation). A compound with dextrorotation is called "dextrorotary," while a compound with levorotation is called "levorotary".

A standard measure of the degree to which a compound is dextrorotary or levorotary is the quantity called the "specific rotation" "[α]". Dextrorotary compounds have a positive specific rotation, while levorotary compounds have negative. Two enantiomers have equal and opposite specific rotations. A dextrorotary compound is prefixed "(+)-" or "d-". Likewise, a levorotary compound is often prefixed "(−)-" or "l-". These "d-" and "l-" prefixes should not be confused with the "D-" and "L-" prefixes based on the actual configuration of each enantiomer, with the version synthesized from naturally occurring (+)-compound being considered the D-form. A mixture of enantiomers of the compounds is prefixed "(±)-". An equal mixture of enantiomers of the compounds is considered "optically inactive".

The invention contemplates that for any stereocenter or axis of chirality for which stereochemistry has not been defined, that stereocenter or axis of chirality can be present in its R form, S form, or as a mixture of the R and S forms, including racemic and non-racemic mixtures.

The present invention contemplates the above-described compositions in "therapeutically effective amounts" or "pharmaceutically effective amounts", which means that amount which, when administered to a subject or patient for treating a disease, is sufficient to effect such treatment for the disease or to ameliorate one or more symptoms of a disease or condition (e.g. ameliorate pain).

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

"Subject" refers to any mammal, preferably a human patient, livestock, or domestic pet.

In a specific embodiment, the term "pharmaceutically acceptable" means approved by a regulatory agency of the federal or a state government or listed in the U.S. Pharmacopeia or other generally recognized pharmacopeia for use in animals, and more particularly in humans. In one embodiment, the formulations of the present invention contain other components than just the glycosylated drug, including but not limited to carriers. The term "carrier" refers to a diluent, adjuvant, excipient or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present compositions, if desired, can also contain minor amounts of wetting or emulsifying agents, or pH buffering agents.

Pharmaceutically acceptable sugars include but are not limited to sucrose, dextrose, maltose, galactose, rhamnose, and lactose. Pharmaceutically acceptable sugar alcohols include but are not limited to mannitol, xylitol, and sorbitol.

Abbreviations:

$C_0$—Initial concentration at time 0, extrapolated.
$t_{1/2}$—Half-life of the pro-drug analog.
$CL_p$—Estimate of total body clearance, $CL_p$=dose/$AUC_{inf}$
$Vd_{ss}$—Estimate of the volume of distribution; $Vd_{ss}$=dose/$AUC_{inf}$
$AUC_{last}$—Area under the curve of time versus concentration, to the last detected concentration
$AUC_{inf}$—Area under the curve of time versus concentration, with concentration extrapolated to infinity
$MRT_{inf}$—Mean Residence Time when the drug concentration profile is extrapolated to infinity.
LLOQ—Low limit of quantitation
n.d.—Not detected

EXPERIMENTAL

Due to the administration problems that propofol has, we decided to make glycosylated pro-drugs of propofol. It was considered that these analogs would have greater water solubility, and with the phenol glycosylated, the pain experienced by patients due to the drug's acidity would be mitigated. Initial attempts to directly glycosylate propofol under a variety of conditions failed, likely due to sterics imparted by the 2,6 di-isopropyl groups on the phenyl ring system (FIG. 1).

Figure 2:
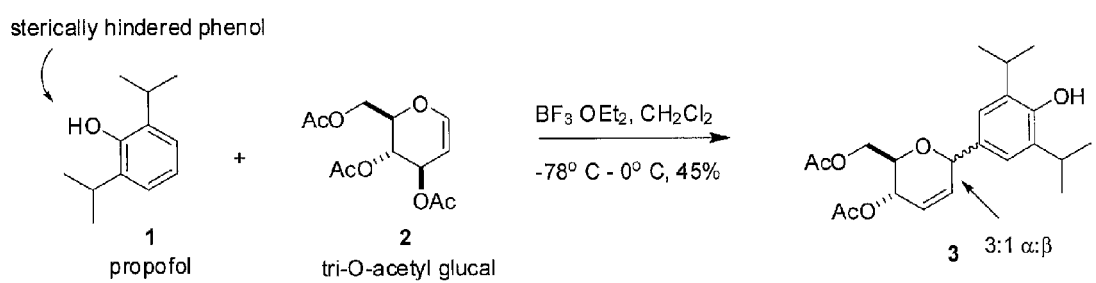
FIG. 2 shows a reaction scheme of employing less sterically demanding glycals such as tri-O-acetyl glucal which also failed, but in this case providing the unexpected C-glycosylated product at C-4 of propofol with an approximated 3:1 ratio of anomers.

Employing less sterically demanding glycals such as tri-O-acetyl glucal also failed, but in this case providing the unexpected C-glycosylated product at C-4 of propofol with an approximated 3:1 ratio of anomers (FIG. 2).

With the prospects of direct appearing to be poor, it was decided to design propofol analogs that would have the following attributes: 1) contain a carbohydrate and 2) would be connected to propofol using an agent that would be small in order to minimize the steric effects of propofol's isopropyl groups After in vivo enzymatic hydrolysis of the carbohydrate, the remaining moiety used to connect the carbohydrate to propofol would quickly eliminate itself, thus liberating propofol itself.

Figure 3:
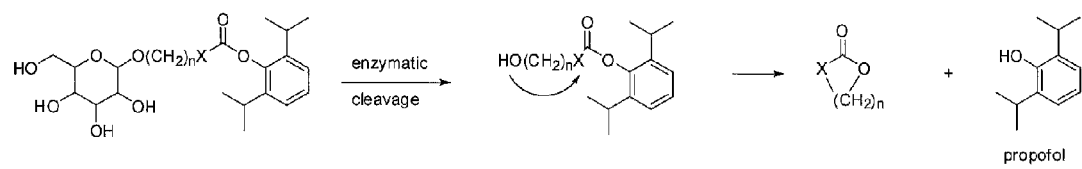
FIG. 3 shows how the design of the propofol pro-drug analogs release of propofol upon enzymatic cleavage of the carbohydrate.

A simple example of the design can be seen in FIG. 3. A variety of carbohydrates could be employed, and, after enzymatic hydrolysis of the carbohydrate, if n=2 or 3 and X=O or perhaps NH, propofol should be quickly liberated due to intramolecular cyclization.

Figure 4:
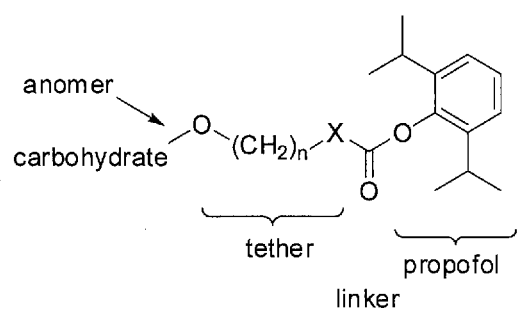
FIG. 4 shows the general structure of the propofol pro-drug analogs that can be prepared from the method from the basic design of the present invention. As shown, there are a number of different combinations that could be made by varying: 1) the carbohydrate (glucose, galactose, mannose, etc, and disaccharides such as maltose, lactose, etc), 2) the anomer (α or β), 3) the tether length (n), and 4) the type of linker; e.g. carbonate (X=O), thiocarbonate (X=S), carbamate (X=NH, or NR, where R=alkyl, aryl, etc). (Note: this is not meant to rule out branched tethers or branching from, for example, carbamates when X=NR).

Thus, a variety of analogs could be prepared from this basic design. As shown in FIG. 4, there are a number of different combinations that could be made by varying: 1) the carbohydrate (glucose, galactose, mannose, etc, and disaccharides such as maltose, lactose, etc), 2) the anomer ($\alpha$ or $\beta$), 3) the tether length (n), and 4) the type of linker; e.g. carbonate (X=O), thiocarbonate (X=S), carbamate (X=NH, or NR, where R=alkyl, aryl, etc). See FIG. 4. (Note: this is not meant to rule out branched tethers or branching from, for example, carbamates when X=NR).

Figure 5:
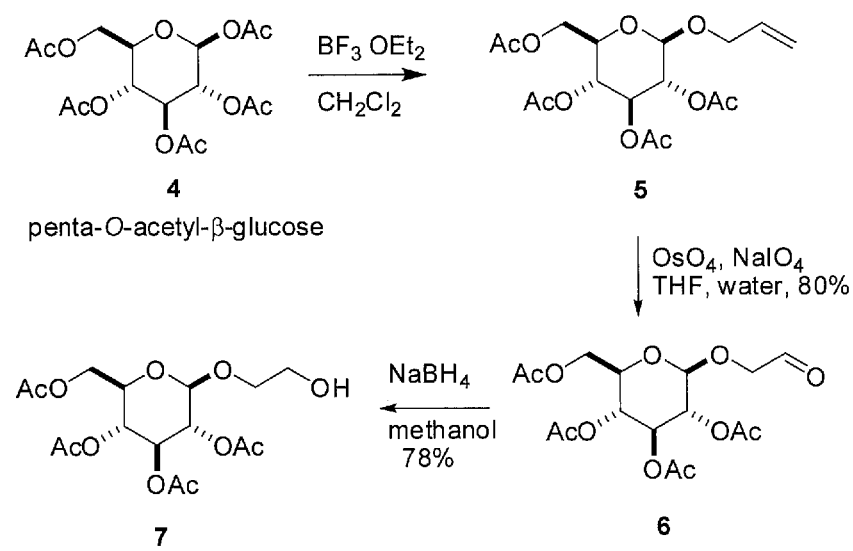
FIG. 5 shows the reaction scheme of the preparation of one of the analogs of the type described in FIG. 4, starting with the known preparation of 1-allyl tetra-O-acetyl-β-glucopyranoside 5. Oxidation of 5 to aldehyde 6, followed by reduction provided the requisite tethered ethyl alcohol (n=2 from FIG. 4) 7 (FIG. 5), all in good yield.

Initial attempt to prepare analogs of the type described above (in FIG. 4) started with the known preparation of 1-allyl tetra-O-acetyl-$\beta$-glucopyranoside 5 (Tronchet, J. M. J.; Zsely, M.; Geoffroy, M. Carbohydr. Res. 1995, 275, 245-258) [16]. Oxidation of 5 to aldehyde 6, followed by reduction provided the requisite tethered ethyl alcohol (n=2 from FIG. 4) 7 (FIG. 5), all in good yield.

Figure 6:
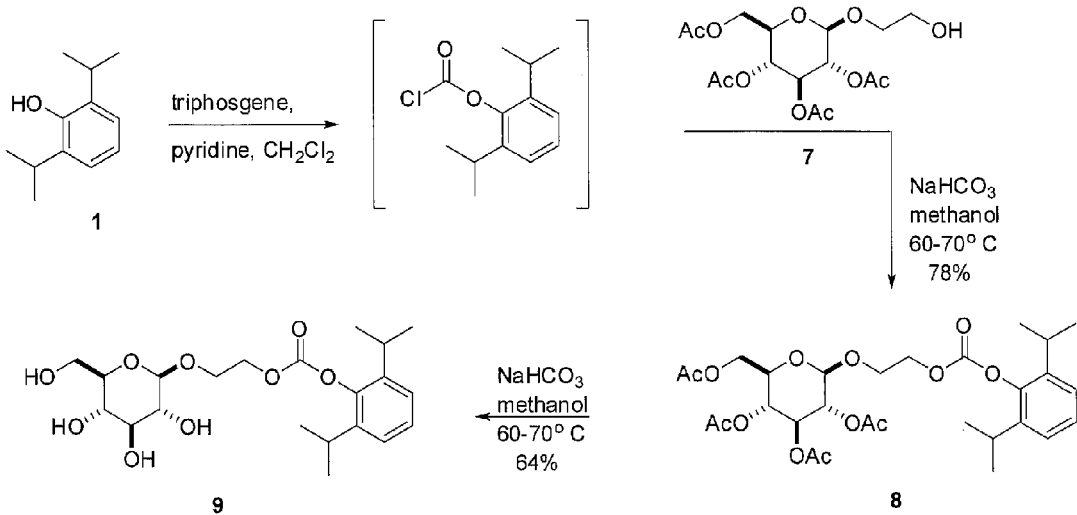
FIG. 6 shows a reaction scheme wherein propofol was attached to tethered carbohydrate 7 by first treating propofol with triphosgene in pyridine and $CH_2Cl_2$ to form, in situ, the chloroformate of propofol. Addition of tethered carbohydrate 7 cleanly provided carbonate 8 in very good yield. Hydrolysis of the acetates while leaving the carbonate intact could be accomplished by dissolving carbonate 8 in methanol, addition of anhydrous $NaHCO_3$, and warming the mixture to near reflux for several hours.

Propofol was attached to tethered carbohydrate 7 by first treating propofol with triphosgene (which is a carbonate) in pyridine and $CH_2Cl_2$ to form, in situ, the chloroformate of propofol (FIG. 6). Addition of tethered carbohydrate 7 cleanly provided carbonate 8 in very good yield. Hydrolysis of the acetates while leaving the carbonate intact could be accomplished by dissolving carbonate 8 in methanol, addition of anhydrous $NaHCO_3$, and warming the mixture to near reflux for several hours. It should be noted that $NaHCO_3$ typically contains 2-5% $Na_2CO_3$ as an impurity and that this might be responsible for the hydrolysis of the acetates.

Figure 7:
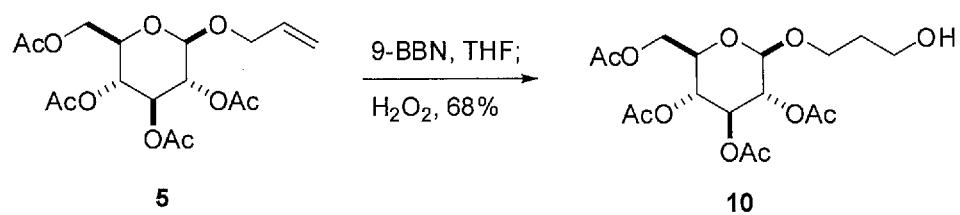
FIG. 7 shows a reaction scheme of the present invention wherein the propyl version of analog 9 could be prepared by first preparing the propyl version of 7, 1-(propan-3-ol) tetra-O-acetyl-β-d-glucopyranose 10, by hydroboration of alkene 5, followed by oxidative work up with hydrogen peroxide.

The propyl version of analog 9 could be prepared by first preparing the propyl version of 7, 1-(propan-3-ol)tetra-O-acetyl-$\beta$-D-glucopyranose 10, by hydroboration of alkene 5, followed by oxidative work up with hydrogen peroxide (FIG. 7).

Figure 8:
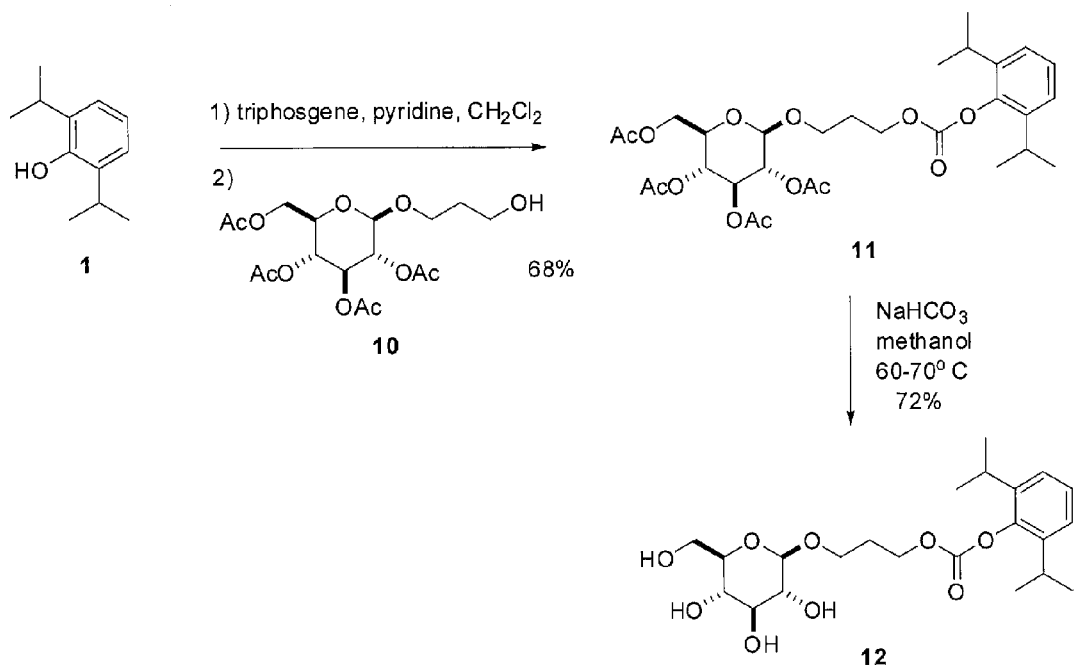
FIG. 8 shows a reaction scheme of the present invention wherein the ethyl tethered analog 9, the chloroformate of propofol was made in situ, followed by addition of 1-(propan-3-ol)-tetraacetyl glucopyranose 10 to form the penultimate carbonate 11 smoothly and in good yield. Removal of the protecting acetates was again uneventful with $NaHCO_3$ in methanol, providing β carbonate analog 12 in good yield.

In a similar vein for the ethyl tethered analog 9, the chloroformate of propofol was made in situ, followed by addition of 1-(propan-3-ol)-tetra-O-acetyl-$\beta$-D-glucopyranose 10 to form the penultimate carbonate 11 smoothly and in good yield (FIG. 8). Removal of the protecting acetates was again uneventful with $NaHCO_3$ in methanol, providing $\beta$ carbonate analog 12 in good yield.

Figure 9:
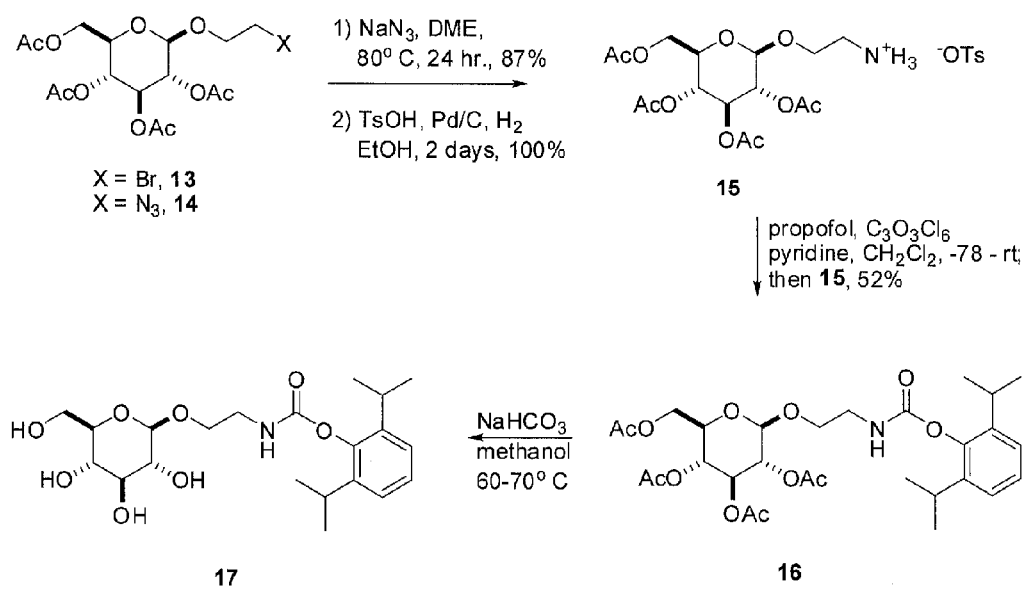
FIG. 9 shows a reaction scheme of the present invention wherein carbamate analogs can be made using a similar approach.

Carbamate analogs can be made using a similar approach. 1-(2-bromoethyl)-tetra-O-acetyl-$\beta$-D-glucopyranose 13 can be converted into azide 14 in excellent yield, which in turn can be reduced to ammonium tosylate salt 15 by hydrogenation (FIG. 9). This salt, used without purification, can be converted to propofol carbamate 16 in the same manner as with the carbonates described previously. As with the tetraacetyl carbonates 8 and 11, hydrolysis of the acetates of 16 with NaHCO₃ in methanol smoothly provides the target propofol carbamate analog 17 in good yield.

Figure 10:
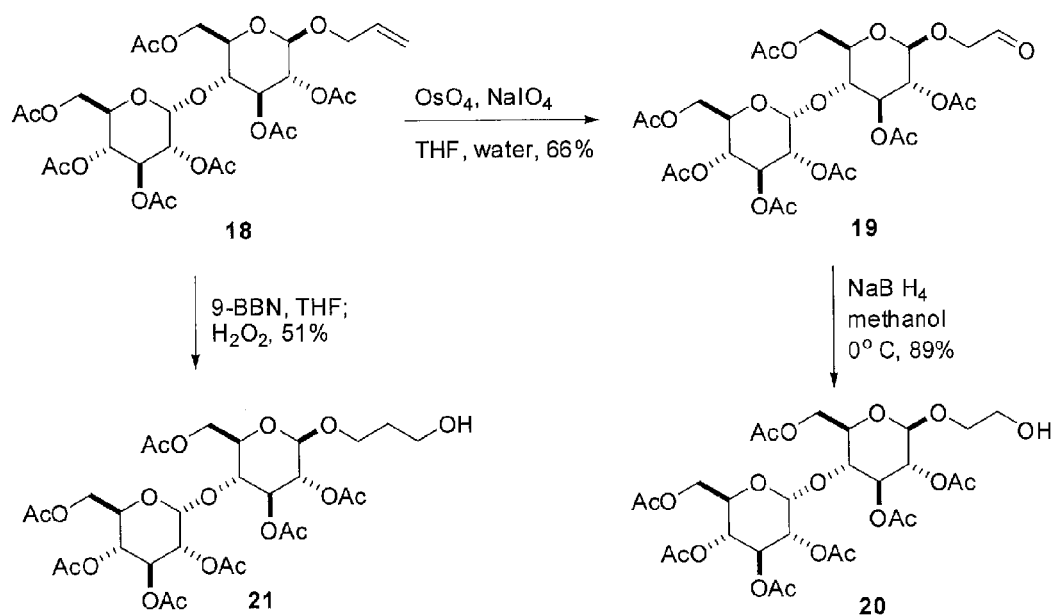
FIG. 10 shows a reaction scheme of the present invention wherein disaccharide versions 20 and 21 of tethered monosaccharides 9 and 12, respectively, could be synthesized.

Disaccharide versions of the propofol carbonate analogs 9 and 12 described above could similarly be made by starting with 1-allyl hepta-O-acetyl-β-maltose 18 (FIG. 10) to make the requisite 1-(ethan-2-ol) heptaacetyl maltose 20 and 1-(propan-3-ol) heptaacetyl maltose 21.

Figure 11:
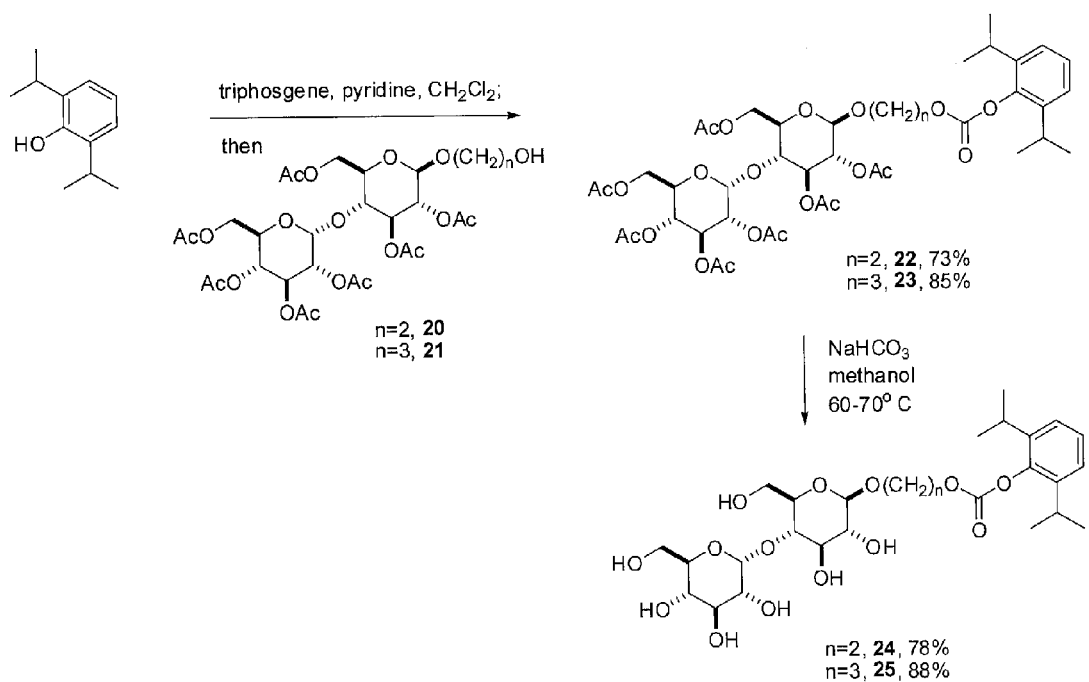
FIG. 11 shows a reaction scheme of the present invention wherein formation of the chloroformate of propofol preceded treatment with either alcohol 20 or 21 provided carbonates 22 and 23, respectively, which, after hydrolysis of the acetates, provided the final target carbonates 24 and 25, respectively.

Preparation of the tethered disaccharide analogs of propofol were prepared in the same manner as the monosaccharide analogs 9 and 12 described above. Formation of the chloroformate of propofol preceded treatment with either alcohol 20 or 21 to provide carbonates 22 or 23, respectively (FIG. 11). Again, hydrolysis of the protecting acetates was accomplished with NaHCO₃ in methanol at elevated temperatures to provide the desired disaccharide analogs of propofol 24 and 25 in good yield.

Figure 12:
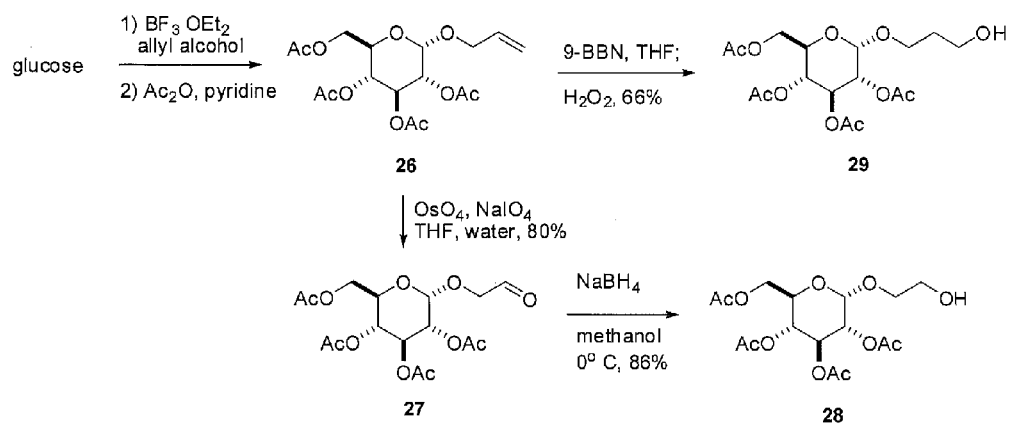
FIG. 12 shows a reaction scheme of the present invention wherein the α analog versions 28 and 29 of β tethered sugars 7 and 9 can also be prepared by this approach with a few subtle changes.

Finally, all of the tethered glycosylated analogs of propofol have all been of the β configuration at the carbohydrate; a analogs can also be prepared by this approach with a few subtle changes (FIG. 12). Formation of the allyl functionality at C-1 of glucose with allyl alcohol and acid prior to acylation is known to provide predominantly the α anomer. Acylation provides key allyl intermediate 26 which could be obtained isomerically pure (Tronchet et al.) [16]. As with its β isomer, allyl intermediate could be conveniently converted into 1-(2-hydroxyethyl) glucopyranose analog 28 in two steps or 1-(3-hydroxypropyl) glucopyranose 29 in a single step.

Figure 13:
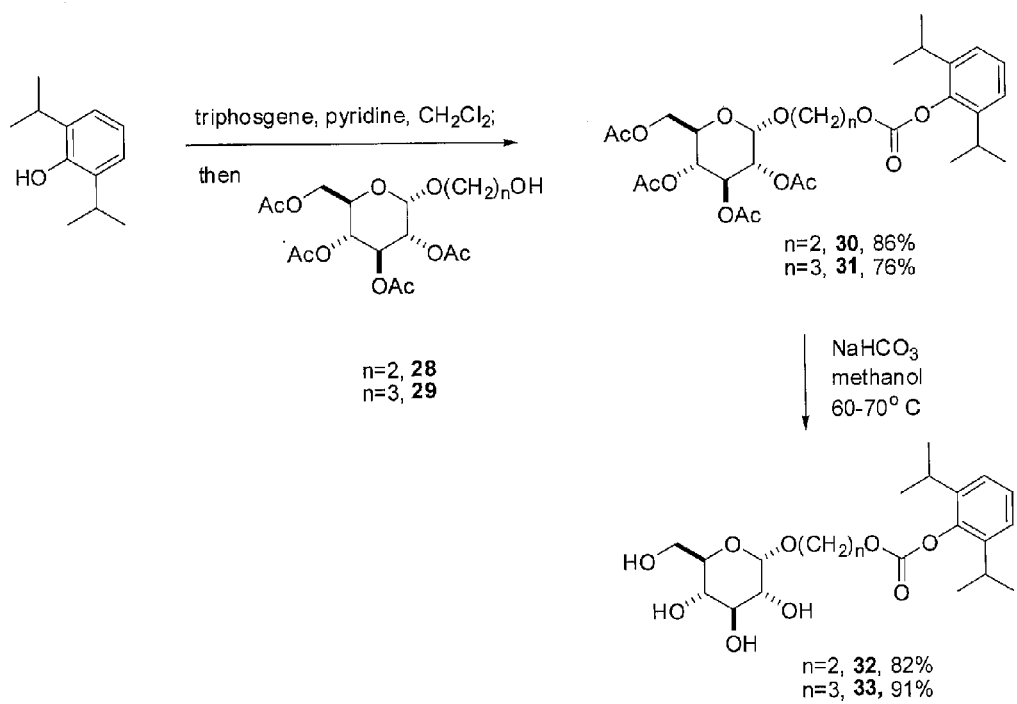
FIG. 13 shows a reaction scheme of the present invention wherein formation of the carbonates from tethered monosaccharides 30 and 31 proved uneventful, and hydrolysis with $NaHCO_3$ in methanol provided the final, a analogs 32 and 33 in very good yield.

Formation of the carbonates 30 and 31 from tethered monosaccharides 28 and 29 proved uneventful (FIG. 13), and hydrolysis with NaHCO₃ in methanol provided the final, α analogs 32 and 33 in very good yield.

Table 3 shows the structure of each of the propofol analogs prepared and the solubility of each in D₂O using ¹H NMR with 3-(trimethylsilyl)-1-propanesulfonic acid sodium salt (DSS) as an internal standard. Unfortunately, while preparing saturated solutions, all but two of the analogs (17 and 33) including propofol itself provided solutions that were not filterable. Thus the soapy-like solutions obtained were diluted until opalescent and diluted further until the opalescence visually disappeared. Qualitatively, inspection of the solubility data shows that carbamate functionality serves as a detriment as compared to its corresponding carbonate; the shorter ethyl tether is more beneficial than its propyl counterpart (9 vs. 12 and 32 vs. 33) and that the α configuration seems to have a better water solubility over its β counterpart (9 vs. 32; 12 vs. 33).

During the pharmacokinetics study on rats, a number of encouraging observations were made of the rats' behavior (Table 4). The control, propofol, was administered i.m. at 30 mg/kg (0.168 mM/kg) in a 5% cremaphor solution. For all of the carbonate analogs, the rats were all soporous between 3 and 7 minutes post the 10 minute infusion and recovered 26-35 minutes post infusion, comparing very favorably to propofol at twice the molar concentration. Due to its poor water solubility, carbamate 17 had to have a cosolvent (10% tween80) and poor results were obtained for this analog in its vehicle.

The results from the pharmacokinetics details of the study on male Sprague-Dawley rats (Table 5 A&B, Table 6, and Table 7) show the concentration of prodrug in the rats' blood (Table 6) and the concentration of propofol (Table 7) over time. It is apparent that the carbonate analogs 9, 12, 24, 25, 32 and 33 all act as very efficient pro-drugs, releasing the propofol in a matter of minutes after infusion.

In one embodiment, the invention relates to methods of synthesizing derivatives of propofol.

The additional work described below and in the experimental section, were all done once and is thus unoptimized. The yields stated should be considered as a minimum.

Figure 14:
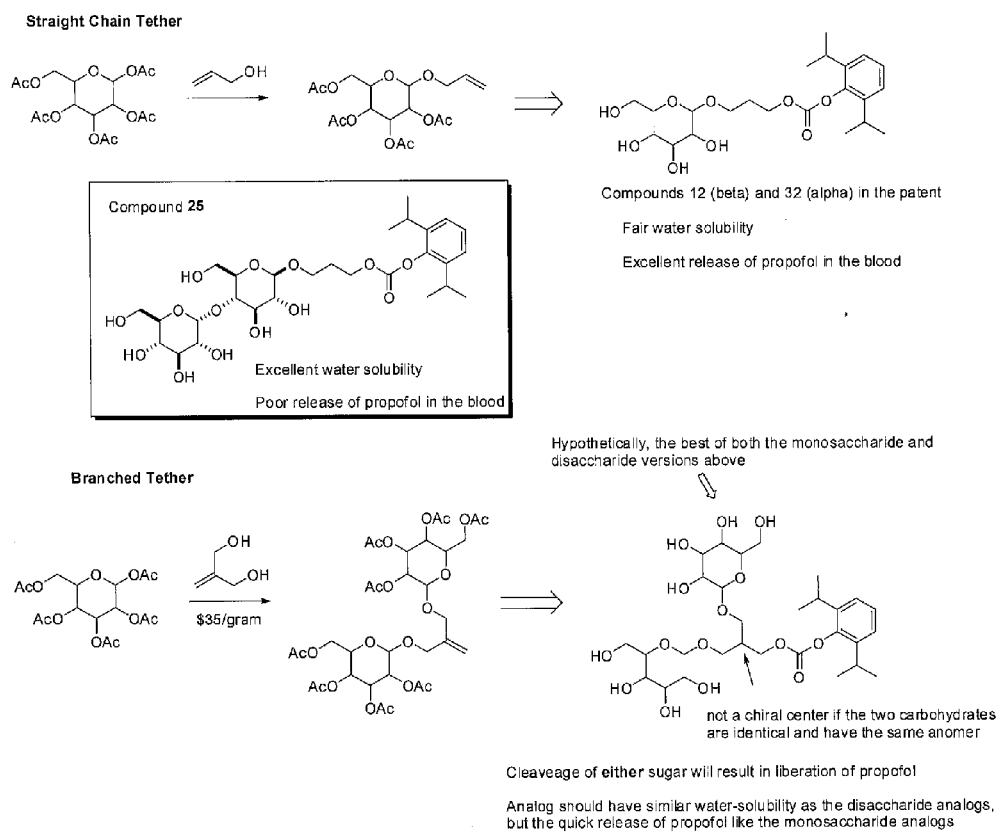
FIG. 14 shows a schematic comparing a single carbohydrate tether and the branched chain tether embodiments of the current invention.

FIG. 14 shows a schematic comparing a single carbohydrate tether and the branched chain tether embodiments of the current invention.

Figure 15:
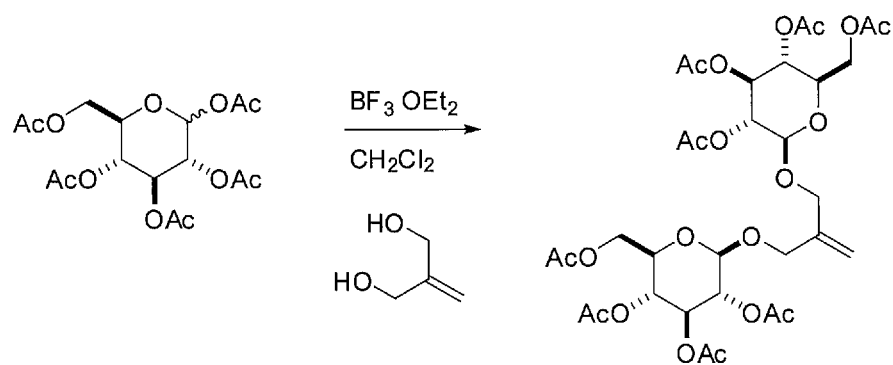
FIG. 15 shows the bis-glycosylation of 2-methylene 1,3-propane diol under acidic conditions similar to those described herein for allyl alcohol should provide the bis adduct.

The preparation of branched-tethered analogs of this type should be fairly straight-forward by applying the methodology already described. Bis-glycosylation of 2-methylene 1,3-propane diol under acidic conditions similar to those described herein for allyl alcohol should provide the bis adduct shown in FIG. 15.

Figure 16:
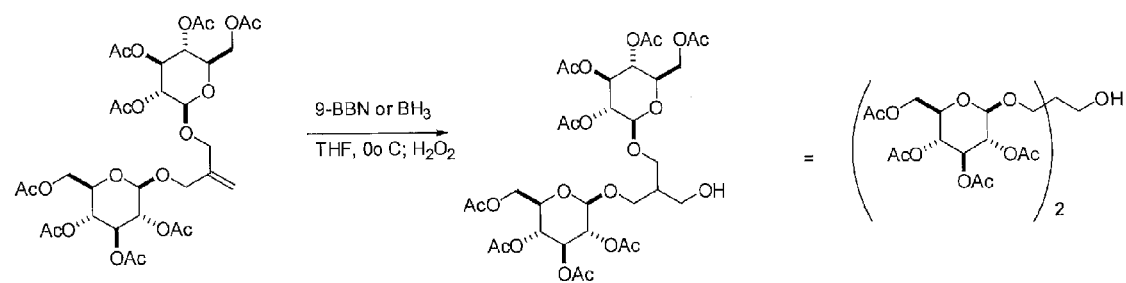
FIG. 16 shows the case for ally alcohol intermediates set up to provide tethered analogs of two different lengths. Hydroboration under similar conditions as described herein, followed by oxidative work-up should provide the longer of the two branched tethered bis-glycosylates

As in the case for ally alcohol, this intermediate is set up to provide tethered analogs of two different lengths. Hydroboration under similar conditions as described herein, followed by oxidative work-up should provide the longer of the two branched tethered bis-glycosylates FIG. 16.

Figure 17:
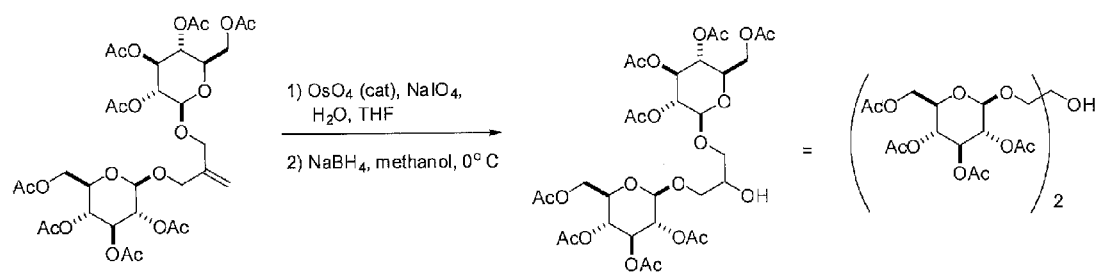
FIG. 17 shows oxidative cleavage of the alkene (with ozone or with $OsO_4/NaIO_4$) to form an intermediate ketone, followed by reduction (with, for example, $NaBH_4$ in methanol) to a secondary hydroxyl should smoothly provide the shorter of the two tethered examples shown.

Alternatively, oxidative cleavage of the alkene (with ozone or with OsO₄/NaIO₄, as shown below) to form an intermediate ketone, followed by reduction (with, for example, NaBH₄ in methanol) to a secondary hydroxyl should smoothly provide the shorter of the two tethered examples shown in FIG. 17.

Figure 18:
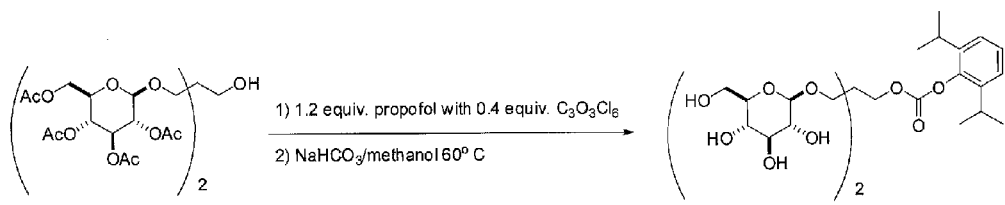
FIG. 18 shows the preparation of the propofol carbonates from the branched tethered carbohydrates.
Figure 18:
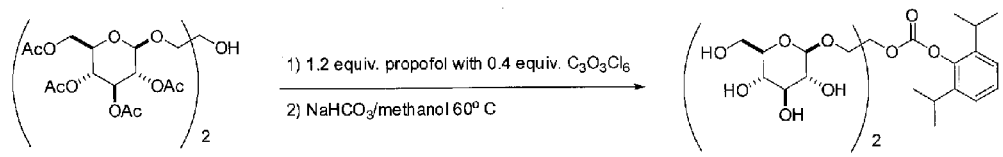

Finally, preparation of the propofol carbonates from the branched tethered carbohydrates should proceed under similar conditions already described. In situ preparation of the chloroformate of propofol, followed by addition of the branched tethered carbohydrate should provide the penultimate corresponding carbonates of propofol. Removal of the acetate protecting groups on the carbohydrate under mild conditions (in this case with sodium bicarbonate in warm methanol) should provide the target branched tethered analogs, as shown in FIG. 18.

EXAMPLES

The following examples are provided in order to demonstrate and further illustrate certain preferred embodiments and aspects of the present invention and are not to be construed as limiting the scope thereof.

General.

¹H and ¹³C NMR spectra were taken on a Varian Mercury 300 or 400 MHz spectrometer. Chemical shifts are reported in parts per million (ppm) from an internal standard; either 2,2-dimethyl-2-silapentane-5-sulfonate sodium salt (DSS, 0.00 ppm, used for D₂O), tetramethylsilane (TMS, 0.00 ppm for all other solvents), or from the solvent residual peak (CDCl₃, 7.26 ppm in ¹H NMR, 77.23 ppm in ¹³C NMR; acetone, 2.05 ppm in ¹H, 29.84 ppm in ¹³C; DMSO, 2.50 ppm in ¹H, 39.52 ppm in ¹³C ppm; D₂O 4.79 ppm in ¹H; methanol 3.31 ppm in ¹H, 49.00 in ¹³C) [Gottlieb, H. E.; Kotlyar, V.; Nudelman, A. J. Org. Chem., 1997, 62, 7512-7515] as an internal standard [17]. ¹H NMR is reported in the following manner: chemical shift; multiplicity (s=singlet, d=doublet, t=triplet, q=quartet, m=multiplet, br=broadened, dd=doublet of doublets, etc.); coupling constant (in order of the multiplicity). Coupling constants (J values) are given in hertz (Hz). The multiplicity (from attached protons) of each ¹³C chemical shift is reported as follows, q (a methyl carbon, i.e., CH₃), t (CH₂), d (CH), and s (quarternary carbon). All chemicals were purchased from Sigma-Aldrich; all solvents were purchased from Pharmco-AAPER. THF was dried over sodium benzophenone ketyl and distilled, CH₂Cl₂ was dried over CaSO₄ and distilled. All reactions were monitored by thinlayer chromatography on silica gel 60 F254 (Merck); detection was carried out by UV and by charring after spraying with a solution made from 4.7 g Ceric ammonium sulfate and 5.6 mL concentrated sulfuric acid diluted to 100 mL. For flash column chromatography, silica gel 60, 230-400 mesh from Mallinckrodt was used. Optical rotations were obtained using a Bellingham+Stanley ADP-220 POLARIMETER. LC-MS experiments were performed using an Agilent 1600 Series LC/MS ion-trap mass spectrometer coupled to an Agilent 1200 Series HPLC system. The mass spectrometer was operated with the electrospray ionization (ESI) source in the positive ion mode. The HPLC system was equipped with an Eclipse XDB-C18 column (Agilent; ID 4.6 mm, length 50 mm, particle size 1.8 M). Solvents used as eluants were: water with 0.2% formic acid and acetonitrile with 0.2% formic acid.

Example 1

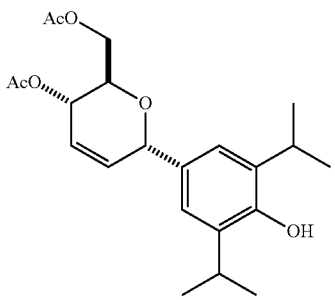

3

Propofol 1 (0.430 g) and tri-O-acetyl glucal (0.720 g) were dissolved in CH$_2$Cl$_2$, the solution cooled to −78° C. and BF$_3$OEt$_2$ (0.025 g) was added. The solution was stirred for 1 hr before slowly warming to 0° C. over the course of another hr. The reaction was quenched with 2 mL saturated NaHCO$_3$ and the reaction diluted with CH$_2$Cl$_2$ (50 mL) the aqueous discarded, the organic washed once with NaHCO$_3$ (50 mL), brine (25 mL), dried (Na$_2$SO$_4$), filtered, and concentrated. The crude was then purified by silica gel column chromatography (25% ethyl acetate/hexanes) to provide 0.390 g (41%) 3 as a yellow syrup. $^1$H NMR (300 MHz, CDCl$_3$) δ 1.26 (d, J=6.9 Hz, 12H), 2.07 (s, 3H), 2.12 (s, 3H), 3.15 (qq, J=6.9, 6.9 Hz, 2H), 3.93 (ddd, J=2.6, 6.1, 9.2 Hz, 1H), 4.18 (1H) and 4.28 (1H) (ABq, J$_{AB}$=12.0 Hz, the peaks at 4.18 and 4.28 are further split into d, J=6.1 Hz and 2.6 Hz, respectively), 5.04 (s, 1H, OH), 5.13 (br s, 1H), 5.44 (ddd, J=1.4, 1.4, 9.2 Hz, 1H), 5.83 (1H) and 5.93 (1H) (ABq, J$_{AB}$=10.2 Hz; the peaks at 5.83 and 5.93 are further split into dd, J=1.4, 2.2 Hz and 1.4, 1.7 Hz, respectively), 7.00 (s, 2H); $^{13}$C NMR (75.4 MHz, CDCl$_3$) δ 21.1 (q), 21.3 (q), 22.9 (q, 4C), 27.4 (d, 2C), 64.1 (t), 65.9 (d), 75.0 (d), 78.1 (d), 123.2 (d), 124.8 (d), 131.7 (s), 133.4 (d, 2C), 134.0 (s, 2C), 150.5 (s), 170.7 (s), 171.3 (s).

Example 2

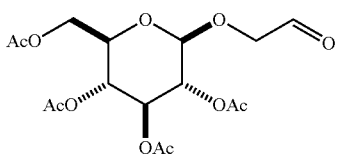

6

1-Allyl 2,3,4,6-tetra-O-acetyl-β-D-glucopyranoside 5 (2.66 g) was dissolved in 30 mL THF and mL water and 0.871 g (0.02 equivalents) 4% OsO$_4$ solution was added. The reaction mixture was stirred at room temperature for 45 min., after which NaIO$_4$ (2.93 g, 2 equivalents, dissolved in a minimum amount of water) was added over the course of 20 min. The reaction was stirred for another 1.5 hrs, and was then poured into 30 mL CH$_2$Cl$_2$, and the solution washed once with water (30 mL) and brine (20 mL). The organic layer was then dried (Na$_2$SO$_4$), filtered and concentrated, and the resultant syrup purified by silica gel column chromatography (gradient 1:1 ethyl acetate/hexanes to ethyl acetate) to provide 2.13 g (80%) 1-(2'-oxyethyl) 2,3,4,6-tetra-O-acetyl-β-D-glucopyranoside 6 as a colorless oil that solidified upon standing. [α]$^{18}$$_D$ −22.7° (c 1.11, CH$_2$Cl$_2$); $^1$H NMR (300 MHz, CDCl$_3$) δ 2.02 (s, 3H), 2.04 (s, 3H), 2.09 (s, 6H), 3.73 (ddd, J=2.2, 5.0, 9.9 Hz, 1H), 4.09-4.32 (m, 4H), 4.60 (d, J=7.7 Hz, 1H), 5.09 (dd, J=9.4, 9.9 Hz, 1H), 5.10 (dd, J=7.7, 9.4 Hz, 1H), 5.24 (dd, J=9.4, 9.4 Hz, 1H), 9.68 (s, 1H); $^{13}$C NMR (75.4 MHz, CDCl$_3$) δ 20.7 (q), 20.7 (q), 20.8 (q, 2C), 61.8 (t), 68.4 (d), 71.0 (d), 72.2 (d), 72.6 (d), 74.3 (t), 101.1 (d), 169.6 (s), 169.7 (s), 170.4 (s), 170.8 (s), 200.1 (d).

Example 3

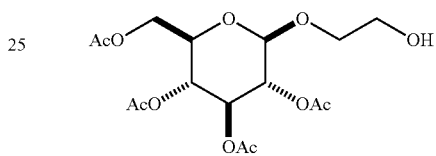

7

1-(2'-oxyethyl) 2,3,4,6-tetra-O-acetyl-β-D-glucopyranoside 6 (1.80 g) was dissolved in 20 mL methanol and cooled down to 0° C. Sodium borohydride (0.210 g, 1.2 equivalents) was then added over the course of 30 minutes, after which the reaction appeared to be complete as judged by TLC. Acetic acid (1 mL) was then added and the solvent removed under reduced pressure. The residue was then dissolved in 50 mL CH$_2$Cl$_2$ and 50 mL water, the aqueous discarded, and the organic washed once with 20 mL brine. The organic layer was then dried (Na$_2$SO$_4$), filtered, and concentrated. The residue obtained was then purified by silica gel column chromatography (gradient 1:1 ethyl acetate/hexanes to ethyl acetate) to provide 1.42 g (78%) 1-(ethan-2'-ol)-2,3,4,6-tetra-O-acetyl-β-D-glucopyranoside 7 as a colorless foam. [α]$^{20}$$_D$ −7.0° (c 1.00, CH$_2$Cl$_2$); $^1$H NMR (400 MHz, CDCl$_3$) δ 2.01 (s, 3H), 2.04 (s, 3H), 2.06 (s, 3H), 2.10 (s, 3H), 2.45 (br s, 1H, OH), 3.85 (dd, J=Hz, 1H), 4.20 (app. d, J=4.1 Hz, 2H), 4.55 (d, J=7.8 Hz, 1H), 5.02 (dd, J=7.8, 9.6 Hz, 1H), 5.07 (dd, J=9.6, 9.9 Hz, 1H), 5.23 (dd, J=9.6, 9.6 Hz, 1H); $^{13}$C NMR (100.6 MHz, CDCl$_3$) δ 20.8 (q, 4C), 62.1 (t), 62.2 (t), 68.5 (d), 71.5 (d), 72.0 (d), 72.8 (d), 73.2 (t), 101.6 (d), 169.6 (s), 169.7 (s), 170.4 (s), 170.8 (s).

Example 4

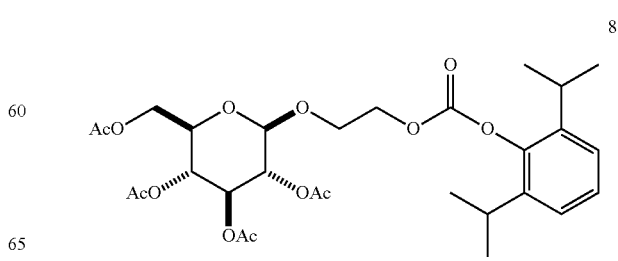

8

Triphosgene (0.416 g) was dissolved in 3 mL CH$_2$Cl$_2$ and cooled to −78° C. A solution of propofol (0.812 g), pyridine (1.661 g) and CH$_2$Cl$_2$ (2 mL) was prepared and added to the triphosgene solution. The reaction mixture was then slowly warmed to room temperature and stirred for 30 min. The mixture was then cooled back down to −78° C., and 1-(ethan-2'-ol)-2,3,4,6-tetra-O-acetyl-β-D-glucopyranoside 7 (1.100 g) dissolved in 3 mL CH$_2$Cl$_2$ was added. The reaction mixture was then warmed to room temperature and stirred for 2 hrs. The reaction mixture was then poured into 50 mL CH$_2$Cl$_2$ and washed once each with 5% HCl (50 mL), saturated CuSO$_4$ (25 mL), water (25 mL), NaHCO$_3$ (25 mL) and brine. The organic layer was then dried (Na$_2$SO$_4$), filtered, concentrated and resultant oil purified by silica gel column chromatography (gradient 10% acetone in hexanes to 30% acetone) to provide 1.63 g (78%)

1-((2',6'-diisopropylphenoxy)carbonyloxy)ethyl-2,3,4,6-tetra-O-acetyl-β-D-glucopyranoside 8 as a colorless foam. $[\alpha]^{21}_D$-13.3° (c 1.02, CH$_2$Cl$_2$); $^1$H NMR (400 MHz, CDCl$_3$) δ 1.22 (d, J=7.0 Hz, 12H), 2.02 (s, 3H), 2.04 (s, 3H), 2.07 (s, 3H), 2.09 (s, 3H), 3.01 (qq, J=7.0, 7.0 Hz, 2H), 3.71 (ddd, J=2.3, 4.8, 9.5 Hz, 1H), 3.87 (ddd, J=4.0, 7.3, 11.3 Hz, 1H), 4.11 (ddd, J=3.6, 7.9, 11.3 Hz, 1H), 4.15 (1H) and 4.28 (1H) (ABq, J$_{AB}$=12.5 Hz; the peaks at 4.15 are further split into d, J=2.3 Hz, the peaks at 4.28 are further split into d, J=4.8 Hz), 4.34-4.44 (m, 2H), 4.57 (d, J=8.1 Hz, 1H), 5.04 (dd, J=9.5, 9.9 Hz, 1H), 5.22 (dd, J=9.5, 9.9 Hz, 1H), 7.15 (d, J=8.6 Hz, 1H), 7.16 (d, J=6.4 Hz, 1H), 7.23 (dd, J=6.4, 8.6 Hz, 1H); $^1$H NMR (300 MHz, d$_4$-methanol) δ 1.21 (d, J=6.9 Hz, 12H), 1.97 (s, 3H), 2.01 (s, 3H), 2.03 (s, 3H), 2.05 (s, 3H), 3.01 (qq, J=6.9 Hz, 2H), 3.84 (m, 2H), 4.04-4.11 (m, 2H), 4.15 (1H) and 4.28 (1H) (ABq, J$_{AB}$=12.4 Hz; the peaks at 4.15 are further split into d, J=2.5 Hz, the peaks at 4.28 are further split into d, J=4.7 Hz), 4.36-4.74 (m, 2H), 4.72 (d, J=8.1 Hz, 1H), 4.93 (dd, J=8.1, 9.6 Hz, 1H), 5.04 (dd, J=9.6, 9.9 Hz, 1H), 5.26 (dd, J=9.6, 9.9 Hz, 1H), 7.16-7.25 (m, 3H); $^{13}$C NMR (75.5 MHz, CDCl$_3$) δ 20.6 (q), 20.7 (q), 20.7 (q), 20.8 (q), 23.4 (q, 4C), 27.4 (d, 2C), 61.9 (t), 67.3 (t), 67.5 (t), 68.4 (d), 71.1 (d), 72.0 (d), 72.8 (d), 101.0 (d), 124.2 (d, 2C), 127.0 (d), 140.5 (s, 2C), 145.7 (s), 153.8 (s), 169.5 (s, 2C), 170.3 (s), 170.7 (s).

Example 5

9

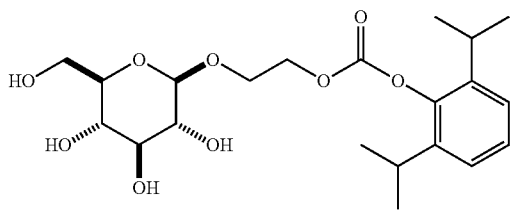

1-((2',6'-Diisopropylphenoxy)carbonyloxy)ethyl-2,3,4,6-tetra-O-acetyl-β-D-glucopyranoside 8 (1.400 g) was dissolved in 10 mL methanol and 0.080 g NaHCO$_3$ added. The solution was warmed to 50-60° C. and the progress of the reaction monitored by TLC. After about 2 hrs, the reaction was complete, the reaction cooled to room temperature, and then passed through a short column packed with DOWEX CCR-3 weakly acidic ion exchange resin. The solvent was then removed under reduced pressure and the residue purified by silica gel column chromatography (gradient 2% methanol in CH$_2$Cl$_2$ to 10% methanol) to provide 0.645 g (64%) 1-((2',6'-diisopropylphenoxy)carbonyloxy)ethyl-β-D-glucopyranoside 9 as a colorless foam.

$[\alpha]^{20}_D$-9.7° (c 1.03, acetone); $^1$H NMR (400 MHz, D$_2$O) δ 1.18 (d, J=6.9 Hz, 12H), 3.02 (qq, J=6.9, 6.9 Hz, 2H), 3.31 (dd, J=8.4, 8.8 Hz, 1H), 3.39 (dd, J=8.8, 9.5 Hz, 1H), 3.44 (m, 1H), 3.50 (dd, J=8.8, 9.5 Hz, 1H), 3.73 (1H) and 3.92 (1H) (ABq, J$_{AB}$=11.5 Hz; the peaks at 3.73 are further split into d, J=5.9 Hz), 4.01 (ddd, J=2.2, 5.9, 12.5 Hz, 1H), 4.19 (ddd, J=2.6, 5.7, 12.5 Hz, 1H), 4.48-4.58 (m, 2H), 4.51 (d, J=7.7 Hz, 1H), 7.31-7.38 (m, 3H); $^{13}$C NMR (100.6 MHz, D$_2$O) δ 25.3 (q, 4C), 29.7 (d, 2C), 57.1 (t), 63.5 (t), 70.1 (t), 71.4 (d), 72.4 (d), 75.8 (d), 78.4 (d), 78.7 (d), 105.1 (d), 127.4 (d, 2C), 130.6 (d), 143.7 (s, 2C), 147.6 (s), 157.7 (s); LC-MS (ESI): m/z (%) 446.3 (100, M$^+$+H$_2$O), 428.2 (17, M$^+$), 267.2 (56, iPr$_2$ArOCO$_2$CH$_2$CH$_2$OH+1), 225.1 (36, C$_6$H$_{11}$O$_6$CH$_2$CH$_2$OH+1).

Example 6

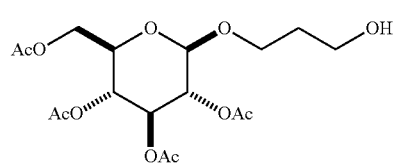

10

1-Allyl 2,3,4,6-tetra-O-acetyl-β-D-glucopyranoside (5, 3.70 g) was dissolved in 40 mL THF and cooled to 0° C. 9-BBN (16.6 mL of 0.5 M solution, 1.5 equivalents) was then added, and the solution was stirred at 0° C. for 1 hr, and stirred for an additional hr at room temperature. The solution was cooled back down to 0° C., and H$_2$O$_2$ (15 mL 30% solution) added over the course of min. The solution was then warmed to room temperature and stirred for 1 hr. The reaction mixture was then poured into 150 mL CH$_2$Cl$_2$ and washed with water (100 mL) and brine (50 mL), dried (Na$_2$SO$_4$), filtered and concentrated. The resultant oil was then purified by silica gel column chromatography (gradient 1:1 ethyl acetate/hexanes to ethyl acetate) to provide 1.52 g (68%) 1-(propan-3'-ol)-2,3,4,6-tetra-O-acetyl-β-D-glucopyranoside 10 as a colorless foam. $[\alpha]^{20}_D$-19.2° (c 0.52, CH$_2$Cl$_2$); $^1$H NMR (400 MHz, CDCl$_3$) δ 1.80-1.92 (m, 2H), 2.01 (s, 3H), 2.03 (s, 3H), 2.06 (s, 3H), 2.10 (s, 3H), 3.66-3.75 (m, 4H), 3.81 (br dd, J=9.1, 9.1 Hz, 1H, O<u>H</u>), 3.98-4.04 (m, 1H), 4.18 (1H) and 4.24 (1H) (ABq, J$_{AB}$=12.5 Hz; the peaks at both 4.18 and 4.24 are further split into d, J=2.5 Hz and 4.8 Hz, respectively), 4.53 (d, J=8.1 Hz, 1H), 5.00 (dd, J=8.1, 9.9 Hz, 1H), 5.08 (dd, J=9.5, 9.9 Hz, 1H), 5.22 (dd, J=9.5, 9.5 Hz, 1H); $^{13}$C NMR (100.6 MHz, CDCl$_3$) δ 20.8 (q, 2C), 20.9 (q), 21.0 (q), 32.2 (t), 60.2 (t), 62.1 (t), 67.9 (t), 68.6 (d), 71.4 (d), 72.0 (d), 72.9 (d), 101.0 (d), 169.6 (s), 169.7 (s), 170.5 (s), 170.9 (s).

Example 7

11

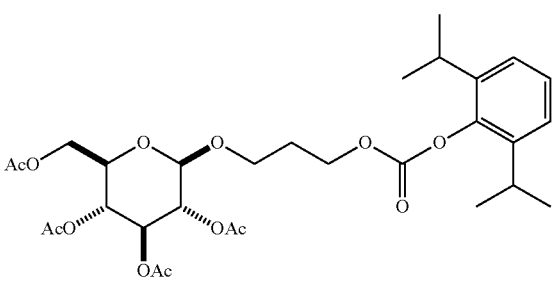

Triphosgene (0.320 g) was dissolved in 10 mL CH$_2$Cl$_2$ and cooled to −78° C. Propofol (0.577 g) was dissolved in 7 mL CH$_2$Cl$_2$ and pyridine (1.022 g) and then added to the triphosgene solution. The reaction was then slowly warmed to room temperature and stirred for 1 hr. The reaction mixture was then cooled back down to −78° C. and 1-(propan-3'-ol)-2,3,4,6-tetra-O-acetyl-β-D-glucopyranoside 10 (1.114 g) dissolved in 10 mL CH$_2$Cl$_2$ added. The reaction mixture was then slowly warmed to room temperature and stirred for another hr. The reaction mixture was then poured into 150 mL CH$_2$Cl$_2$ and was washed once each with water (100 mL), saturated CuSO$_4$ (20 mL), saturated NaHCO$_3$ (50 mL) and brine (50 mL). The organic layer was then dried (Na$_2$SO$_4$), filtered, concentrated and the resultant oil purified by silica gel column chromatography (gradient 10% acetone/hexanes to 30% acetone) to provide 1.204 g (72%) 1-((2',6'-diisopropylphenoxy)carbonyloxy)propyl-2,3,4,6-tetra-O-acetyl-β-D-glucopyranoside 11 as a colorless foam. $[\alpha]^{20}_D$ −11.1° (c 0.81, CH$_2$Cl$_2$); $^1$H NMR (300 MHz, CDCl$_3$) δ 1.22 (d, J=6.9 Hz, 12H), 2.00-2.07 (m, 2H), 2.01 (s, 3H), 2.03 (s, 3H), 2.04 (s, 3H), 2.09 (s, 3H), 3.00 (qq, J=6.9, 6.9 Hz, 2H), 3.60-3.73 (m, 2H), 4.03 (ddd, J=5.5, 5.5, 9.9 Hz, 1H), 4.15 (dd, J=2.2, 12.4 Hz, 1H), 4.25-4.33 (m, 3H), 4.51 (d, J=8.0 Hz, 1H), 5.01 (dd, J=8.0, 9.6 Hz, 1H), 5.09 (dd, J=9.6, 9.6 Hz, 1H), 5.21 (dd, J=9.6, 9.6 Hz, 1H), 7.15 (d, J=8.8 Hz, 1H), 7.16 (d, J=6.6 Hz, 1H), 7.23 (dd, J=6.6, 8.8 Hz, 1H); $^1$H NMR (300 MHz, d$_4$-methanol) δ 1.20 (d, J=6.9 Hz, 12H), 1.96 (s, 3H), 2.00 (s, 6H), 2.04 (s, 3H), 2.99 (qq, J=6.9, 6.9 Hz, 2H), 3.67 (ddd, J=6.3, 6.3, 10.2 Hz, 1H), 3.86 (ddd, J=2.5, 4.7, 9.9 Hz, 1H), 3.96 (ddd, J=5.5, 5.8, 10.0 Hz, 1H), 4.13 (dd, J=2.5, 12.4 Hz, 1H), 4.26-4.34 (m, 3H), 4.66 (d, J=8.0 Hz, 1H), 4.91 (dd, J=8.0, 9.6 Hz, 1H), 5.03 (dd, J=9.6, 9.9 Hz, 1H), 5.26 (dd, J=9.6, 9.6 Hz, 1H), 7.16-7.25 (m, 3H); $^{13}$C NMR (100.6 MHz, CDCl$_3$) δ 20.8 (q, 3C), 20.9 (q), 23.4 (q, 4C), 27.5 (d, 2C), 29.0 (t), 62.0 (t), 65.5 (t), 66.2 (t), 68.5 (d), 71.3 (d), 72.0 (d), 72.9 (d), 101.1 (d), 124.3 (d, 2C), 127.0 (d), 140.6 (s), 145.8 (s, 2C), 154.0 (s), 169.6 (s, 2C), 170.5 (s), 170.9 (s).

Example 8

12

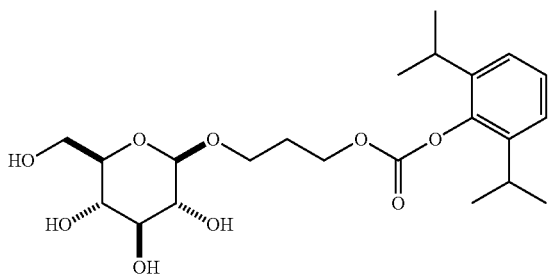

1-((2',6'-Diisopropylphenoxy)carbonyloxy)propyl-2,3,4,6-tetra-O-acetyl-β-D-glucopyranoside 11 (1.200 g) was dissolved in 10 mL methanol and 0.036 g NaHCO$_3$ added. The solution was warmed to 50-60° C. and the progress of the reaction monitored by TLC. After about 2 hrs, the reaction was complete, the reaction cooled to room temperature, and then passed through a short column packed with DOWEX CCR-3 weakly acidic ion exchange resin. The solvent was then removed under reduced pressure and the residue purified by silica gel column chromatography (gradient acetone to 10% methanol in acetone) to provide 0.745 g (86%) 1-((2',6'-diisopropylphenoxy)carbonyloxy)propyl-β-D-glucopyranoside 12 as a colorless foam. $[\alpha]^{21}_D$ −13.3° (c 0.45, acetone); $^1$H NMR (400 MHz, d$_6$-acetone with ca. 4% D$_2$O) δ 1.20 (d, J=7.0 Hz, 12H), 2.06 (dddd, J=6.3, 6.3, 6.3, 6.3 Hz, 2H), 3.03 (qq, J=7.0, 7.0 Hz, 2H), 3.24 (dd, J=7.9, 9.0 Hz, 1H), 3.35-3.40 (m, 2H), 3.44-3.49 (m, 1H), 3.67-3.72 (m, 2H), 4.03 (ddd, J=6.2, 6.2, 10.3 Hz, 1H), 4.36 (d, J=8.1 Hz, 1H), 4.41 (dd, J=6.6, 6.6 Hz, 1H), 7.21-7.29 (m, 3H); $^{13}$C NMR (100.6 MHz, d$_6$-acetone) δ 24.0 (q, 4C), 28.4 (d, 2C), 30.4 (t), 63.4 (t), 66.6 (t), 67.2 (t), 72.1 (d), 75.3 (d), 77.9 (d), 78.4 (d), 104.7 (d), 125.3 (d, 2C), 128.0 (d), 141.8 (s, 2C), 147.1 (s), 155.1 (s); LC-MS (ESI): m/z (%) 460.3 (100, M$^+$+H$_2$O), 442.2 (16, M$^+$), 281.2 (86, iPr$_2$C$_6$H$_3$OCO$_2$CH$_2$CH$_2$CH$_2$OH+1), 263.2 (22), 239.2 (17, C$_6$H$_{11}$O$_5$CH$_2$CH$_2$CH$_2$OH+1), 179.2 (5, propofol+1)

Example 9

14

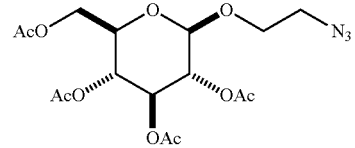

1-(2'-Bromoethyl)-2,3,4,6-β-D-glucose 13 (2.50 g) was dissolved in 10 mL DME and 15 mL water, NaN$_3$ (0.714 g, 2 equiv.) added, the solution warmed to 80° C. and the mixture stirred for 24 hr. The reaction mixture was cooled to room temperature, poured into 100 mL ethyl acetate and washed once each with water (100 mL) and brine (50 mL), dried (Na$_2$SO$_4$), filtered and concentrated under reduced pressure. The resultant crude was purified by silica gel column chromatography (gradient 25% ethyl acetate/hexanes to 50% ethyl acetate/hexanes) provided 2.00 g (87%) 1-(2'-azidoethyl)-2,3,4,6-β-D-glucose 14 as a colorless solid that could be easily recrystallized by dissolving it in 10 mL hot ethyl acetate followed by dilution with 80 mL hot hexanes. $[\alpha]^{20}_D$ −38.3° (c 0.60, CH$_2$Cl$_2$); $^1$H NMR (400 MHz, CDCl$_3$) δ 2.01 (s, 3H), 2.04 (s, 3H), 2.06 (s, 3H), 2.10 (s, 3H), 3.29 (1H) and 3.49 (1H) (ABq, J$_{DB}$=13.5 Hz; the peaks at 3.29 and 3.49 are further split into dd, J=3.3, 4.4 Hz and J=3.3, 8.4 Hz, respectively), 3.70 (ddd, J=3.3, 8.4, 10.6 Hz, 1H), 3.72 (ddd, J=2.2, 4.6, 9.2 Hz, 1H), 4.04 (ddd, J=3.7, 4.8, 10.6 Hz, 1H), 4.17 (1H) and 4.26 (1H) (ABq, J$_{AB}$=12.1 Hz; the peaks at 4.17 and 4.26 are further split into d, J=2.2 and J=4.6 Hz, respectively), 4.60 (d, J=7.7 Hz, 1H), 5.30 (dd, J=7.7, 9.9 Hz, 1H), 5.11 (dd, J=9.5, 9.9 Hz, 1H), 5.22 (dd, J=9.2, 9.5 Hz, 1H); $^{13}$C NMR (100.4 MHz, CDCl$_3$) δ 20.8 (q, 2C), 20.9 (q), 21.0 (q), 50.7 (t), 62.0 (t), 68.5 (d), 68.8 (t), 71.2 (d), 72.1 (d), 73.0 (d), 100.8 (d), 169.6 (s, 2C), 170.5 (s), 170.9 (s)

Example 10

15

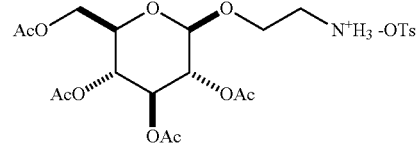

1-(2'-Azidoethyl)-2,3,4,6-β-D-glucose 14 (0.146 g) and dry toluene sulfonic acid (0.069, 1 equiv.) were dissolved in 4 mL ethanol, 5% Pd/C (0.088 g) added, and mixture was stirred for 2 days at room temperature under a blanket of hydrogen. The hydrogen was replaced by nitrogen, the mixture filtered through a pad of celite, and the solvent removed under reduced pressure provided 0.196 g (quantitative) 1-(2'-ammoniummethyl)-2,3,4,6-β-D-glucose toluene sulfonate 15 as a hygroscopic white solid that was used without further purification. $^1$H NMR (300 MHz, CDCl$_3$) δ 1.99 (s, 3H), 2.01 (s, 3H), 2.02 (s, 3H), 2.05 (s, 3H), 2.39 (s, 3H), 3.10-3.33 (m, 2H), 3.67 (br d, J=8.0 Hz, 1H), 3.95-4.02 (m, 3H), 4.39 (br d, J=12.4 Hz, 1H), 4.50 (d, J=8.1 Hz, 1H), 4.91 (dd, J=8.1, 9.4 Hz, 1H), 5.02 (dd, J=9.6, 9.9 Hz, 1H), 5.13 (dd, J=9.4, 9.6 Hz, 1H), 7.22 (d, J=8.1 Hz, 2H), 7.67 (br s, 3H, N$^+$H$_3$), 7.74 (d, J=8.1 Hz, 2H).

Example 11

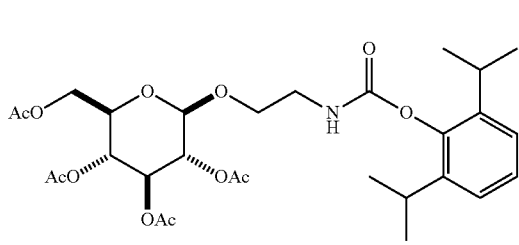

16

Triphosgene (0.047 g) was dissolved in CH$_2$Cl$_2$ (0.5 mL) and cooled to −78° C. Propofol (0.085 g) and pyridine (0.225 g) were dissolved in 1 mL CH$_2$Cl$_2$ and added to the triphosgene mixture. The reaction mixture was warmed to room temperature and stirred for 30 min. The reaction mixture was then cooled back down to −78° C. and 1-(2'-amoniummethyl)-2,3,4,6-β-D-glucose toluene sulfonate 15 (0.179 g) dissolved in 2.5 mL CH$_2$Cl$_2$ added. The reaction mixture was warmed to room temperature and stirred for 1 hr. The reaction mixture was then poured into CH$_2$Cl$_2$ (30 mL) and washed once each with water (30 mL), saturated CuSO$_4$ (30 mL), saturated NaHCO$_3$ (30 mL), and brine (15 mL). The organic layer was then dried (Na$_2$SO$_4$), filtered, and concentrated to provide a crude syrup that was purified by silica gel column chromatography (gradient 25% ethyl acetate/hexanes to 50% ethyl acetate/hexanes) to provide 0.098 g (52%) 1-((2',6'-diisopropylphenoxy)carbonylamino)ethyl-2,3,4,6-tetra-O-acetyl-β-D-glucopyranoside 16 as a colorless foam. $[α]^{20}_D$ −5.0° (c 1.00, CH$_2$Cl$_2$); $^1$H NMR (400 MHz, CDCl$_3$) δ 1.21 (d, J=7.0 Hz, 12H), 2.02 (s, 3H), 2.04 (s, 3H), 2.08 (s, 3H), 2.09 (s, 3H), 3.02 (qq, J=7.0, 7.0 Hz, 2H), 3.46-3.52 (m, 2H), 3.72-3.79 (m, 2H), 3.93 (ddd, J=2.0, 4.9, 9.2 Hz, 1H), 4.18 (1H) and 4.27 (1H) (ABq, J$_{AB}$=12.5 Hz; the peaks at 4.18 and 4.27 are further split into d, J=2.0 and 4.9 Hz, respectively), 4.56 (d, J=8.1 Hz, 1H), 5.04 (dd, J=8.1, 9.7 Hz, 1H), 5.11 (dd, J=9.2, 9.7 Hz, 1H), 5.24 (dd, J=9.2, 9.2 Hz, 1H), 5.53 (br dd, J=6.9, 6.9 Hz, 1H, NH), 7.12-7.22 (m, 3H); $^{13}$C NMR (100.6 MHz, CDCl$_3$) δ 20.6 (q), 20.7 (q), 20.7 (q), 20.8 (q), 20.9 (q), 23.4 (q, 4C), 27.4, (d, 2C), 41.3 (t), 61.9 (t), 68.3 (d), 69.6 (t), 71.4 (d), 72.0 (d), 72.7 (d), 101.2 (d), 123.9 (d, 2C), 126.4 (d), 141.2 (s, 2C), 145.4 (s), 154.9 (s), 169.5 (s), 169.6 (s), 170.3 (s), 170.7 (s).

Example 12

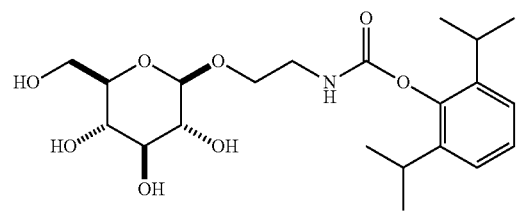

17

1-((2',6'-diisopropylphenoxy)carbonylamino)ethyl-2,3,4,6-tetra-O-acetyl-β-D-glucopyranoside 16 (0.900 g) was dissolved in 20 mL methanol, sodium bicarbonate (0.056 g) added, and the mixture warmed to 50 to 60° C. for 4 hrs. The reaction mixture was then cooled to room temperature and the passed through a short column packed with Dowex CCR-3 weakly acidic ion exchange resin. The solvent was removed under reduced pressure and silica gel column chromatography (gradient 5% methanol in CH$_2$Cl$_2$ to 20% methanol in CH$_2$Cl$_2$) to provide 0.617 g (96%) 1-((2',6'-diisopropylphenoxy)carbonylamino)ethyl-β-D-glucopyranoside 17 as a colorless solid. $[α]^{20}_d$ +14.0° (c 1.00, methanol); $^1$H NMR (400 MHz, d$_6$-acetone with ca. 5% D$_2$O) δ 1.18 (d, J=7.0 Hz, 12H), 3.09 (qq, J=7.0 Hz, 2H), 3.30 (dd, J=8.8, 9.2 Hz, 1H), 3.37-3.45 (m, 3H), 3.47-3.45 (m, 2H), 3.70 (dd, J=5.1, 12.1 Hz, 1H), 3.77 (ddd, J=4.4, 6.6, 10.6 Hz, 1H), 3.89 (d, J=10.6 Hz, 1H), 3.95-4.05 (m, 1H), 4.41 (d, J=7.7 Hz, 1H), 7.15 (d, J=9.2 Hz, 1H), 7.16 (d, J=5.1 Hz, 1H), 7.19 (dd, J=5.1, 9.2 Hz, 1H); $^1$H NMR (400 MHz, d$_4$-methanol) δ 2.00 (d, J=7.0 Hz, 12H), 3.05 (qq, J=Hz, 2H), 3.23 (dd, J=7.7, 9.2 Hz, 1H), 3.28-3.40 (m, 4H), 3.49 (ddd, J=4.4, 5.9, 14.3 Hz, 1H), 3.65-3.74 (m, 2H), 3.88 (d, J=11.7 Hz, 1H), 3.98 (ddd, J=4.4, 5.9, 10.2 Hz, 1H), 4.31 (d, J=7.7 Hz, 1H), 7.13 (d, J=9.5 Hz, 1H), 7.14 (d, J=4.4 Hz, 1H), 7.16 (dd, J=4.4, 9.5 Hz, 1H); $^{13}$C NMR (100.6 MHz, d$_6$-acetone with ca. 5% D$_2$O) δ 23.4 (q, 4C), 27.7 (d, 2C), 41.7 (t), 62.1 (t), 69.5 (t), 70.8 (d), 74.3 (d), 77.1 (d), 77.2 (d), 103.9 (d), 124.2 (d, 2C), 126.7 (d), 141.0 (s, 2C), 146.4 (s), 156.3 (s); $^{13}$C NMR (100.6 MHz, d$_4$-methanol) δ 23.8 (q, 4C), 28.6 (d, 2C), 42.5 (t), 62.9 (t), 70.2 (t), 71.7 (d), 75.3 (d), 78.1 (d), 78.2 (d), 104.9 (d), 124.9 (d, 2C), 127.4 (d), 142.7 (s, 2C), 147.0 (s), 157.7 (s); LC-MS (ESI): m/z (%) 473.3 (55), 428.2 (70, M$^+$+1), 266.2 (100, iPr$_2$C$_6$H$_3$OCONHCH$_2$CH$_2$OH), 224.2 (3, C$_6$H$_{11}$O$_6$CH$_2$CH$_2$NH$_2$+1), 179.2 (5, propofol+1).

Example 13

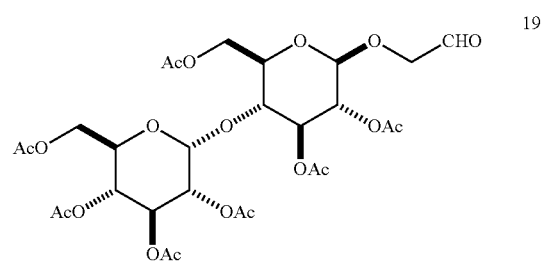

19

1-Allyl hepta-O-acetyl-β-D-maltopyranoside 18 (5.150 g) was dissolved in 50 mL THF and 20 mL water and OsO$_4$ (0.500 g of 4% solution in water, 0.01 equiv.) added. After 40 min., NaIO₄ (3.260 g, 2 equiv.) dissolved in 30 mL water was added over the course of 20 min. The reaction mixture was then stirred for another 1.5 hrs. The mixture was then poured into 200 mL ethyl acetate and 200 mL water. The organic layer was then washed with brine (100 mL), dried (Na₂SO₄), filtered and concentrated to provide a syrup that was purified by silica gel column chromatography (gradient 1:1 ethyl acetate/hexanes to ethyl acetate) to provide 3.402 g (66%) 1-(2'-oxoethyl)hepta-O-acetyl-β-D-maltopyranoside 19 as a colorless solid. $[\alpha]^{21}_D$ +53.0° (c 1.00, $CH_2Cl_2$); $^1H$ NMR (300 MHz, $CDCl_3$) δ 2.01 (s, 3H), 2.02 (s, 3H), 2.03 (s, 3H), 2.05 (s, 3H), 2.06 (s, 3H), 2.11 (s, 3H), 2.14 (s, 3H), 3.71 (ddd, J=2.7, 4.7, 9.4 Hz, 1H), 3.93-4.09 (m, 3H), 4.15-4.30 (m, 4H), 4.48 (dd, J=2.6, 12.3 Hz, 1H), 4.62 (d, J=7.8 Hz, 1H), 4.86 (dd, J=4.1, 10.6 Hz, 1H), 4.93 (dd, J=7.8, 9.4 Hz, 1H), 5.05 (dd, J=9.9, 9.9 Hz, 1H), 5.28 (dd, J=9.1, 9.1 Hz, 1H), 5.36 (dd, J=9.4, 9.6 Hz, 1H), 5.41 (d, J=4.1 Hz, 1H), 9.66 (s, 1H); $^{13}C$ NMR (100.6 MHz, $CDCl_3$) δ 20.7 (q, 2C), 20.7 (q), 20.8 (q), 20.9 (q), 21.0 (q, 2C), 61.6 (t), 62.5 (t), 68.1 (d), 68.7 (d), 69.4 (d), 70.1 (d), 71.8 (d), 72.5 (d), 72.7 (d), 74.3 (t), 75.1 (d), 95.7 (d), 100.6 (d), 169.6 (s), 169.9 (s), 170.1 (s), 170.3 (s), 170.5 (s), 170.7 (s, 2C), 200.0 (d).

Example 14

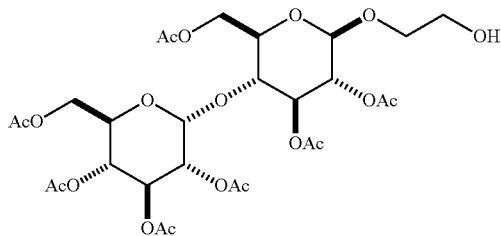

1-(2-Oxyethyl)hepta-O-acetyl-β-D-maltopyranoside 19 (3.400 g) was dissolved in 50 mL methanol and cooled to 0° C. Sodium borohydride (0.225 g, 1.2 equivalents) was then added over the course of 30 min. and the reaction stirred for another hr. Acetic acid (1 mL) was then added and the solvent removed under reduced pressure. The residue was then dissolved in 50 mL $CH_2Cl_2$ and 50 mL brine, the organic layer separated and dried (Na₂SO₄), filtered, and concentrated and residue purified by silica gel column chromatography (gradient $CH_2Cl_2$ to 5% methanol/$CH_2Cl_2$) to provide 3.050 g (89%) 1-(ethan-2-ol) hepta-O-acetyl-β-D-maltopyranoside as a colorless solid. $[\alpha]^{21}_D$ +49.5° (c 0.94, $CH_2Cl_2$); $^1H$ NMR (400 MHz, $CDCl_3$) δ 2.01 (s, 3H), 2.02 (s, 3H), 2.03 (s, 3H), 2.04 (s, 3H), 2.05 (s, 3H), 2.11 (s, 3H), 2.16 (s, 3H), 2.51 (br s, 1H, OH), 3.71-3.78 (m, 2H), 3.82-3.89 (m, 2H), 3.95-4.02 (m, 2H), 4.06 (dd, J=2.2, 12.5 Hz, 1H), 4.18 (1H) and 4.24 (1H) (ABq, $J_{AB}$=12.1 Hz; the peaks at 4.18 and 4.24 are further split into d, J=5.1 Hz and 3.7 Hz, respectively), 4.54 (dd, J=2.6, 12.5 Hz, 1H), 4.58 (d, J=8.0 Hz, 1H), 4.83-4.88 (m, 2H), 5.05 (dd, J=9.9, 9.9 Hz, 1H), 5.27 (dd, J=9.2, 9.2 Hz, 1H), 5.36 (dd, J=9.2, 9.9 Hz, 1H), 5.41 (d, J=3.7 Hz, 1H); $^{13}C$ NMR (100.6 MHz, $CDCl_3$) δ 20.6 (q), 20.6 (q), 20.6 (q), 20.7 (q), 20.7 (q), 20.8 (q), 20.9 (q), 61.5 (t), 61.9 (t), 62.8 (t), 68.0 (d), 68.6 (d), 69.3 (d), 70.0 (d), 72.2 (d), 72.3 (d), 72.7 (d), 73.2 (t), 75.2 (d), 95.6 (d), 100.9 (d), 169.4 (s), 169.8 (s), 170.0 (s), 170.2 (s), 170.5 (s), 170.6 (s, 2C).

Example 15

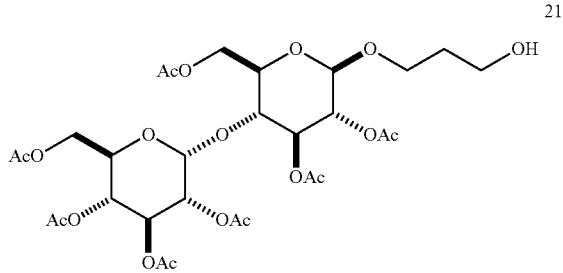

1-Allyl hepta-O-acetyl-β-D-maltopyranoside 18 (5.00 g) was dissolved in 60 mL THF and cooled to 0° C. 9-BBN (22.2 mL 0.5 M solution in THF) was added and the solution stirred for 1 hr, then warmed to room temperature and stirred for an additional hr. The solution was cooled back down to 0° C. and $H_2O_2$ (8 mL 30% solution) was added and stirred overnight at room temperature. The reaction mixture was poured into 250 mL ethyl acetate and washed once each with water (250 mL) and brine (100 mL), dried (Na₂SO₄), filtered and concentrated. The resultant syrup was then purified by silica gel column chromatography (gradient 1:1 ethyl acetate/hexanes to ethyl acetate) to provide 2.60 g (51%) 1-(propan-3-ol) hepta-O-acetyl-β-D-maltopyranoside 21 as a colorless solid. $[\alpha]^{21}_D$ +42.6° (c 0.74, $CH_2Cl_2$); $^1H$ NMR (400 MHz, $CDCl_3$) δ 1.80-1.83 (m, 2H), 1.96 (dd, J=5.5, 5.9 Hz, 1H, OH), 2.01 (s, 6H), 2.03 (s, 3H), 2.03 (s, 3H), 2.05 (s, 3H), 2.11 (s, 3H), 2.16 (s, 3H), 3.67-3.77 (m, 4H), 3.94-4.02 (m, 3H), 4.05 (br d, J=12.4 Hz, 1H), 4.21 (1H) and 4.26 (1H) (ABq, $J_{AB}$=12.5 Hz; the peaks at 4.21 and 4.26 are further split into d, J=4.6 and 3.7 Hz, respectively), 4.35 (dd, J=2.6, 10.3 Hz, 1H), 4.55 (d, J=8.0 Hz, 1H), 4.80-4.88 (m, 2H), 5.06 (dd, J=9.9, 9.9 Hz, 1H), 5.26 (dd, J=8.8, 9.5 Hz, 1H), 5.36 (dd, J=9.5, 10.3 Hz, 1H), 5.42 (d, J=6.0 Hz, 1H); $^{13}C$ NMR (100.6 MHz, $CDCl_3$) δ 20.6 (q), 20.6 (q), 20.7 (q), 20.7 (q), 20.7 (q), 20.9 (q), 21.0 (q), 32.1 (t), 59.9 (t), 61.5 (t), 62.7 (t), 68.0 (t), 68.5 (d), 69.3 (d), 70.0 (d), 72.1 (d), 72.2 (d), 72.7 (d), 75.3 (d), 95.6 (d), 100.3 (d), 169.5 (s), 169.8 (s), 170.0 (s), 170.0 (s), 170.3 (s), 170.6 (s), 170.6 (s).

Example 16

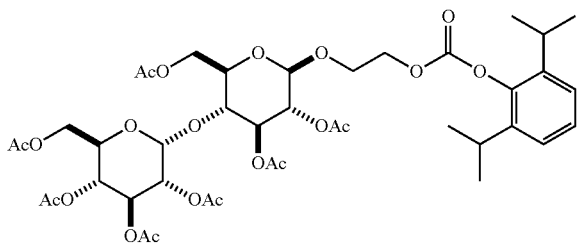

Triphosgene (0.465 g) was dissolved in 2 mL $CH_2Cl_2$ and cooled to −78° C. Propofol (0.838 g) was dissolved in pyridine (2.228 g) and $CH_2Cl_2$ (3 mL) and added to the triphosgene mixture. The reaction mixture was then slowly warmed to room temperature and stirred for 30 min. The reaction mixture was then cooled back down to −78° C. and 1-(ethan-2-ol)hepta-O-acetyl-β-D-maltopyranoside 20 dissolved in 3 mL $CH_2Cl_2$ added. The reaction mixture was again warmed to room temperature and stirred for 2 hr, after which it was poured into 100 mL $CH_2Cl_2$ and was washed once each with water (100 mL), saturated CuSO$_4$ (20 mL), saturated NaHCO$_3$ (50 mL) and brine (50 mL). The organic layer was then dried (Na$_2$SO$_4$), filtered, concentrated and the resultant oil purified by silica gel column chromatography (gradient 50% ethyl acetate/hexanes to 75% ethyl acetate/hexanes) to provide 2.01 g (73%) 1-((2',6'-diisopropylphenoxy)carbonyloxy)ethyl-hepta-O-acetyl-β-D-maltose 22 as a colorless foam. [α]$^{21}_D$ +38.8° (c 1.03, CH$_2$Cl$_2$); $^1$H NMR (400 MHz, CDCl$_3$) δ 1.22 (d, J=7.0 Hz, 12H), 2.01 (s, 3H), 2.03 (s, 3H), 2.04 (s, 3H), 2.05 (s, 3H), 2.06 (s, 3H), 2.11 (s, 3H), 2.15 (s, 3H), 3.01 (qq, J=7.0, 7.0 Hz, 2H), 3.67 (br d, J=9.5 Hz, 1H), 3.83-3.89 (m, 1H), 3.96 (br d, J=9.9 Hz, 1H), 4.00-4.10 (m, 3H), 4.21-4.28 (m, 2H), 4.39 (m, 2H), 4.50 (br d, J=12.1 Hz, 1H), 4.58 (d, J=7.7 Hz, 1H), 4.86 (dd, J=3.3, 10.6 Hz, 1H), 4.87 (d, J=9.9 Hz, 1H), 5.06 (dd, J=9.5, 10.3 Hz, 1H), 5.26 (dd, J=8.8, 9.5 Hz, 1H), 5.37 (dd, J=9.9, 10.3 Hz, 1H), 5.43 (d, J=4.0 Hz, 1H), 7.16 (d, J=8.4 Hz, 1H), 7.17 (d, J=7.0 Hz, 1H), 7.24 (dd, J=7.0, 8.4 Hz, 1H); $^{13}$C NMR (100.6 MHz, CDCl$_3$) δ 20.5 (q), 20.6 (q, 2C), 20.6 (q), 20.7 (q), 20.8 (q), 20.9 (q), 23.3 (q, 4C), 27.3 (d, 2C), 61.5 (t), 62.7 (t), 67.2 (t), 67.4 (t), 68.0 (d), 68.5 (d), 69.3 (d), 70.0 (d), 71.9 (d), 72.2 (d), 72.6 (d), 75.2 (d), 95.5 (d), 100.4 (d), 124.2 (d, 2C), 126.9 (d), 140.4 (s, 2C), 145.6 (s), 153.7 (s), 169.4 (s), 169.7 (s), 169.9 (s), 170.2 (s), 170.4 (s), 170.5 (s), 170.5 (s);

Example 17

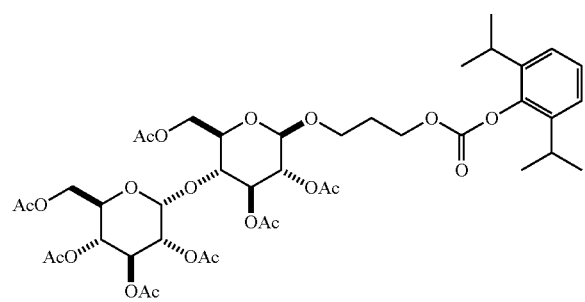

23

Triphosgene (0.205 g) was dissolved in 1 mL CH$_2$Cl$_2$ and cooled to −78° C. Propofol (0.369 g) and pyridine (0.982 g) was dissolved in 1 mL CH$_2$Cl$_2$ and added to the triphosgene solution. The reaction mixture was warmed to room temperature and stirred for 30 min. The reaction mixture was then cooled back down to −78° C. and 1-(propan-3-ol)hepta-O-acetyl-β-D-maltopyranoside 21 (0.960 g) dissolved in 3 mL CH$_2$Cl$_2$ was added. The reaction mixture was then warmed to room temperature and stirred for 2 hr and then poured into 100 mL CH$_2$Cl$_2$ and washed once with 5% HCl (100 mL), saturated CuSO$_4$ (50 mL), water (100 mL), saturated NaHCO$_3$ (100 mL) and brine (50 mL) and then dried (Na$_2$SO$_4$) and concentrated. The resultant syrup was then purified by silica gel column chromatography (gradient 50% ethyl acetate/hexanes to 75% ethyl acetate/hexanes) to provide 1.05 g (85%) 1-((2',6'-diisopropylphenoxy)carbonyloxy)propyl-hepta-O-acetyl-β-D-maltose 23 as a colorless foam. [α]$^{21}_D$ +35.7° (c 1.12, CH$_2$Cl$_2$); $^1$H NMR (400 MHz, CDCl$_3$) δ 1.22 (d, J=6.9 Hz, 12H), 2.00-2.07 (m, 2H), 2.01 (s, 9H), 2.03 (s, 3H), 2.05 (s, 3H), 2.10 (s, 3H), 2.15 (s, 3H), 3.00 (qq, J=6.9, 6.9 Hz, 2H), 3.63-3.70 (m, 2H), 3.96-4.06 (m, 4H), 4.22-4.32 (m, 4H), 4.49 (br d, J=10.6 Hz, 1H), 4.54 (d, J=7.7 Hz, 1H), 4.82-4.88 (m, 2H), 5.06 (dd, J=9.9, 9.9 Hz, 1H), 5.26 (dd, J=8.8, 9.2 Hz, 1H), 5.37 (dd, J=9.9, 9.9 Hz, 1H), 5.43 (d, J=4.0 Hz, 1H), 7.16 (d, J=8.8 Hz, 1H), 7.17 (d, J=6.6 Hz, 1H), 7.22 (dd, J=6.6, 8.4 Hz, 1H); $^{13}$C NMR (100.6 MHz, CDCl$_3$) δ 20.5 (q), 20.6 (q, 2C), 20.6 (q), 20.7 (q), 20.8 (q), 20.9 (q), 23.2 (q, 4C), 27.3 (d, 2C), 28.8 (t), 61.4 (t), 62.7 (t), 65.3 (t), 66.0 (t), 68.0 (d), 68.5 (d), 69.3 (d), 69.9 (d), 72.0 (d), 72.1 (d), 72.6 (d), 75.3 (d), 95.5 (d), 100.4 (d), 124.1 (d, 2C), 126.8 (d), 140.4 (s, 2C), 145.6 (s), 153.7 (s), 169.4 (s), 169.7 (s), 169.9 (s), 170.2 (s), 170.4 (s), 170.5 (s), 170.5 (s).

Example 18

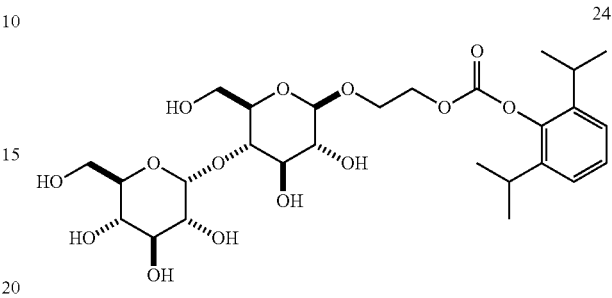

24

1-((2',6'-Diisopropylphenoxy)carbonyloxy)ethyl-hepta-O-acetyl-β-D-maltose 22 (1.400 g) was dissolved in 25 mL methanol and 0.059 g NaHCO$_3$ added. The reaction mixture was warmed to 50-60° C. and monitored by TLC. After 4 hr the reaction was complete and passed through a short column packed with DOWEX CCR-3 weakly acidic ion exchange resin. The solvent was removed under reduced pressure and purified by silica gel column chromatography (gradient 20:1 to 5:1 CH$_2$Cl$_2$/methanol) to provide 0.730 g (78%) 1-((2',6'-diisopropylphenoxy)carbonyloxy)ethyl-β-D-maltose 24 as a colorless foam. [α]$^{21}_D$+50.5° (c 1.00, methanol); $^1$H NMR (400 MHz, d$_4$-methanol) δ 1.20 (d, J=7.0 Hz, 12H), 3.00 (qq, J=7.0, 7.0 Hz, 2H), 3.24-3.35 (m, 2H), 3.39 (ddd, J=1.5, 4.2, 9.5 Hz, 1H), 3.45 (dd, J=3.7, 9.9 Hz, 1H), 3.55 (dd, J=9.2, 9.5 Hz, 1H), 3.59-3.72 (m, 4H), 3.78-3.86 (m, 2H), 3.83-3.92 (m, 2H), 4.15 (ddd, J=3.0, 6.2, 11.7 Hz, 1H), 4.36 (d, J=7.7 Hz, 1H), 4.39-4.52 (m, 2H), 5.17 (d, J=3.7 Hz, 1H), 7.16-7.25 (m, 3H); $^{13}$C NMR (100.6 MHz, D$_2$O) δ 23.5 (q, 4C), 27.7 (d, 2C), 61.1 (t), 61.4 (t), 67.9 (t), 68.7 (t), 69.8 (d), 72.4 (d), 73.4 (d), 73.6 (2C), 75.2 (d), 76.7 (d), 78.1 (d), 100.8 (d), 103.1 (d), 124.8 (d, 2C), 127.7 (d), 141.1 (s, 2C), 146.0 (s), 154.9 (s); $^{13}$C NMR (75.4 MHz, DMSO) δ 23.2 (q, 4C), 26.8 (d, 2C), 60.7 (t), 60.8 (t), 66.4 (t), 68.2 (t), 69.9 (d), 72.5 (d), 72.9 (d), 73.3 (d), 73.6 (d), 75.3 (d), 76.5 (d), 79.7 (d), 100.9 (d), 102.9 (d), 124.2 (d, 2C), 126.9 (d), 140.1 (s, 2C), 145.2 (s), 153.4 (s); LC-MS (ESI): m/z (%) 608.3 (43, M$^+$+H$_2$O), 267.2 (94, iPr$_2$C$_6$H$_3$OCO$_2$CH$_2$CH$_2$OH+1), 225.1 (100, C$_6$H$_{11}$O$_6$CH$_2$CH$_2$OH+1).

Example 19

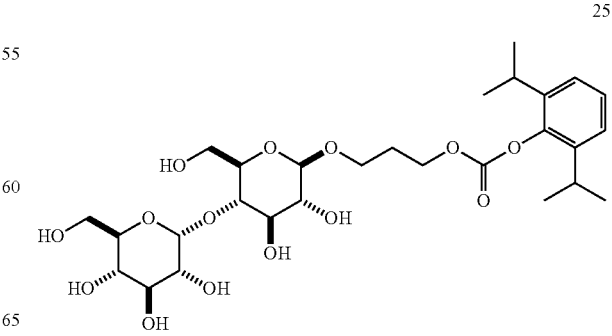

25

1-((2',6'-Diisopropylphenoxy)carbonyloxy)propyl-hepta-O-acetyl-β-D-maltose 23 (1.14 g) was dissolved in 25 mL methanol, NaHCO$_3$ (0.047 g) added, and the reaction mixture warmed to 50-60° C. and stirred for 2.5 hrs. The reaction mixture was then cooled to room temperature and passed through a short column containing DOWEX CCR-3 weakly acidic ion exchange resin, the solvent removed under reduced pressure, and the resultant syrup purified by silica gel column chromatography to provide 0.678 g (88%) 1-((2',6'-diisopropylphenoxy)carbonyloxy)propyl-β-D-maltose 25 as a colorless foam. $[α]^{20}_D$+43.5° (c 1.00, methanol); $^1$H NMR (400 MHz, d$_4$-methanol) δ 1.20 (d, J=7.0 Hz, 12H), 2.05 (dddd, J=6.3, 6.3, 6.3, 6.3 Hz, 2H), 2.99 (qq, J=7.0, 7.0 Hz, 2H), 3.22-3.34 (m, 2H), 3.37 (ddd, J=1.8, 4.4, 9.5 Hz, 1H), 3.44 (dd, J=3.7, 10.9 Hz, 1H), 3.55 (dd, J=9.5, 9.8 Hz, 1H), 3.58-3.74 (m, 5H), 3.79-3.92 (m, 3H) 4.02 (ddd, J=5.9, 6.2, 10.3, 1H), 4.30 (d, J=8.1 Hz, 1H), 4.35-4.43 (m, 2H), 5.16 (d, J=3.7 Hz, 1H), 7.16-7.24 (m, 3H); $^{13}$C NMR (75.4 MHz, DMSO) δ 23.1 (q, 4C), 26.9 (d, 2C), 28.7 (t), 60.6 (t), 60.8 (t), 65.0 (t), 66.1 (t), 69.9 (d), 72.5 (d), 73.0 (d), 73.3 (d), 73.5 (d), 75.2 (d), 76.4 (d), 79.7 (d), 100.9 (d), 102.9 (d), 124.2 (d, 2C), 126.9 (d), 140.0 (s, 2C), 145.2 (s), 153.3 (s); LC-MS (ESI): m/z (%) 622.3 (25, M+H$_2$O), 281.2 (100, iPr$_2$C$_6$H$_3$OCO$_2$CH$_2$CH$_2$CH$_2$OH+1), 263.2 (32), 239.2 (27, C$_6$H$_{11}$O$_6$CH$_2$CH$_2$CH$_2$OH+1), 221.2 (7), 179.2 (7, propofol+1).

Example 20

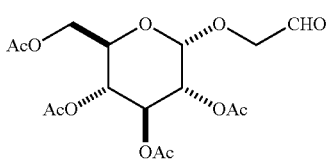

27

1-Allyl 2,3,4,6-tetra-O-acetyl-α-D-glucopyranoside 26 (2.50 g) was dissolved in THF (30 mL) and water (10 mL) and OsO$_4$ (0.064 g 4% solution in water, 0.01 equiv.) added. After the reaction stirred for 40 min, NaIO$_4$ (2.75 g, 2 equiv.) dissolved in 20 mL water was added over the course of 20 min. and the reaction mixture stirred for an additional 1.5 hr. The reaction mixture was then poured into 30 mL ethyl acetate and washed once with brine (30 mL), dried (Na$_2$SO$_4$), filtered and concentrated under reduced pressure. The resultant syrup was then purified by silica gel column chromatography (gradient 50% ethyl acetate/hexanes to ethyl acetate) to provide 2.00 g (80%) 1-(2'-oxyethyl) 2,3,4,6-tetra-O-acetyl-α-D-glucopyranoside 27 as a colorless oil. $[α]^{19}_D$ +135.5° (c 1.00, CH$_2$Cl$_2$); $^1$H NMR (400 MHz, CDCl$_3$) δ 2.04 (s, 3H), 2.05 (s, 3H), 2.10 (s, 3H), 2.13 (s, 3H), 4.08-4.16 (m, 2H), 4.22-4.28 (m, 3H), 4.92 (dd, J=3.7, 10.3 Hz, 1H), 5.09 (dd, J=9.5, 10.3 Hz, 1H), 5.13 (d, J=3.7 Hz, 1H), 5.55 (dd, J=9.5, 10.3 Hz, 1H), 9.71 (s, 1H); $^{13}$C NMR (100.6 MHz, CDCl$_3$) δ 20.8 (q), 20.9 (q, 3C), 61.9 (t), 68.1 (d), 68.4 (d), 69.8 (d), 70.6 (d), 73.3 (t), 96.6 (d), 169.8 (s), 170.2 (s), 170.5 (s), 170.8 (s), 198.1 (d).

Example 21

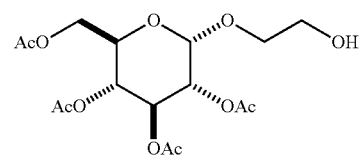

28

1-(2'-Oxyethyl) 2,3,4,6-tetra-O-acetyl-α-D-glucopyranoside 27 was dissolved in methanol (25 mL), cooled to 0° C. and NaBH$_4$ (0.277 g, 1.5 equiv.) dissolved in methanol (25 mL) added over the course of 30 min. After stirring an additional 30 min, acetic acid (1 mL) was added and the solvent removed under reduced pressure. The residue was dissolved in CH$_2$Cl$_2$ (50 mL) and brine (25 mL), the organic layer separated, dried and concentrated under reduced pressure. The resultant syrup was then purified by silica gel column chromatography (gradient 50% ethyl acetate/hexanes to ethyl acetate) to provide 1.65 g (86%) 1-(ethan-2'-ol)-2,3,4,6-tetra-O-acetyl-α-D-glucopyranoside 28 as a colorless foam. Conversely, 1-allyl 2,3,4,6-tetra-O-acetyl-α-D-glucopyranoside 26 (1.30 g) was dissolved in THF (30 mL) and water (10 mL) and OsO$_4$ (0.213 g 4% solution in water, 0.01 equiv.) added. After the reaction stirred for 40 min, NaIO$_4$ (1.432 g, 2 equiv) dissolved in 20 mL water was added over the course of 20 min, and the reaction mixture stirred for an additional 1.5 hr. The reaction mixture was poured into 100 mL CH$_2$Cl$_2$ and washed once with brine (30 mL). The organic layer was dried (Na$_2$SO$_4$), filtered through a plug of silica gel and the solvent removed under reduced pressure. The crude aldehyde was then dissolved in methanol (20 mL), cooled to 0° C., and NaBH$_4$ (0.080 g) added in portions over the course of 15 min. TLC indicated that the reduction was complete after 20 min, acetic acid (0.2 mL) added, and the solvent removed under reduced pressure. The resultant residue was then dissolved in CH$_2$Cl$_2$ (100 mL) and water (50 mL), and the organic layer was washed with brine (50 mL), dried (Na$_2$SO$_4$) filtered and concentrated. The crude was purified by silica gel column chromatography (3:1 ethyl acetate/hexanes) provided 0.781 g (60%) 1-(ethan-2'-ol)-2,3,4,6-tetra-O-acetyl-α-D-glucopyranoside 28 as a colorless oil that solidified overnight. $[α]^{19}_D$ +122.5° (c 1.11, CH$_2$Cl$_2$); $^1$H NMR (400 MHz, CDCl$_3$) δ 2.03 (s, 3H), 2.04 (s, 3H), 2.08 (s, 3H), 2.11 (s, 3H), 3.61-3.67 (m, 1H), 3.77-3.85 (m, 2H), 4.12 (1H) and 4.25 (1H) (ABq, J$_{AB}$=12.8 Hz; the peaks at 4.25 are further split into, J=5.2 Hz), 4.92 (dd, J=3.7, 10.2 Hz, 1H), 5.07 (dd, J=9.5, 9.9 Hz, 1H), 5.12 (d, J=3.7 Hz, 1H), 5.50 (dd, J=9.5, 10.2 Hz, 1H); $^{13}$C NMR (100.6 MHz, CDCl$_3$) δ 20.8 (q), 20.8 (q), 20.9 (q), 20.9 (q), 61.7 (t), 62.1 (t), 67.6 (d), 68.6 (d), 70.2 (d), 70.8 (t), 70.9 (d), 96.4 (d), 169.8 (s), 170.3 (s), 170.4 (s), 170.8 (s).

Example 22

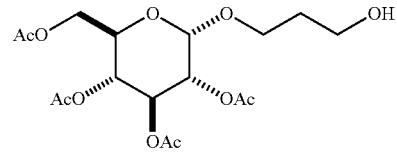

29

1-Allyl 2,3,4,6-tetra-O-acetyl-α-D-glucopyranoside 26 (2.20 g) was dissolved in THF (5 mL) and cooled to 0° C. 9-BBN (22.7 mL 0.5 M solution in THF) was added and the solution was stirred for 1 hr, warmed to room temperature and stirred for an additional 1 hr. The solution was cooled back down to 0° C. and $H_2O_2$ (11.5 mL 30% solution) was added and the solution stirred for another 1 hr. The solution was then poured into $CH_2Cl_2$ (25 mL) and washed once each with water (10 mL) and brine (10 mL), the organic layer dried ($Na_2SO_4$), filtered and concentrated. The resultant crude was purified by silica gel column chromatography (gradient 50% ethyl acetate/hexanes to ethyl acetate) to provide 1.515 g (66%) 1-(propan-3'-ol)-2,3,4,6-tetra-O-acetyl-α-D-glucopyranoside 29 as a colorless foam. $[\alpha]^{19}_D$+118.5° (c 1.00, $CH_2Cl_2$); $^1$H NMR (400 MHz, $CDCl_3$) δ 1.84-1.91 (m, 2H), 2.02 (s, 3H), 2.04 (s, 3H), 2.08 (s, 3H), 2.10 (s, 3H), 3.58 (ddd, J=5.2, 6.7, 10.1 Hz, 1H), 3.76-3.81 (m, 2H), 3.91 (ddd, J=5.3, 6.2, 10.1 Hz, 1H), 4.03 (ddd, J=2.6, 4.4, 10.3 Hz, 1H), 4.12 (1H) and 4.26 (1H) (ABq, $J_{AB}$=12.1 Hz; the peaks at 4.12 are further split into d, J=4.4 Hz, and the peaks at 4.26 further split into dd, J=1.8, 2.6 Hz), 4.90 (dd, J=3.7, 10.3 Hz, 1H), 5.06 (dd, J=9.5, 10.3 Hz, 1H), 5.09 (d, J=3.7 Hz, 1H), 5.46 (dd, J=9.5, 10.3 Hz, 1H); $^{13}$C NMR (100.6 MHz, $CDCl_3$) δ 20.8 (q), 20.8 (q), 20.9 (q), 20.9 (q), 31.8 (t), 60.9 (t), 62.1 (t), 66.9 (t), 67.4 (d), 68.7 (d), 70.4 (d), 70.8 (d), 95.9 (d), 169.8 (s), 170.3 (s, 2C), 170.9 (s).

Example 23

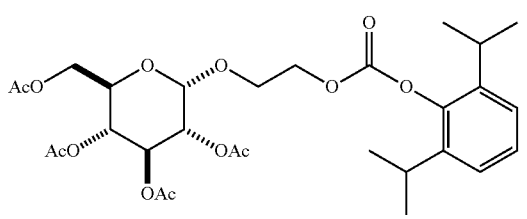

Triphosgene (0.189 g) was dissolved in $CH_2Cl_2$ (0.5 mL) and cooled to −78° C. Propofol (0.341 g) and pyridine (0.503 g) were dissolved in $CH_2Cl_2$ (2 mL) and added to the triphosgene solution. The reaction mixture was warmed to room temperature and stirred for 15 min, then cooled back down to −78° C. 1-(Ethan-2'-ol)-2,3,4,6-tetra-O-acetyl-α-D-glucopyranoside 28 (0.500 g) was dissolved in $CH_2Cl_2$ (2 mL) and added to the mixture. The reaction was then warmed to room temperature and stirred for 2 hrs, after which it was poured into 50 mL $CH_2Cl_2$ and washed once each with 5% HCl (50 mL), saturated $CuSO_4$ (50 mL), water (50 mL), saturated $NaHCO_3$ (50 mL) and brine (25 mL). The organic layer was then dried ($Na_2SO_4$), filtered, and concentrated under reduced pressure and the resultant crude product was purified by silica gel column chromatography (gradient 25% ethyl acetate/hexanes to 50% ethyl acetate) to provide 0.650 g (86%) 1-((2',6'-diisopropylphenoxy)carbonyloxy)ethyl-2,3,4,6-tetra-O-acetyl-α-D-glucopyranoside 30 as a colorless foam. $[\alpha]^{22}_D$+80.9° (c 1.02, $CH_2Cl_2$); $^1$H NMR (400 MHz, $CDCl_3$) δ 1.22 (d, J=7.0 Hz, 12H), 2.03 (s, 3H), 2.04 (s, 3H), 2.07 (s, 3H), 2.10 (s, 3H), 3.02 (qq, J=7.0 Hz, 2H), 3.84 and 3.96 (1H) (ABq, $J_{AB}$=11.7 Hz; the peaks at 3.84 and 3.96 are further split into dd, J=3.3, 5.9 Hz and J=3.3, 6.2 Hz, respectively), 4.06-4.15 (m, 2H), 4.29 (dd, J=4.8, 13.2 Hz, 1H), 4.40 (1H) and 4.46 (1H) (ABq, $J_{AB}$=12.1 Hz; the peaks at 4.40 and 4.46 are further split into dd, J=3.3, 5.9 Hz and J=3.3, 6.2 Hz, respectively), 4.90 (dd, J=3.7, 9.9 Hz, 1H), 5.10 (dd, J=9.5, 9.9 Hz, 1H), 5.17 (d, J=3.7 Hz, 1H), 5.51 (dd, J=9.5, 9.9 Hz, 1H) 7.16 (d, J=8.4 Hz, 1H), 7.17 (d, J=6.6 Hz, 1H), 7.23 (dd, J=6.6, 8.4 Hz, 1H); $^{13}$C NMR (100.6, $CDCl_3$) δ 20.8 (q, 2C), 20.9 (q, 2C), 23.5 (q, 4C), 27.6 (d, 2C), 61.9 (t), 66.6 (t), 67.2 (t), 67.7 (d), 68.5 (d), 70.2 (d), 70.9 (d), 96.3 (d), 124.4 (d, 2C), 127.1 (d), 140.6 (s, 2C), 144.4 (s), 153.9 (s), 169.8 (s), 170.3 (s), 170.5 (s), 170.9 (s).

Example 24

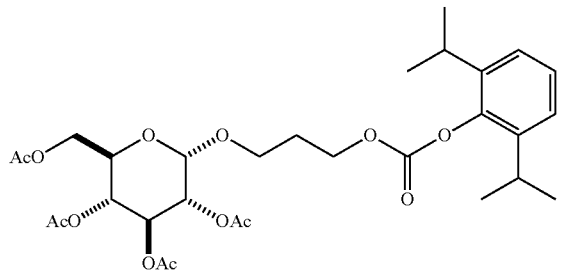

Triphosgene (0.237 g) was dissolved in $CH_2Cl_2$ (0.5 mL) and cooled to −78° C. Propofol (0.428 g) and pyridine (0.632) were dissolved in $CH_2Cl_2$ (2 mL) and added to the triphosgen solution. The reaction mixture was then warmed to room temperature and stirred for 30 min before cooling it back down to −78° C. 1-(Propan-3'-ol)-2,3,4,6-tetra-O-acetyl-α-D-glucopyranoside 29 (0.650 g) was dissolved in $CH_2Cl_2$ (2 mL) and added to the reaction mixture. The mixture was warmed to room temperature and stirred for 2 hr. The reaction mixture was then poured into $CH_2Cl_2$ (50 mL), and washed once each with 5% HCl (50 mL), saturated $CuSO_4$ (50 mL), water (50 mL), saturated $NaHCO_3$ (50 mL) and brine (25 mL). The organic layer was dried ($Na_2SO_4$), filtered and concentrated under reduced pressure to provide the crude product that was purified by silica gel column chromatography (gradient 25% ethyl acetate/hexanes to 50% ethyl acetate) to provide 0.745 g (76%) 1-((2',6'-diisopropylphenoxy)carbonyloxy)propyl-2,3,4,6-tetra-O-acetyl-α-D-glucopyranoside 31 as a colorless foam. $[\alpha]^{22}_D$+82.5° (c 1.00, $CH_2Cl_2$); $^1$H NMR (400 MHz, $CDCl_3$) δ 1.21 (d, J=7.0 Hz, 12H), 2.02 (s, 3H), 2.04 (s, 3H), 2.04-2.10 (m, 2H), 2.09 (s, 3H), 2.10 (s, 3H), 3.00 (qq, J=7.0 Hz, 2H), 3.56 (ddd, J=6.2, 6.6, 10.2 Hz, 1H), 3.87 (ddd, J=5.5, 5.9, 10.2 Hz, 1H), 4.03 (ddd, J=2.2, 4.4, 9.9 Hz, 1H), 4.10 (1H) and 4.28 (1H) (ABq, $J_{AB}$=12.1 Hz; the peaks at 4.10 and 4.28 are further split into d, J=2.2 and 4.4 Hz, respectively), 4.34 (dd, J=3.7, 9.5 Hz, 1H), 4.36 (1H) and 4.39 (1H) (ABq, $J_{AB}$=11.0 Hz; the peaks at 4.36 and 4.39 are both each further split into dd, J=6.2, 6.2), 5.07 (dd, J=9.5, 9.9 Hz, 1H), 5.09 (d, J=3.7 Hz, 1H), 5.48 (dd, J=9.5, 9.9 Hz, 1H), 7.15 (d, J=8.4 Hz, 1H), 7.16 (d, J=6.6 Hz, 1H), 7.23 (dd, J=6.6, 8.4 Hz, 1H); $^{13}$C NMR (100.6 MHz, $CDCl_3$) δ 20.8 (q), 20.8 (q), 20.9 (q, 2C), 23.5 (q, 4C), 27.6 (d, 2C), 28.9 (t), 62.0 (t), 64.9 (t), 65.5 (t), 67.6 (d), 68.7 (d), 70.3 (d), 70.9 (d), 96.2 (d), 124.3 (d, 2C), 127.0 (d), 140.6 (s, 2C), 145.8 (s), 154.0 (s), 169.8 (s), 170.4 (s, 2C), 170.9 (s).

Example 25

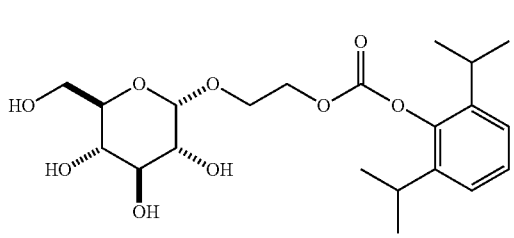 [SMILES: CC(C)c1cccc(C(C)C)c1OC(=O)OCCO[C@H]1O[C@H](CO)[C@@H](O)[C@H](O)[C@H]1O]

1-((2',6'-Diisopropylphenoxy)carbonyloxy)ethyl-2,3,4,6-tetra-O-acetyl-α-D-glucopyranoside 30 (0.700 g) was dissolved in methanol (20 mL), NaHCO$_3$ added, the mixture warmed to 50-60° C. and stirred for 2 hrs. The reaction mixture was then cooled to room temperature and then passed through a short column containing DOWEX CCR-3 weakly acidic ion exchange resin. The solvent was removed under reduced pressure and the crude product purified by silica gel column chromatography (gradient 2% methanol/CH$_2$Cl$_2$ to 10% methanol/CH$_2$Cl$_2$) to provide 0.413 g (82%) 1-((2',6'-diisopropylphenoxy)carbonyloxy)ethyl-α-D-glucopyranoside 32 as a colorless foam. [α]$_D^{22}$ +59.0° (c 1.00, CH$_2$Cl$_2$) $^1$H NMR (400 MHz, d$_6$-acetone with 1 drop D$_2$O) δ 1.20 (d, J=6.6 Hz, 12H), 3.05 (qq, J=6.6, 6.6 Hz, 2H), 3.60-3.85 (m, 5H), 3.40-3.48 (m, 2H), 4.00-4.04 (m, 1H), 4.50 (br s, 2H), 4.90 (d, J=3.3 Hz, 1H), 7.21-7.29 (m, 3H); $^1$H NMR (400 MHz, d$_4$-methanol) δ 1.20 (d, J=7.0 Hz, 12H), 3.00 (qq, J=7.0, 7.0 Hz, 2H), 3.34 (dd, J=9.2, 9.9 Hz, 1H), 3.43 (dd, J=3.7, 9.9 Hz, 1H), 3.62-3.74 (m, 3H), 3.79-3.85 (m, 2H), 4.00 (ddd, J=4.0, 5.5, 12.1 Hz, 1H), 4.44-4.48 (m, 2H), 4.88 (d, J=3.7, 1H), 7.17 (d, J=9.2 Hz, 1H), 7.18 (d, J=5.5 Hz, 1H), 7.22 (dd, J=5.5, 9.2 Hz, 1H); $^{13}$C NMR (100.6 MHz, d$_6$-acetone) δ 23.6 (q, 4C), 28.0 (d, 2C), 62.8 (t), 66.7 (t), 68.7 (d), 71.7 (d), 73.5 (d), 73.6 (d), 75.2 (d), 100.4 (d), 124.9 (d, 2C), 127.7 (d), 141.5 (s, 2C), 146.7 (s), 154.7 (s); $^{13}$C NMR (100.6 MHz, d$_4$-methanol) δ 23.8 (q, 4C), 28.7 (d, 2C), 62.7 (t), 67.2 (t), 69.3 (t), 71.7 (d), 73.7 (d), 74.0 (d), 75.2 (d), 100.9 (d), 125.3 (d, 2C), 128.1 (d), 141.9 (s, 2C), 147.1 (s), 155.7 (s); LC-MS (ESI): m/z 474.3 (100), 446.3 (27, M$^+$+H$_2$O), 428.2 (6, M$^+$), 267.2 (33, iPr$_2$C$_6$H$_3$OCO$_2$CH$_2$CH$_2$OH+1), 225.2 (31, C$_6$H$_{11}$O$_6$CH$_2$CH$_2$OH+1).

Example 26

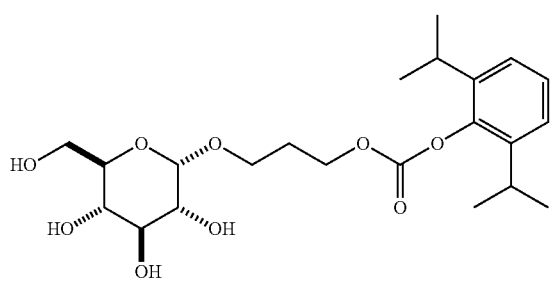 [SMILES: CC(C)c1cccc(C(C)C)c1OC(=O)OCCCO[C@H]1O[C@H](CO)[C@@H](O)[C@H](O)[C@H]1O]

1-((2',6'-Diisopropylphenoxy)carbonyloxy)propyl-2,3,4,6-tetra-O-acetyl-α-D-glucopyranoside 31 (0.600 g) was dissolved in 10 mL methanol, NaHCO$_3$ added, the reaction mixture warmed to 50-60° C. and stirred for 2 hr. The reaction was then cooled to room temperature and passed through a short column containing DOWEX CCR-3 weakly acidic ion exchange resin. The solvent was removed under reduced pressure and the resultant crude product was purified by silica gel column chromatography (gradient 2% methanol/CH$_2$Cl$_2$ to 10% methanol/CH$_2$Cl$_2$) to provide 0.394 g (91%) 1-((2',6'-diisopropylphenoxy)carbonyloxy)propyl-α-D-glucopyranoside 33 as a colorless foam. [α]$_D^{19}$ +72.8° (c 1.03, methanol); $^1$H NMR (400 MHz, d$_4$-methanol) δ 1.20 (d, J=7.0, 12H), 2.07 (m, 2H), 2.99 (qq, J=7.0, 7.0 Hz, 2H), 3.32 (dd, J=7.0, 9.5 Hz, 1H), 3.41 (dd, J=3.7, 9.9 Hz, 1H), 3.65 (dd, J=9.2, 9.5 Hz, 1H), 3.54-3.60 (m, 2H), 3.70 (dd, J=5.5, 11.7 Hz, 1H), 3.81 (dd, J=2.2, 11.7 Hz, 1H), 3.89 (ddd, J=5.9, 6.6, 9.9 Hz, 1H), 4.38 (1H) and 4.42 (1H) (ABq, J$_{AB}$=10.6 Hz; the peaks at 4.38 and 4.42 are both each further split into dd, J=6.6, 6.6 Hz), 4.81 (d, J=3.7 Hz, 1H), 7.17 (d, J=8.8 Hz, 1H), 7.18 (d, J=5.5 Hz, 1H), 7.22 (dd, J=5.5, 8.8 Hz, 1H); $^{13}$C NMR (100.6, d$_6$-acetone) δ 23.8 (q, 4C), 28.2 (d, 2C), 29.9 (t), 62.9 (t), 64.8 (t), 67.0 (t), 71.9 (d), 73.6 (d, 2C), 75.5 (d), 100.2 (d), 125.1 (d, 2C), 127.8 (d), 141.6 (s, 2C), 146.9 (s), 154.9 (s); $^{13}$C NMR (100.6 MHz, d$_4$-methanol) δ 23.8 (q, 4C), 28.7 (d, 2C), 30.1 (t), 62.7 (t), 65.2 (t), 67.4 (t), 71.8 (d), 73.7 (d), 73.9 (d), 75.2 (d), 100.5 (d), 125.3 (d, 2C), 128.1 (d), 141.8 (s, 2C), 147.2 (s), 155.6 (s); LC-MS (ESI): m/z 488.4 (100), 460.3 (48, M$^+$+H$_2$O), 442.3 (M$^+$), 281.2 (86, iPr$_2$C$_6$H$_3$OCO$_2$CH$_2$CH$_2$CH$_2$OH+1), 263.2 (22), 239.2 (14, C$_6$H$_{11}$O$_6$CH$_2$CH$_2$CH$_2$OH+1), 179.2 (5, propofol+1).

Example 27

Pharmacokinetics

General Study Design.

Each of the analogs and 9, 12, 17, 24, 25, 32, and 33 and propofol were to be tested on three male Sprague Dawley rats each at identical doses per weight. If possible, each analog and propofol was to be formulated in water only. Each analog and propofol were to be formulated at identical molar concentrations based on a dose of 30 mg/Kg propofol and administered to the rats i.v. at identical rates of 1 mL/Kg/min for a period of 10 minutes. Blood samples were to be taken pre-dose, during dose and post dose at designated intervals, with the blood quickly processed and stored at −70° C. until analysis.

Animal Specifications.

The male Sprague Dawley rats were obtained from SLAC Laboratory Animal Co. Ltd., Shanghai, China. Following arrival at the testing facility (WuXi AppTec in Shanghai, China), the, rats were assessed as to their general health by a member of the veterinary staff. The rats were acclimated for at least 3 days upon arrival at WuXi AppTec before being placed on study.

Animal Husbandry.

The rats were group-housed during acclimation and individually housed during the study. The animal room environment was controlled (temperature 18 to 26° C., relative humidity 30 to 70%, 12 hours artificial light and 12 hours dark, monitored daily). All animals had access to Certified Rodent Diet (Catalog #M-01F, SLAC Laboratory Animal Co. Ltd., Shanghai, China) ad libitum with each lot number and specifications of each lot used archived. Water was autoclaved before provided to the animals ad libitum; periodic analysis of the water was performed and the results archived.

Dose Formulation.

Formulations were prepared on the morning of the dosing day and each was passed through a 0.22 μm filter prior to being administered to animals. A standard dose of 0.168 mmol/Kg per analog was administered to each of the rats. The formulation for analogs 9, 12, 24, 25, 32, and 33 and propofol was water; due to its poor solubility, the formulation for 17 was 10% tween20 in water. Analog stability in the formulations was verified by preparing each formulation and harvesting 200 μL aliquots at 0, 1, 2 and 8 hr while standing at room temperature. After harvesting, each sample was immediately frozen in dry ice until analysis; concentrations of test compounds in the samples were examined by HPLC-UV. Dose formulations were assayed in duplicates for each dose with a calibration curve at least 5 points; it was verified that each analog was stable in its formulation.

Dose Administration.

The animals were surgically prepared with indwelling cannula, double cannulation in carotid artery and jugular vein for i.v. infusion. The anesthetic pentobarbital was used during the surgery, and the animals were allowed to recover 3-5 days after surgery before the formulation was dosed. The dose formulation was administered intravenously via the jugular vein cannula. The 16.8 μmol/mL formulation was administered i.v. at a rate of 1 mL/Kg/min for 10 min.

Blood collection.

Approximately 0.20 mL blood was collected at each designated time point from carotid artery via a catheter. A total of 12 plasma samples were taken from each animal: 1 pre-dose; 2 during the dose (5 into the 10 min infusion and one just prior termination of the 10 min infusion) and 9 post-infusion at 2, 5, 15, 30 min and 1, 2, 3, 4, and 6 hr post-dose. All blood samples were transferred into plastic microcentrifuge tubes containing 5 μL of $K_2$-EDTA (0.5M) as anti-coagulant and placed on ice until processed for plasma. Blood samples were processed for plasma by centrifugation at approximately 5° C. Plasma samples were then stored in 1.5 mL tubes, quick frozen over dry ice and kept at −70±10° C. until LC/MSMS analysis.

Analog and Propofol Concentration in Blood Evaluation:

The plasma concentrations of each of the analogs and propofol were quantified by LC/MS/MS with an internal standard. For each, a minimum of 6 standard point curve runs in duplicates, and minimum of 5 standards were back calculated to within ±20% of their nominal concentrations. The LLOQ of each test article in plasma was established and 6 QC samples were included in assay runs of samples to ensure assay performance. It was confirmed that the measured concentration of each QC sample was within ±20% of their nominal concentrations, and for each assay run at least 4 out of 6 QC samples were within the acceptable range.

Data Analysis. Plasma concentration versus time data was analyzed by non-compartmental approaches using the Win-Nonlin software program (version 5.2, Pharsight, Mountain View, Calif.) and the pharmacokinetic parameters T½, CL, Vss, $AUC_{(0-t)}$, $AUC_{(0-inf)}$, MRT, and graphs of plasma concentration versus time calculated for each.

REFERENCES

1. U.S. Pat. No. 7,550,155.
2. McKeage, K. and Perry, C. M. (2003) Propofol: A Review of its Use in Intensive Care Sedation of Adults, *CNS Drugs* 17, 235-272.
3. Ellett, M. (2010) Review of propofol and auxiliary medications used for sedation, *Gastroenterol. Nurs.* 33, 284-295; quiz 296.
4. Ellett, M. L. C. (2010) A literature review of the safety and efficacy of using propofol for sedation in endoscopy, *Gastroenterol. Nurs.* 33, 111-117.
5. Lamond, D. W. (2010) Review article: Safety profile of propofol for paediatric procedural sedation in the emergency department, *Emerg. Med. Australas.* 22, 265-286.
6. Symington, L. and Thakore, S. (2006) A review of the use of propofol for procedural sedation in the emergency department, *Emerg. Med. J.* 23, 89-93.
7. Sneyd, J. R. (2004) Recent advances in intravenous anaesthesia, *Br. J. Anaesth.* 93, 725-736.
8. Harris, E. A., Lubarsky, D. A., and Candiotti, K. A. (2009) Monitored anesthesia care (MAC) sedation: clinical utility of fospropofol, *Therapeutics and Clinical Risk Management* 5, 949-959.
9. Egan, T. et al. (2003) The pharmacokinetics and pharmacodynamics of propofol in a modified cyclodextrin formulation (Captisol) versus propofol in a lipid formulation (Diprivan): an electroencephalographic and hemodynamic study in a porcine model, *Anesth. Analg.* 97, 72-79, table of contents.
10. Ravenelle, F. et al. (2008) Novel lipid and preservative-free propofol formulation: properties and pharmacodynamics, *Pharm. Res.* 25, 313-319.
11. Sneyd, J. R. and Rigby-Jones, A. E. (2010) New drugs and technologies, intravenous anaesthesia is on the move (again), *Br. J. Anaesth.* 105, 246-254.
12. Levitzky, B. and Vargo, J. (2008) Fospropofol disodium injection for the sedation of patients undergoing colonoscopy, *Therapeutics and Clinical Risk Management* 4, 733-738.
13. Yavas, S. et al. (2008) Interactive web simulation for propofol and fospropofol, a new propofol prodrug, *Anesth. Analg.* 106, 880-883, table of contents.
14. Wuts, P. G. M. and Greene, T. W. (2006) *Greene's Protective Groups in Organic Synthesis,* 4th ed., John Wiley & Sons, Inc., Hoboken, N.J.
15. Stahl, P. H. and Wermuth, C. G., (Eds.) (2002) *Handbook of Pharmaceutical Salts: Properties Selection and Use*, Verlag Helvetica Chimica Acta/Wiley-VCH, Zurich.
16. Tronchet, J. M. J., Zsély, M., and Geoffroy, M. (1995) Spin-labelled glycolipid analogues: -glucose series, *Carbohydr. Res.* 275, 245-258.
17. Gottlieb, H. E., Kotlyar, V., and Nudelman, A. (1997) NMR Chemical Shifts of Common Laboratory Solvents as Trace Impurities, *The Journal of Organic Chemistry* 62, 7512-7515.
18. Glen, J. B. and Hunter, S. C. (1984) Pharmacology of an emulsion formulation of ICI 35 868, *Br J. Anaesth.* 56, 617-626.
19. Hart, B. (2000) 'Diprivan': a change of formulation, *Eur. J. Anaesthesiol.* 17, 71-73.
20. Knibbe, C. A. J. et al. (2004) Long-term sedation with propofol 60 mg ml$^{-1}$ vs. propofol mg$^{-1}$ ml in critically ill, mechanically ventilated patients, *Acta Anaesthesiol. Scand.* 48, 302-307.
21. Shao, X. et al. (2000) Bisulfite-containing propofol: is it a cost-effective alternative to Diprivan for induction of anesthesia?, *Anesth. Analg.* 91, 871-875.

22. Rau, J. et al. (2001) Propofol in an emulsion of long- and medium-chain triglycerides: the effect on pain, *Anesth. Analg.* 93, 382-384, 383rd contents page.
23. Ward, D. et al. (2002) Pharmacodynamics and pharmacokinetics of propofol in a medium-chain triglyceride emulsion, *Anesthesiology* 97, 1401-1408.
24. Paul, M. et al. (2003) Pharmacological characteristics and side effects of a new galenic formulation of propofol without soyabean oil, *Anaesthesia* 58, 1056-1062.
25. Fechner, J. et al. (2003) Pharmacokinetics and clinical pharmacodynamics of the new propofol prodrug GPI 15715 in volunteers, *Anesthesiology* 99, 303-313.
26. Bettschart-Wolfensberger, R. et al. (2000) Cardiopulmonary side-effects and pharmacokinetics of an emulsion of propofol (Disoprivan) in comparison to propofol solved in polysorbate 80 in goats, *J. Vet. Med. A Physiol. Pathol. Clin. Med.* 47, 341-350.
27. Song, D. et al. (2004) The pharmacodynamic effects of a lower-lipid emulsion of propofol: a comparison with the standard propofol emulsion, *Anesth. Analg.* 98, 687-691, table of contents.
28. Song, D. et al. (2004) Comparison of a lower-lipid propofol emulsion with the standard emulsion for sedation during monitored anesthesia care, *Anesthesiology* 100, 1072-1075.

TABLE 1

| Characteristics | Trade name | Manufacturer | References |
|---|---|---|---|
| Propofol 1% and 2% in 10% soya oil with or without EDTA Diprivan | Diprivan | AstraZeneca | [18, 19] |
| Propofol 6% in 10% soya oil | | | [20] |
| Propofol 1% and 2% in 10% soya oil with or without sodium sulphite | Various | Various | [21] |
| Propofol 1% and 2% in 10% long and medium chain triglycerides | Propofol Lipuro | Braun medical | [22, 23] |
| 'A new galenic formulation of propofol' | AM149 | Amrad | [24] |
| Propofol phosphate | Aquavan | Guildford Pharmaceuticals | [25] |
| Propofol polysorbate | | | [26] |
| Propofol 1% in 5% soya oil with or without EDTA | Ampofol | Amphastar Pharmaceuticals | [27, 28] |
| Propofol 1% in sulfobutyl ether-b-cyclodextrin (Captisol) | | CyDex Corporation | [9] |

TABLE 2

| Local anesthetics | Technique modifications | Antiemetics | Analgesics | Anesthetic agents | Other drugs |
|---|---|---|---|---|---|
| Lidocaine | 5 mm filter | Metoclopramide | Fentanyl | Nitrous oxide | Ephedrine |
| EMLA cream | Carrier fluid | Granisetron | Ketorolac | Thiopental | Magnesium sulphate |
| Prilocaine | Large vein | Dolasetron | Tramadol | Ketamine | Neostigmine |
| Lidocaine tape | Speed of injection | Ondansetron | Nafamostat mesilate | | Clonidine |
| Lidocaine iontophoresis | Aspiration of blood | Metoclopramide | Alfentanil | | Nitroglycerin |

TABLE 3

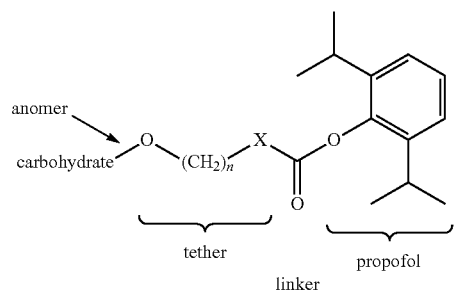

| Compound number | Carbohydrate | Anomer | Hetero atom X | Linker length (n) | Solubility[1] (mM) | Relative solubility |
|---|---|---|---|---|---|---|
| | propofol | — | — | — | 1.1[2] | 1 |
| 9 | Glucose | β (beta) | O | 2 | 9.4 | 8.6 |
| 12 | Glucose | β (beta) | O | 3 | 5.5 | 5.0 |
| 17 | Glucose | β (beta) | NH | 2 | 1.6[3] | 1.5 (2.3)[4] |
| 24 | Maltose | β (beta) | O | 2 | >20 | >20 |
| 25 | Maltose | β (beta) | O | 3 | >20 | >20 |
| 32 | Glucose | α (alpha) | O | 2 | 13.3 | 12.0 |
| 33 | Glucose | α (alpha) | O | 3 | 5.7[3] | 5.2 (8.1)[4] |

[1]Solubility determined by suspending the sample in several mLs of $D_2O$ and stirred vigorously for overnight. Each solution gave a soapy solution that was not filterable by a.2 μ syringe filter. A small amount of the solution was then separated and $D_2O$ added until the solution was clear (this solution first becomes opalescent). A weighed amount DSS was added (density measurements were also made and used to check the volume accuracy by using weight of the solution as a check). The resultant solution was then analysed by $^1H$ NMR and the relative concentration of analog versus DSS measured, allowing for solubility determination.

[2]Reported solubility of 0.7 mM

[3]Saturated solution was filterable and provided a clear, non-opalescent solution and thus should probably be compared to propofol's reported solubility of 0.7 mM rather than the 1.1 mM value.

[4]Relative to propofol's reported solubility of 0.7 mM

TABLE 4

| Test Article | Vehicle | Clinical Observation (times indicated are post-10 min infusion) |
|---|---|---|
| 9 | water, opalescent solution | Rats soporous at about 5 min and recovered at about 30 min |
| 12 | water, opalescent solution | Rats soporous at about 6 min and recovered at about 30 min |
| 17 | 10% Tween80, cloudy | Rat 1: breathless 13 min. and died at 15 min. Rat 2: breathless 3 min. and recovered at 10 min.; died at 40 min. from blood hemolysis Rat 3: breathless 3 min. and recovered at 10 min.; died at 1.5 h from hematuria |

TABLE 4-continued

| Test Article | Vehicle | Clinical Observation (times indicated are post-10 min infusion) |
|---|---|---|
| | | Additional Rat 4: died at infusion of 8 min. |
| 24 | water, clear solution | Rats soporous at about 5 min and recovered at about 30 min |
| 25 | water, clear solution | Rats soporous at about 7 min and recovered at about 35 min |
| 32 | water, opalescent solution | Rats soporous at about 3 min and recovered at about 26 min |
| 33 | water, opalescent solution | Rats soporous at about 3 min and recovered at about 30 min |
| Propofol | 5% cremophor, opalescent solution | Rats soporous at about 4 min and recovered at about 1.5 hr |

TABLE 5A

Species Male Sprague-Dawley rat
Food ad libitum
Dose route IV infusion

| | Compound ID | | | |
|---|---|---|---|---|
| | Propofol | 9 | 12 | 17 |
| Molecular Formula | $C_{12}H_{18}O$ | $C_{21}H_{32}O_9$ | $C_{22}H_{34}O_9$ | $C_{21}H_{33}NO_8$ |
| Molecular Weight | 178.28 | 428.44 | 442.67 | 427.49 |
| Nominal Dose (mg/kg)* | 30 | 72 | 74 | 72 |
| Nominal Dose (μmol/kg) | 168.3 | 168.1 | 167.2 | 168.4 |
| Administered Dose (mg/kg) | 64.9 | 64.9 | 72.3 | 47.7 |
| Administered Dose (μmol/kg) | 151.6 | 151.6 | 163.3 | 111.7 |
| Formulation | 3.0 mg/mL, 16.8 μmol/mL | 7.2 mg/mL, 16.8 μmol/mL | 7.4 mg/mL, 16.7 μmol/mL | 7.2 mg/mL, 16.8 μmol/mL in |

TABLE 5A-continued

Species Male Sprague-Dawley rat
Food ad libitum
Dose route IV infusion

| | Compound ID | | | |
|---|---|---|---|---|
| | Propofol | 9 | 12 | 17 |
| | in water, opalescent solution | in water, opalescent solution | in water, opalescent solution | 10% Tween in water, cloudy solution |
| Matrix | Plasma (EDTA-K2 as coagulant) | | | |

*Equivalent to 30 mg/kg propofol

TABLE 5B

Species Male Sprague-Dawley rat
Food ad libitum
Dose route IV infusion

| | Compound ID | | | |
|---|---|---|---|---|
| | 24 | 25 | 32 | 33 |
| Molecular Formula | $C_{27}H_{42}O_{14}$ | $C_{28}H_{44}O_{14}$ | $C_{21}H_{32}O_9$ | $C_{22}H_{34}O_9$ |
| Molecular Weight | 590.62 | 604.64 | 428.44 | 442.67 |
| Nominal Dose (mg/kg)* | 99 | 102 | 72 | 74 |
| Nominal Dose (μmol/kg) | 167.6 | 168.7 | 168.1 | 167.2 |
| Administered Dose (mg/kg) | 97 | 101 | 79.9 | 66.4 |
| Administered Dose (μmol/kg) | 164.3 | 170.6 | 186.5 | 149.9 |
| Formulation | 9.9 mg/mL, 16.8 μmol/mL in water, clear solution | 10.2 mg/mL, 16.9 μmol/mL in water, clear solution | 7.2 mg/mL, 16.8 μmol/mL in water, opalescent solution | 7.4 mg/mL, 16.7 μmol/mL in water, opalescent solution |
| Matrix | Plasma (EDTA-K2 as coagulant) | | | |

*Equivalent to 30 mg/kg propofol

TABLE 6

Mean concentration of prodrug and propofol in rat plasma after intravenous infusion administration (nmol/L)

| Time (h) | Propofol | 9 | 12 | 17 | 24 | 25 | 32 | 33 |
|---|---|---|---|---|---|---|---|---|
| 0 | n.d. | BQL | BQL | BQL | BQL | BQL | BQL | BQL |
| 0.083 | 21795 | BQL | 4.11 | 178796 | 3200 | 34401 | 4.88 | 16.5 |
| 0.167 | 31510 | BQL | 6.78 | 312678 | 7740 | 68360 | 4.97 | 23.1 |
| 0.2 | 19613 | BQL | BQL | 152206 | 1029 | 22658 | 2.68 | 9.59 |
| 0.25 | 13370 | BQL | BQL | 119535 | 751 | 9074 | BQL | BQL |
| 0.417 | 3827 | BQL | BQL | 35206 | 36 | 997 | BQL | BQL |
| 0.667 | 3122 | BQL | BQL | 19837 | 11.2 | 97.1 | BQL | BQL |
| 1.166 | 1642 | BQL | BQL | 8012 | 3.01 | 16.2 | BQL | BQL |
| 2.166 | 841 | BQL | BQL | 2083 | BQL | 2.09 | BQL | BQL |
| 3.166 | 332 | BQL | BQL | 390.7 | 4.2 | BQL | BQL | BQL |
| 4.166 | 259 | BQL | BQL | 82.5 | BQL | BQL | BQL | BQL |
| 6.166 | 230 | BQL | BQL | 10.6 | BQL | BQL | BQL | BQL |
| Cmax (nM) | 31935 | n.d. | 6.78 | 312678 | 8104 | 68360 | 5.38 | 23.1 |
| Tmax (h) | 0.18 | n.d. | 0.17 | 0.17 | 0.14 | 0.17 | 0.14 | 0.17 |
| $t_{1/2}$ (h) | 6.39 | n.d. | 0.06 | 0.437 | 0.887 | 0.253 | n.d. | n.d. |
| $CL_p$ (mL/min/kg) | 264.7 | n.d. | 2278436 | 39.1 | 5804 | 337 | n.d. | n.d. |

TABLE 6-continued

Mean concentration of prodrug and propofol in rat plasma after intravenous infusion administration (nmol/L)

| Time (h) | Propofol | 9 | 12 | 17 | 24 | 25 | 32 | 33 |
|---|---|---|---|---|---|---|---|---|
| $Vd_{ss}$ (L/kg) | 61.2 | n.d. | 13272 | 0.657 | 120 | 1.51 | n.d. | n.d. |
| $AUC_{last}$ (nM · h) | 10576 | n.d. | 0.773 | 61644 | 786 | 8571 | 0.657 | 3.04 |
| $AUC_{inf}$ (nM · h) | 12634 | n.d. | 1.22 | 71764 | 791 | 8574 | n.d. | n.d. |
| $MRT_{inf}$ (h) | 3.48 | n.d. | 0.1 | 0.277 | 0.207 | 0.077 | n.d. | n.d. |
| LLOQ (ng/mL) | 10 | 1 | 1 | 1 | 1 | 1 | 1 | 2 |
| LLOQ (nmol/L) | 56.09 | 2.33 | 2.26 | 2.34 | 1.69 | 1.65 | 2.33 | 4.52 |

$C_0$—Initial concentration at time 0, extrapolated.;

$t_{1/2}$—Half-life of the pro-drug analog (Table 4).;

$CL_p$—Estimate of total body clearance, $CL_p$ = dose/$AUC_{inf}$;

$Vd_{ss}$—Estimate of the volume of distribution; $Vd_{ss}$ = dose/$AUC_{inf}$;

$AUC_{last}$—Area under the curve of time versus concentration, to the last detected concentration;

$AUC_{inf}$—Area under the curve of time versus concentration, with concentration extrapolated to infinity;

$MRT_{inf}$—Mean Residence Time when the drug concentration profile is extrapolated to infinity.;

LLOQ—Low limit of quantitation;

n.d.—Not determined;

BQL—below quantitation limit

TABLE 7

Mean Concentration of Propofol (nmol/L) in Rat Plasma After Intravenous Administration

| Time (h) | Propofol | from 9 | from 12 | from 17 | from 24 | from 25 | from 32 | from 33 |
|---|---|---|---|---|---|---|---|---|
| 0 | BQL | BQL | BQL | BQL | BQL | BQL | BQL | BQL |
| 0.083 | 21795 | 32327 | 26438 | 1103 | 182858 | 323274 | 27373 | 14902 |
| 0.167 | 31510 | 36385 | 36273 | 1073 | 152943 | 358986 | 33561 | 16528 |
| 0.2 | 19613 | 14397 | 13368 | 790 | 32589 | 140416 | 10171 | 6144 |
| 0.25 | 13370 | 8283 | 8582 | 663 | 18211 | 73854 | 6806 | 2984 |
| 0.417 | 3827 | 5544 | 3754 | 463 | 4616 | 11181 | 2941 | 1486 |
| 0.667 | 3122 | 2416 | 2361 | 236 | 2526 | 2990 | 1855 | 851 |
| 1.166 | 1642 | 963 | 665 | 97 | 1088 | 1182 | 875 | 441 |
| 2.166 | 841 | 467 | 197 | BQL | 440 | 515 | 361 | 227 |
| 3.166 | 332 | 286 | 95.7 | BQL | 388 | 279 | 221 | 136 |
| 4.166 | 259 | 227 | BQL | BQL | 188 | 220 | 154 | BQL |
| 6.166 | 230 | 242 | BQL | BQL | 112 | 123 | 98 | BQL |
| Cmax (nM) | 31935 | 42443 | 36272 | 1124 | 182859 | 367400 | 33561 | 18043 |
| Tmax (h) | 0.18 | 0.14 | 0.17 | 0.11 | 0.08 | 0.14 | 0.17 | 0.14 |
| $t_{1/2}$ (h) | 6.39 | 4.53 | 0.67 | 0.353 | 1.95 | 2.66 | 2.97 | 1 |
| $AUC_{last}$ (nM · h) | 10576 | 11716 | 9101 | 389 | 30384 | 64735 | 8051 | 4578 |
| $AUC_{inf}$ (nM · h) | 12634 | 13523 | 9239 | 543 | 30781 | 65228 | 8460 | 4793 |
| $MRT_{inf}$ (h) | 3.48 | 2.49 | 0.423 | 0.46 | 0.403 | 0.313 | 1.16 | 0.547 |
| LLOQ (ng/mL) | 10 | 10 | 10 | 10 | 10 | 10 | 10 | 20 |
| LLOQ (nmol/L) | 56.09 | 56.09 | 56.09 | 56.09 | 56.09 | 56.09 | 56.09 | 112.2 |

TABLE 8

| compound | Compd # | carb | anomer Y | R¹, R², R³ etc | m, n, p, q | X | Z |
|---|---|---|---|---|---|---|---|
| (glucose structure) | 9 | glucose | β  O | R¹ = R² = H | m = 2, n = 0, p = 0, q = 1 | O | O |
| (glucose structure) | 12 | glucose | β  O | R¹ = R² = H | m = 3, n = 0, p = 0, q = 1 | O | O |
| (glucose structure) | 17 | glucose | β  O | R¹ = R² = H | m = 2, n = 0, p = 0, q = 1 | NH | O |
| (maltose structure) | 24 | maltose | β  O | R¹ = R² = H | m = 2, n = 0, p = 0, q = 1 | O | O |
| (maltose structure) | 25 | maltose | β  O | R¹ = R² = H | m = 3, n = 0, p = 0, q = 1 | O | O |

TABLE 8-continued $$\text{carbohydrate} \overset{\text{anomer}}{\longrightarrow} Y - \underbrace{(CR^1R^2)_m(CR^3R^4)_n(CR^5R^6)_p}_{\text{tether}} - X - \underbrace{\overset{O}{\underset{\|}{C}}(Z)_q}_{\text{linker}} - O - \text{(2,6-diisopropylphenyl)}$$

CARB     T     L     Propofol

| compound | Compd # | carb | anomer | Y | R¹, R², R³ etc | m, n, p, q | X | Z |
|---|---|---|---|---|---|---|---|---|
| [glucose-O-CH₂CH₂-O-C(O)-O-propofol] | 32 | glucose | α | O | R¹ = R² = H | m = 2, n = 0, p = 0, q = 1 | O | O |
| [glucose-O-(CH₂)₃-O-C(O)-O-propofol] | 33 | glucose | α | O | R¹ = R² = H | m = 3, n = 0, p = 0, q = 1 | O | O |
| [(glucose-O-CH₂CH(CH₂-Y-CARB)-O-C(O)-O-propofol)₂] | | glucose | β | O | R¹ = R² = H, R³ = CH₂—Y—CARB, R⁴ = H | m = 1, n = 1, p = 0, q = 1 | O | O |
| [(glucose-O-CH₂CH(CH₂-Y-CARB)CH₂-O-C(O)-O-propofol)₂] | | glucose | β | O | R¹ = R² = H, R³ = CH₂—Y—CARB, R⁴ = H, R⁵ = R⁶ = H | m = 1, n = 1, p = 1, q = 1 | O | O |
| [glucose-O-CH₂CH₂-N(CH₂CO₂Na)-C(O)-O-propofol] | | glucose | β | O | R¹ = R² = H | m = 2, n = 0, p = 0, q = 1 | NCH₂CO₂Na | O |

TABLE 8-continued

| compound | Compd # | anomer carb | Y | $R^1, R^2, R^3$ etc | m, n, p, q | X | Z |
|---|---|---|---|---|---|---|---|
| [glucose disaccharide structure] | | glucose | β | O | $R^1 = R^2 = H$ | m = 2, n = 0, p = 0, q = 1 | $NCH_2CH_2-Y-CARB$ | O |
| [mannose cyclopentyl carbonate structure] | | mannose | α | O | $R^1 = R^3 = H$; $R^2$ and $R^4$ joined = $CH_2CH_2CH_2$ | m = 1, n = 1, p = 0, q = 1 | O | O |
| [galactose tetrahydropyran structure] | | galactose | β | O | $R^1 = R^2 = H$; $R^3$ and $R^4$ joined = $CH_2CH_2OCH_2CH_2$; $R^5 = R^6 = H$ | m = 1, n = 1, p = 1, q = 1 | O | O |
| [glucose piperidine carbamate structure] | | glucose | β | O | $R^1 = R^2 = R^3 = H$; $R^4$ joined with R of X = $CH_2CH_2CH_2$; $R^5 = R^6 = H$ | m = 1, n = 1, p = 1, q = 1 | NR; R joined with $R^4$, = $CH_2CH_2CH_2$ | O |

TABLE 8-continued

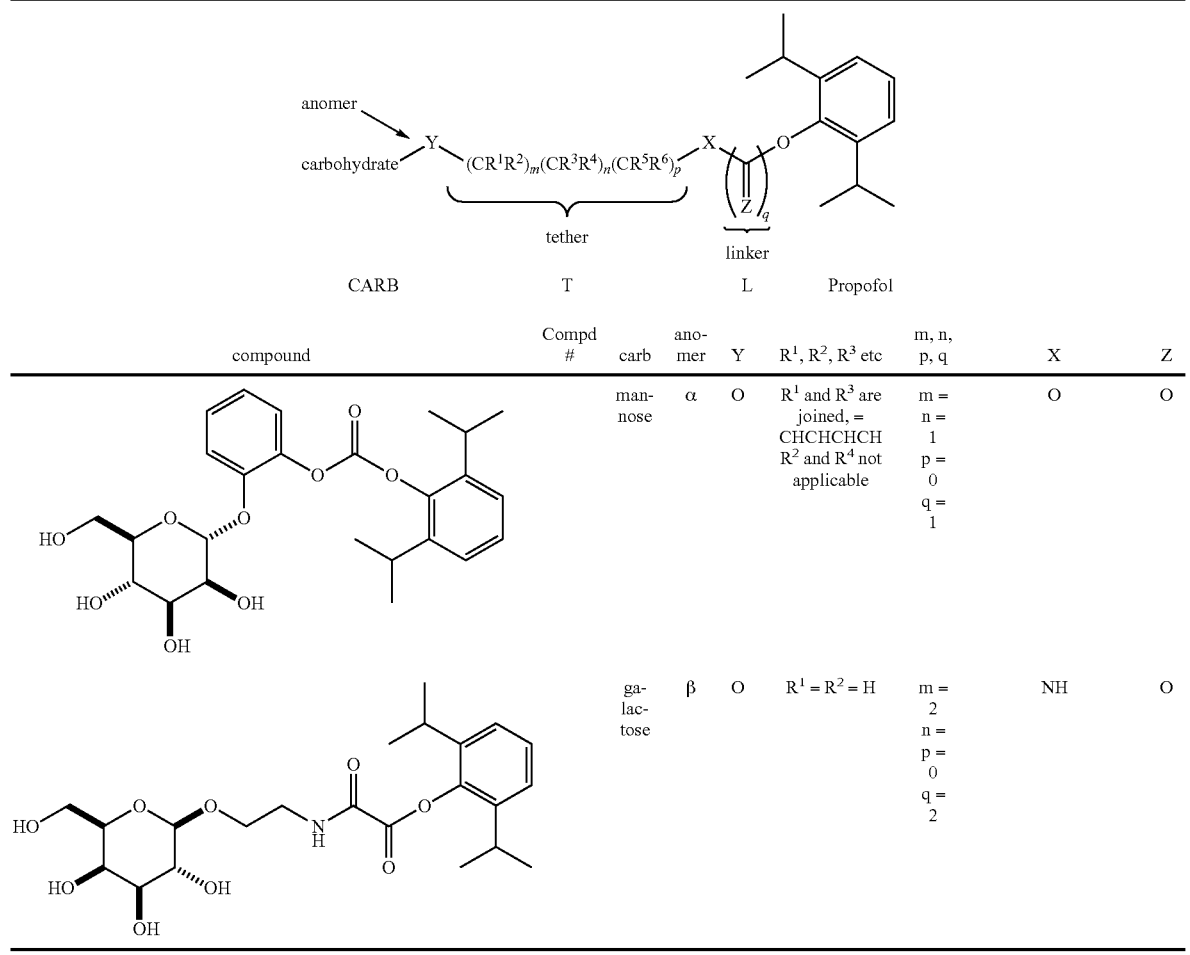

We claim:

1. A glycosylated propofol compound of the formula: CARB-T-L-Propofol having the structure:

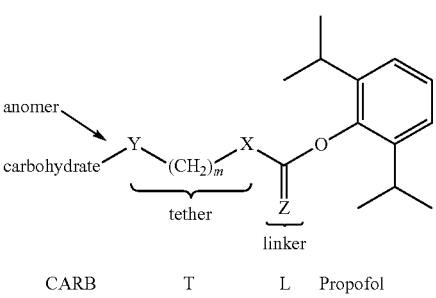

wherein CARB is a carbohydrate connected through a chemical tether T to linking group L which is connected to Propofol, wherein said carbohydrate is selected from the group consisting of a mono-, di- and tri-saccharides, wherein said linker is created by chemical modification of a hydroxyl group on propofol, wherein said tether is connected to the anomeric carbon of said carbohydrate, wherein Z is O, Y is O or S, and X is O, wherein m is 2 or 3, and wherein the anomer is either α or β.

2. The glycosylated propofol compound of claim 1, wherein said carbohydrate is a cyclic monosaccharide.

3. The glycosylated propofol compound of claim 2, wherein said cyclic monosaccharide is a pyranoside.

4. The glycosylated propofol compound of claim 2, wherein said cyclic monosaccharide is a furanoside.

5. The glycosylated propofol compound of claim 1, wherein said carbohydrate has hydroxyl protecting groups.

6. The glycosylated propofol compound of claim 5, wherein said protecting groups are acetyl groups.

7. The glycosylated propofol compound of claim 5, wherein said carbohydrate is an acetylated pyranoside.

8. The glycosylated propofol compound of claim 1, wherein the structure is:

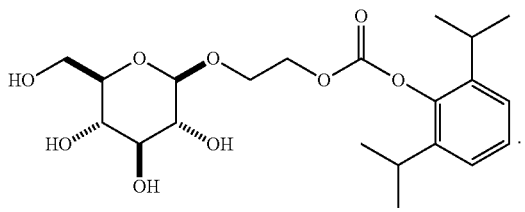 [SMILES: CC(C)c1cccc(C(C)C)c1OC(=O)OCCO[C@@H]1O[C@H](CO)[C@@H](O)[C@H](O)[C@H]1O]

9. The glycosylated propofol compound of claim 1, wherein the structure is:

10. The glycosylated propofol compound of claim 1, wherein the structure is:

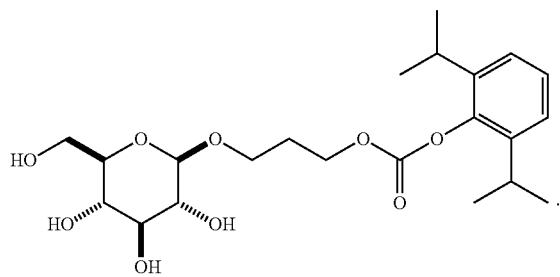 [SMILES: CC(C)c1cccc(C(C)C)c1OC(=O)OCCCO[C@@H]1O[C@H](CO)[C@@H](O)[C@H](O)[C@H]1O]

11. The glycosylated propofol compound of claim 1, wherein the structure is:

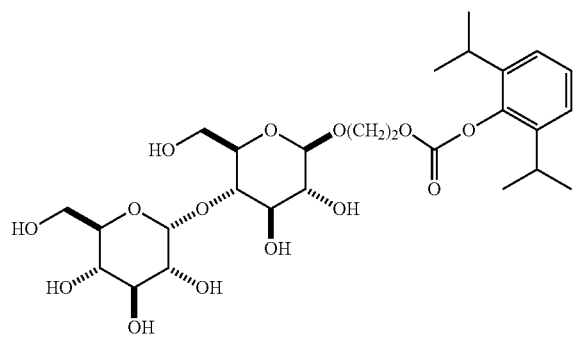

12. The glycosylated propofol compound of claim 1, wherein the structure is:

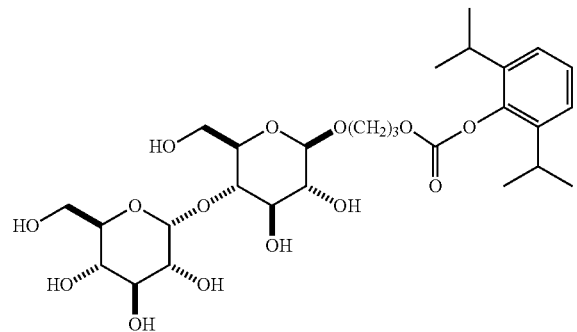

13. The glycosylated propofol compound of claim 1, wherein the structure is:

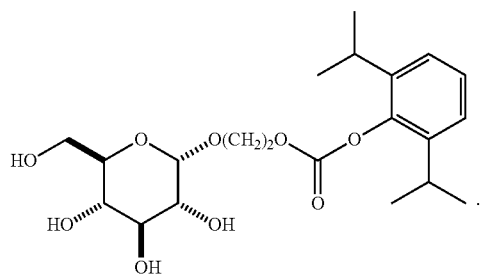

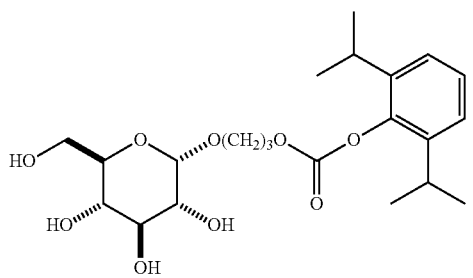

14. The glycosylated propofol compound of claim 1, wherein said compound is dissolved in a diluent selected from the group consisting of water, saline, dextrose, glycerol, polyethylene glycol, and poly(ethylene glycol methyl ether).

15. A water-based formulation suitable for intravenous administration comprising the glycosylated propofol compound of claim 1.

16. The glycosylated propofol compound of claim 15, wherein the solubility of said glycosylated propofol compound in said water-based formulation is greater than the solubility of propofol.

17. A glycosylated propofol compound of the formula CARB-T-L-Propofol having the structure:

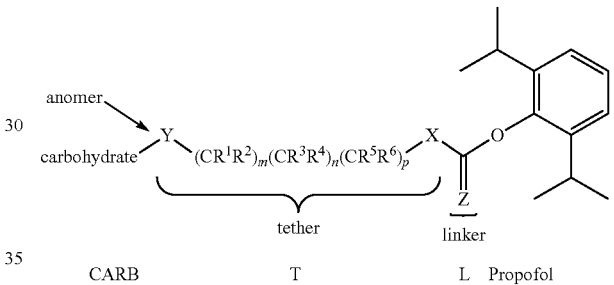

wherein CARB is a carbohydrate connected through a chemical tether T to linking group L which is connected to Propofol, wherein said carbohydrate is selected from the group consisting of a mono-, di- and tri-saccharides, wherein Z is O, Y is O or S, and X is O, wherein the sum of m, n and p is 2 or 3, where R1, R2, R3, R4, R5 and R6 are each independent and can be hydrogen, alkyl, aryl, substituted alkyl, substituted aryl, arylalkyl, substituted arylalkyl, cycloalkyl, substituted cycloalkyl, heteroalkyl, substituted heteroalkyl, heteroaryl, substituted heteroaryl, heterocyclyl, substituted heterocycl, heteroarylalkyl, or substituted heteroarylalkyl, and wherein the anomer is either α or β.

18. The glycosylated propofol compound of claim 17, wherein the structure is:

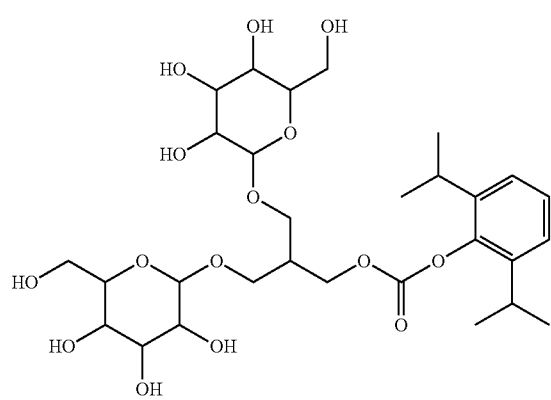

19. The glycosylated propofol compound of claim 17, wherein the structure is:

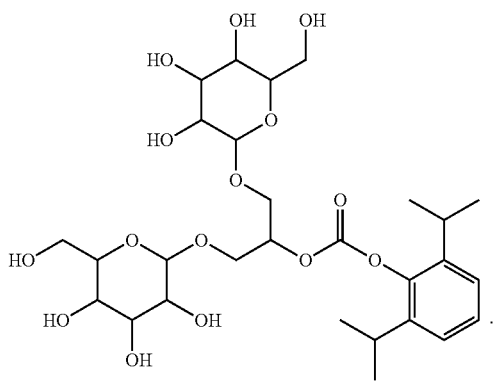 [SMILES: CC(C)c1cccc(C(C)C)c1OC(=O)OC(COC1OC(CO)C(O)C(O)C1O)COC1OC(CO)C(O)C(O)C1O]

20. A method for making the glycosylated propofol compound of claim 17, said method comprising:
a) providing propofol and a modified carbohydrate, said modified carbohydrate having the structure:

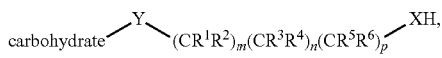

wherein X is O, and wherein Y is either O or S and is connected to the anomeric carbon of said carbohydrate;
b) modifying the hydroxyl group on propofol, so as to create a modified propofol comprising a linker intermediate; and
c) reacting said modified propofol with said modified carbohydrate, so as to create the glycosylated compound of claim 17.

21. The method of claim 20, wherein said modified carbohydrate has hydroxyl protecting groups.

22. The method of claim 21, wherein said protecting groups are acetyl groups.

23. The method of claim 21, wherein said carbohydrate is an acetylated pyranoside.

24. The method of claim 21, wherein after step c) said protecting groups are removed.

25. The method of claim 20, wherein said linker intermediate is a haloformate.

26. The method of claim 25, wherein said haloformate is a chloroformate.

27. The method of claim 20, wherein the reacting of step c) converts said linker intermediate into said linker.

28. The method of claim 20, wherein said modified carbohydrate is selected from the group consisting of a mono-, di- and tri-saccharides.

29. A method of treating a subject in need of anesthesia comprising:
a) providing the glycosylated propofol compound of claim 17; and
b) administering said glycosylated propofol compound to a subject in need of such treatment.

30. The method of claim 29, wherein said subject is a human.

31. The method of claim 29, wherein said subject is a non-human animal.

32. The method of claim 30, wherein said human is mechanically ventilated.

33. The method of claim 29, wherein said glycosylated propofol compound is in a water-based formulation and wherein said administering comprises intravenous administration.

34. The method of claim 30, wherein said human, after said administering, is sedated.

* * * * *